US008691817B2

(12) United States Patent
Von Nussbaum et al.

(10) Patent No.: US 8,691,817 B2
(45) Date of Patent: *Apr. 8, 2014

(54) SULFONIC AMIDE AND SULFOXIMINE-SUBSTITUTED DIARYL-DIHYDROPYRIMIDINONES AND USAGE THEREOF

(75) Inventors: Franz Von Nussbaum, Düsseldorf (DE); Dagmar Karthaus, Solingen (DE); Sonja Anlauf, Wermelskirchen (DE); Martina Delbeck, Essen (DE); Volkhart Min-Jian Li, Velbert (DE); Daniel Meibom, Leverkusen (DE); Klemens Lustig, Wuppertal (DE); Dirk Schneider, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 103 days.

This patent is subject to a terminal disclaimer.

(21) Appl. No.: 13/262,159

(22) PCT Filed: Mar. 30, 2010

(86) PCT No.: PCT/EP2010/002000

§ 371 (c)(1),
(2), (4) Date: Dec. 27, 2011

(87) PCT Pub. No.: WO2010/115548

PCT Pub. Date: Oct. 14, 2010

(65) Prior Publication Data

US 2012/0094968 A1    Apr. 19, 2012

(30) Foreign Application Priority Data

Apr. 6, 2009 (DE) .................. 10 2009 016 553

(51) Int. Cl.
*C07D 239/22* (2006.01)
*A61K 31/505* (2006.01)

(52) U.S. Cl.
USPC ......... 514/235.8; 514/275; 544/122; 544/315

(58) Field of Classification Search
USPC .................. 544/122, 315; 514/235.8, 275
See application file for complete search history.

(56) References Cited

U.S. PATENT DOCUMENTS

| | | | |
|---|---|---|---|
| 7,566,723 B2 | 7/2009 | Gielen-Haertwig et al. | |
| 7,687,510 B2 | 3/2010 | Gielen-Haertwig et al. | |
| 7,893,073 B2 | 2/2011 | Gielen-Haertwig et al. | |
| 8,288,402 B2 * | 10/2012 | Von Nussbaum et al. ..... | 514/274 |
| 2008/0064704 A1 | 3/2008 | Gielen-Haertwig et al. | |
| 2008/0103164 A1 | 5/2008 | Gudmundsson et al. | |
| 2010/0010024 A1 | 1/2010 | Von Nussbaum et al. | |
| 2010/0184788 A1 | 7/2010 | Gielen-Haertwig et al. | |
| 2011/0034433 A1 | 2/2011 | Von Nussbaum et al. | |

FOREIGN PATENT DOCUMENTS

| | | |
|---|---|---|
| WO | 2005009392 | 2/2005 |
| WO | 2006082412 | 8/2006 |
| WO | 2006136857 | 12/2006 |
| WO | 2007042815 | 4/2007 |
| WO | 2008030158 | 3/2008 |
| WO | WO 2009/080199 | * 7/2009 |

OTHER PUBLICATIONS

Ohbayashi, Neutrophil elastase inhibitors as treatment for COPD, Expert Opin. Invest. Drugs (2002), 11 (7), pp. 965-980.*
Stockley et al., "Neutrophils and Protease/Antiprotease Imbalance," Am. J. Respir. Crit. Care Med., 1999, vol. 160, S49-S52.
Humbert et al., "Cellular and molecular pathobiology of pulmonary arterial hypertension," J. Am. Coll. Cardiol., Jun. 16, 2004, vol. 43(12): 13S-24S.
D'Alonzo et al., "Survival in patients with primary pulmonary hypertension," Ann. Intern. Med., 1991, vol. 115, 343-349.
Ghofrani et al., "Neue therapieoptionen in der behandlung der pulmonalarteriellen hypertonie," Herz, 2005, vol. 30(4): 296-302.
Rosenzweig, "Emerging treatments for pulmonary arterial hypertension," Expert Opin. Emerging Drugs 2006, vol. 11 (4): 609-619.
Schaaf et al., "Neutrophil inflammation and activation in bronchiectasis: comparison with pneumonia and idiopathic pulmonary fibrosis," Respiration 2000, vol. 67, 52-59.
Rabinovitch et al., "Pulmonary arter endothelial abnormalities in patients with contenital heart defects and pulmonary hypertension," Lab. Invest., 1986, vol. 55(6): 632-653.
Todorovich-Hunter et al., "Increased pulmonary artery elastolytic activity in adult rats with monocrotaline-induced progressive hypertensive pulmonary vascular disease compared with infant rats with nonprogressive disease," Am. Rev. Respir. Dis., 1992, vol. 146, 213-223.
Rabinovitch et al., "Comroe Lecture: EVE and beyond, retro and prospective insights," Am. J. Physiol. 1999, vol. 277, L5-L12.
Zaidi et al., "Overexpression of the serine elastase inhibitor elafin protects transgenic mice from hypoxic pulmonary hypertension," Circulation 2002, vol. 105, 516-521.
Cowan et al., "Complete reversal of fatal pulmonary hypertension in rats by a serine elastase inhibitor," Nature Med., 2000, vol. 6(16): 698-702.
Simonneau et al., "Clinical classification of pulmonary hypertension," J. Am. Coll. Cardiol., 2004, 43(12): 5S-12S.
Barnes et al., "Chronic obstructive pulmonary disease," N. Engl. J. Med., 2000, vol. 343(4): 269-280.
Gadek et al., "Antielastases of the Human Alveolar Structures: Implications for the Protease-Antiprotease Theory of Emphysema," J. Clin. Invest., Oct. 1981, vol. 68, 889-898.
Werb et al., "Elastases and elastin degradation," J. Invest. Dermatol. 1982, vol. 79, 154-159.
Janoff et al., "Elastases and emphysema," Am. Rev. Respir. Dis., 1985, vol. 132, 417-433.

(Continued)

*Primary Examiner* — Deepak Rao
(74) *Attorney, Agent, or Firm* — Karen B. King

(57) ABSTRACT

The present application relates to novel sulfonamide- or sulfoximine-substituted 1,4-diaryldihydropyrimidin-2-one derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

9 Claims, No Drawings

(56) References Cited

OTHER PUBLICATIONS

Liou et al., "Nonisotropic enzyme-inhibitor interactions: a novel nonoxidative mechanism for quantum proteolysis by human neutrophils," Biochemistry 1995, 34(49): 16171-16177.

Elssner et al., "The role of neutrophils in the pathogenesisi of obliterative bronchiolitis after lung transplantation," Transpl. Infect. Dis. 2001, vol. 3, 168-176.

Chollet-Martin et al., "Interactions between neutrophils and cytokines in blood and alveolar spaces during ARDS," Am. J. Respir. Crit. Care Med. 1996, 154, 594-601.

Namazi, et al., "Investigation of the Chemical Reactivity of Positions N-3, C-5, and C-6-Methyl Group in Biginelli Type Compounds and Synthesis of New Dihydropyrimidine Derivatives," J. Heterocyclic Chem, 2001, 38:1051-1054.

Luhr et al., "Incidence and mortality after acute respiratory failure and acute respiratory distress syndrome in Sweden, Denmark, and Iceland," Am. J. Respir Crit. Care Med. 1999, vol. 159, 1849-1861.

U.S. Appl. No. 12/809,781, filed Sep. 9, 2010.

* cited by examiner

SULFONIC AMIDE AND SULFOXIMINE-SUBSTITUTED DIARYL-DIHYDROPYRIMIDINONES AND USAGE THEREOF

The present application relates to novel sulfonamide- or sulfoximine-substituted 1,4-diaryldihydropyrimidin-2-one derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

Human leukocyte elastase (HLE, EC 3.4.21.37), also called human neutrophil elastase (HNE, hNE), belongs to the family of the serine proteases. The proteolytic enzyme is found in the azurophilic granules of polymorphonuclear leukocytes (PMN leukocytes). Intracellular elastase performs an important function in defense against pathogens by breaking down the foreign particles taken by phagocytosis. Activated neutrophilic cells release the HNE from the granules into the extracellular space (extracellular HNE), with some of the released HNE remaining on the outside of the neutrophilic cell membrane (membrane-associated HNE). The highly active enzyme is able to break down a large number of connective tissue proteins, for example the proteins elastin, collagen and fibronectin. Elastin occurs in high concentrations in all tissue types showing high elasticity, for example in the lung and the arteries. HNE is involved in the tissue breakdown and transformation (tissue remodeling) associated with a large number of pathological processes (for example tissue injuries). HNE is also an important modulator of inflammatory processes. HNE induces for example increased interleukin-8 (IL-8) gene expression.

Accordingly, it is presumed that HNE plays an important role in many disorders, injuries and pathological changes whose formation and/or progression are/is associated with inflammatory events and/or proliferative and hypertrophic tissue and vessel transformation. This can be in particular disorders and/or injuries of the lung or the cardiovascular system, or it may be sepsis, cancerous disorders or other inflammatory disorders.

Disorders and injuries of the lung which may be mentioned in this context are in particular chronic obstructive pulmonary disease (COPD), acute respiratory distress syndrome (ARDS), bronchiectasis, bronchiolitis obliterans, cystic fibrosis (CF; also referred to as mucoviscidosis), lung emphysema and acute lung injury (ALI). Disorders and injuries of the cardiovascular system where HNE is involved are, for example, tissue transformations during heart failure and reperfusion damage after acute myocardial infarction (AMI), cardiogenic shock, acute coronary syndrome (ACS), and also aneurysms. Disorders associated with sepsis are, for example, systemic inflammatory response syndrome (SIRS), severe sepsis, septic shock and multi-organ failure (MOF; multi-organ dysfunction, MODS) and also disseminated intravascular coagulation (DIC). Examples of tissue breakdown and transformation in cancerous processes are the migration of cancer cells into healthy tissue (formation of metastases) and the formation of new supply blood vessels (neo-angiogenesis). Other inflammatory diseases where HNE plays a role are rheumatoid disorders, for example rheumatoid arthritis, inflammatory bowel disease (IBD), Crohn's disease (CD); ulcerative colitis (UC) and arteriosclerosis.

It is generally assumed that elastase-mediated pathological processes are based on a displaced equilibrium between free elastase and endogenous elastase inhibitor protein (mainly alpha-1 antitrypsin, AAT) [*Neutrophils and protease/antiprotease imbalance*, Stockley, *Am. J. Respir. Crit. Care Med.* 160, 49-52 (1999)]. AAT is present in large excess in the plasma and thus very rapidly neutralizes free HNE. The concentration of free elastase is elevated in various pathological processes, so that there is a local shift in the balance between protease and protease inhibitor in favor of the protease. In addition, membrane-associated elastase of the activated PMN cells is very substantially protected from inhibition by AAT. The same applies to free elastase, which is located in a microcompartment which is difficult to access between the neutrophilic cell and the adjoining tissue cell (for example endothelial cell). In addition, strong oxidizing conditions prevail in the vicinity of activated leukocytes (oxidative burst), and thus AAT is oxidized and loses several orders of magnitude in the inhibitory effect.

Novel elastase-inhibiting active compounds (exogenously administered inhibitors of HNE) ought accordingly to have a low molecular weight in order to be able also to reach and inhibit the membrane-associated HNE and the HNE present in the protected microcompartment (see above). Also necessary for this purpose is good in vivo stability of the substances (low in vivo clearance). In addition, these compounds ought to be stable under oxidative conditions in order not to lose inhibitory power in the pathological process.

Pulmonary arterial hypertension (PAH) is a progressive lung disorder which, untreated, leads to death on average within 2.8 years after being diagnosed. An increasing constriction of the pulmonary circulation leads to increased stress on the right heart, which may develop into right heart failure. By definition, the mean pulmonary aterial pressure (mPAP) in case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., *J. Am. Coll. Cardiol.* 2004, 43, 13S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., *Ann. Intern. Med.* 1991, 115, 343-349).

Despite all the advances in the therapy of pulmonary arterial hypertension there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently.

Novel combination therapies are one of the most promising future therapeutic options for the treatment of pulmonary arterial hypertension. In this connection, the finding of novel pharmacological mechanisms for the treatment of PAH is of particular interest (Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733). Therapeutic options which intervene directly in the remodeling event (antiremodeling mechanisms reverse remodeling mechanisms) in particular might form the basis for a more causal treatment and thus be of great advantage for the patients. In this connection, it will be possible to combine known and novel therapies. In order to minimize the risk of interfering medicament-medicament interactions in such a combination therapy, these novel active compounds ought inhibit metabolizing P450 CYP enzymes only to a very small extent or not at all.

These days, one proceeds on the assumption that elastase plays a central role in pathological remodeling. It has been possible to find a fragmentation of connective tissue (internal elastic lamina) in animal models and in patients with elevated pulmonary arterial blood pressure (pulmonary arterial hypertension) [Rabinovitch et al., *Lab. Invest.* 55, 632-653 (1986)], and it was possible to show in animal models of pulmonary arterial hypertension (hypoxic rat and mouse model, monocrotaline rat model) that elastase activity was increased and was associated with the fragmentation of connective tissue [Todorovich-Hunter et al., *Am. Rev. Respir. Dis.* 146, 213-223 (1992)]. It is suspected that the tissue remodeling to be observed during the disease process of pulmonary arterial hypertension is induced by an elastase-mediated release of connective tissue-associated growth factors, for example of basic fibroblast growth factor (bFGF) [Rabinovitch, *Am. J. Physiol.* 277, L5-L12 (1999)]. It was possible to show a positive effect with an overexpressed elastase inhibitor protein in the hypoxic mouse model of pulmonary arterial hypertension [Zaidi et al., *Circulation* 105, 516-521 (2002)]. It was possible to show a positive effect with synthetic low-molecular-weight elastase inhibitors in the monocrotaline rat model of pulmonary arterial hypertension; in this case a beneficial effect on tissue remodeling was also to be noted [Cowan et al., *Nature Med.* 6, 698-702 (2000)]. However, all previously disclosed low-molecular-weight elastase inhibitors have low selectivity, are chemically reactive and/or have only limited oral availability, thus to date thwarting clinical development of an oral elastase inhibitor for these indications.

The term "pulmonary arterial hypertension" includes particular types of pulmonary hypertension as have been specified for example by the World Health Organization (WHO) (*Clinical Classification of Pulmonary Hypertension*, Venice 2003; G. Simonneau et al., *J. Am. Coll. Cardiol.* 2004, 43, 5S-12S).

According to this classification, pulmonary arterial hypertension includes idiopathic pulmonary arterial hypertension (IPAH, formerly also called primary pulmonary hypertension, PPH), familial pulmonary arterial hypertension (FPAH), persistent pulmonary hypertension in neonates and also associated pulmonary arterial hypertension (APAH) which is associated with collagenoses, congenital systemic-pulmonary shunt vitiae, portal hypertension, HIV infections, intake of particular drugs and medicaments (for example anorectics), with disorders having a significant venous/capillary involvement, such as pulmonary venal-occlusive disease and pulmonary capillary hemangiomatosis, or with other disorders such as thyroid disorders, glycogen storage diseases, Gaucher's disease, hereditary teleangiectasia, hemoglobinopathies, myeloproliferative disorders and splenectomy.

Other types of pulmonary hypertension include, for example, the pulmonary hypertension associated with left heart disorders, for example with ventricular or valvular disorders, the pulmonary hypertension associated with disorders of the respiratory tract and/or of the lungs, for example with chronic obstructive lung disease, interstitial lung disease or pulmonary fibrosis, the pulmonary hypertension attributable to chronic thrombotic and/or embolic disorders, for example associated with thromboembolic obstruction of pulmonary arteries, and the pulmonary hypertension caused by generally inflammatory disease processes or by special causes (for example associated with schistosomiasis, sarcoidosis and neoplastic diseases).

Chronic obstructive pulmonary disease (COPD) is a pulmonary disease which progresses slowly and is characterized by obstruction of breathing caused by pulmonary emphysema and/or chronic bronchitis. First symptoms of the disorder generally appear from the fourth to the fifth decade of life onwards. In the years that follow, the short breath frequently worsens and a cough, associated with extensive and sometimes prolonged discharge and obstructed breathing up to breathlessness (dyspnea), manifests itself. COPD is primarily a smoker's disease: smoking is responsible for 90% of all cases of COPD and 80-90% of all deaths caused by COPD. COPD is a major medical problem and represents the sixth most frequent cause of death world-wide. About 4-6% of people over the age of 45 are affected.

Although the obstruction of breathing may only be partial and temporal, COPD cannot be cured. Accordingly, the target of the treatment is to improve the quality of life, to ameliorate the symptoms, to prevent acute worsening and to slow the progressive impairment of pulmonary function. Existing pharmacotherapies, which have hardly changed over the last two to three decades, are the use of bronchodilators to open up blocked respiratory paths, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the force behind the development of the disease. The mechanism on which it is based involves immune cells which, during the course of the inflammatory reaction of the lung, secrete various chemokines. This attracts neutrophilic cells and subsequently alveolar macrophages to the connective tissue of the lung and the lumen. Neutrophilic cells secrete a protease cocktail which contains mainly HNE and protease 3. This causes the local protease/antiprotease balance to shift in favor of the proteases, resulting inter alia in an unchecked elastase activity and as a consequence thereof an excess degradation of the elastin of the alveolar cells [J. E. Gadek et al., *J. Clin. Invest.* 68, 889-898 (1981); Z. Werb et al., *J. Invest. Dermatol.* 79, 154-159 (1982); A. Janoff, *Am. Rev. Respir. Dis.* 132, 417-433 (1985); P. J. Barnes, *N. Engl. J. Med.* 343, 269-280 (2000)]. This tissue degradation causes the bronchii to collapse. This is associated with a reduced elasticity of the lung, which leads to obstructed breathing and impaired respiration. In addition, frequent and persistent inflammation of the lung may lead to remodeling of the bronchii and as a consequence to the formation of lesions. Such lesions contribute to the chronic cough which characterizes chronic bronchitis.

Alpha-1 antitrypsin (AAT) is a small endogenous protein and represents, as mentioned above, the most important endogenous elastase inhibitor. In patients having a genetic deficiency of this protein (AADT), the protease/antiprotease balance is shifted. Accordingly, in AADT patients, the effective radius and the duration of action of HNE is increased by a factor of 2.5 and 6.5, respectively [T. G. Liou and E. J. Campbell, *Biochemistry* 1995, 16171-16177]. AADT patients have an increased risk of developing pulmonary emphysema or COPD, and in many AADT patients a lung transplant is indicated.

Bronchiectasis is understood as an abnormal dilation of the bronchial tree. Two forms may be distinguished: sack-shaped localized bronchiectases and generalized, cylindrical bronchiectases. Bronchiectases may be congenital; however, in most cases they are acquired and are found in particular in smokers. Owing to the dilation, drainage of the bronchial secretions is rendered more difficult, and the retained bronchial secretions promote infections. Frequently, bronchiectases are also encountered in the case of congenital disorders of the mucosa such as mucoviscidosis with abnormal viscosity of the bronchial secretions and in the case of ciliary dyskinesia syndrome. In the case of this syndrome (Kartagener syndrome), the architecture and function of the cilia and thus drainage of the secretions are impaired. Other causes of bronchiectases may be obstructions proximal to the ectasis, for example by tumors or foreign bodies. Recurrent and persisting infections weakening the bronchial walls are also thought to be causal. Furthermore, there are bronchiectasias which can not be connected unambiguously to states of infection or exogenic noxa (idiopathic bronchiectasias).

Bronchiectasia is characterized by migration of neutrophils into the pulmonary tissue. The patients show a marked imbalance between neutrophilic activity and protective inhibitor proteins, resulting in damage to the pulmonary tissue by the proteases (mainly HNE) secreted by the neutrophils [Schaaf et al., *Respiration* 67, 52-59 (2000)].

Bronchiolitis obliterans is an inflammation of the bronchioli with destruction of the epithelium and formation of a fibrin-rich exudate in the bronchioli and the neighbouring alveoli. Organization of the exudate results in plugs of connective tissue reaching from the bronchioli into the alveoli. The disease is characterized by an increased number of neutrophils in the respiratory tract and an imbalance between free elastase and the endogenous elastase inhibitor protein [Elssner et al., *Transpl. Infect. Dis.* 3, 168-176 (2001)] Prior infections and medicaments are being discussed as possible causes. The disease may also occur in the context of a transplant rejection.

Acute lung injury (ALI) and the more pronounced form thereof, acute respiratory distress syndrome (ARDS), are serious disorders associated with a mortality of 50-60%. According to the definition of the North American-European Consensus Conference (NAECC) of 1994, ALI and ARDS are defined by an acute onset, bilateral radiologically visible infiltrates, a $PaO_2/FiO_2$ index of ≤300 mmHg (ALI) or ≤200 mmHg (ARDS), a pulmonary capillary wedge pressure of <18 mmHg and no clinical evidence of left atrial hypertension.

The development of acute lung injury may be preceded both by pulmonary and extrapulmonary disorders. Aspiration of stomach content, pneumonias, smoke poisoning, pulmonary contusion and near-drowning are considered to be lung-specific predisposing factors. In particular the aspiration of stomach content and pneumonias are frequently seen as initial disorders of ALI/ARDS of pulmonary origin. The most frequent indirect events are polytrauma, sepsis, repeated blood transfusions, acute pancreatitis and burns. The incidence is 17.9 cases of ALI and 13.5 cases of ARDS per 100 000 inhabitants and year [Luhr et al., *Am. J. Respir. Crit. Care Med.* 159, 1849-1861 (1999)].

A central role in the development of these disorders is played by the massive inflammatory changes in the lung, which are triggered by a widely branched system of mediators. An important role in the development of lung injury is also played by neutrophilic granulocytes, the number of which increases permanently during the inflammatory process [Chollet-Martin et al., *Am. J. Respir. Crit. Care Med.* 154, 594-601 (1996)]. The action of the mediators causes damage to the alveolocapillary membranes, and this results in an increased permeability of the alveolar capillary barrier. Owing to the increased permeability, protein-rich fluid can permeate into the alveolae and also into the interstitial space; a low-pressure pulmonary edema develops. Characteristic for ALI/ARDS, this is a noncardiogenic edema. The edema fluid contains mainly fibrin, erythrocytes, leukocytes, hyaline membranes and other proteins. Together with the products of activated neutrophils, the protein-rich exudate leads to dysfunction of the surfactant. The inflammatory processes cause damage and loss of pneumocytes of type II, which form surfactant, resulting in a reduced surfactant production. The surfactant deficit increases the surface tension in the alveolae; the alveolae collapse and atelectases are formed. With perfusion being maintained, there is thus a ventilation/perfusion imbalance resulting in an increase of the pulmonary right-left shunt. Furthermore, compliance is reduced, and in contrast the alveolar dead space is increased because there are areas which are ventilated but, owing to pulmonary hypertension, no longer sufficiently perfused.

An increased elastase activity, which correlates to the severity of the lung injury, could be measured in the bronchoalveolar lavage fluid (BALF) of ARDS patients. In animal models where the lung is injured (for example by administration of LPS), this effect can be reproduced. Here, treatment with elastase inhibitors (for example sivelestat or elafin, vide infra,) reduces the elastase activity in the BALF considerably and improves lung function.

In Japan and South Korea, an elastase inhibitor (sivelestat, Elaspol®) is approved for the treatment of acute lung injury associated with SIRS. The reversible, but reactive compound has only a relatively weak effect on HNE ($K_i$ 200 nM) and also acts on the pancreas elastase ($IC_{50}$ 5.6 µM). The active compound is administered intravenously, oral administration is not possible.

Elafin and structural analogs are also investigated as therapeutically useful elastase inhibitors. Elafin is an endogenous small protein which inhibits both elastase and proteinase 3. However, owing to the proteinergic character, oral administration of elafin is not possible.

It is an object of the present invention to provide novel substances acting as low-molecular-weight, non-reactive and selective inhibitors of human neutrophil elastase (HNE), which are suitable as such for the treatment and/or prevention in particular of pulmonary disorders and disorders of the cardiovascular system.

WO 2004/024700, WO 2004/024701, WO 2005/082863 and WO 2005/082864 disclose various 1,4-diaryldihydropyrimidin-2-one derivatives as HNE inhibitors for the treatment of chronic obstructive pulmonary disease, acute coronary syndrome, myocardial infarction and heart failure. Di- and multimers of such compounds for the treatment of respiratory disorders are claimed in WO 2006/082412, WO 2006/136857 and WO 2007/042815. WO 2008/003412 discloses the use of certain 1,4-diaryldihydropyrimidin-2-one derivatives for treating pulmonary arterial hypertension. 4-Aryldihydropyrimidin-2-one derivatives as inhibitors of the calcium channel function for the treatment of hypertension are described in WO 2005/009392.

It has now been found that certain 1,4-diaryldihydropyrimidin-2-one derivatives are particularly suitable for the treatment and/or prevention of disorders. These compounds described below are low-molecular-weight, non-reactive and selective inhibitors of human neutrophil elastase (HNE) which, surprisingly, effect a considerably stronger inhibition of this protease than the compounds known from the prior art. In addition, the compounds according to the invention have an unexpectedly low in vitro clearance with respect to hepatocytes and thus have improved metabolic stability. Moreover, some of the compounds according to the invention have good solubility in aqueous systems which is advantageous with regard to their formulatibility and/or intravenous administrability. Accordingly, the substances of the present invention are promising starting points for novel medicaments for the treatment and/or prevention of in particular disorders of the lung and the cardiovascular system.

Specifically, the present invention relates to compounds of the general formula (I)

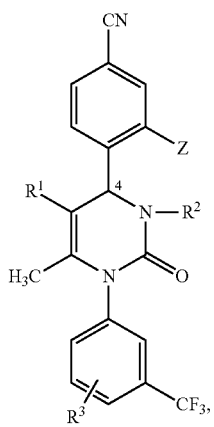

(I)

in which
Z represents a sulfonamide grouping of the formula

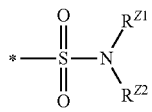

or represents a sulfoximine grouping of the formula

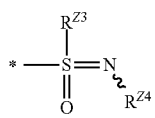

in which
* denotes the point of attachment to the phenyl ring,
$R^{Z1}$ represents hydrogen, or represents $(C_1-C_6)$-alkyl which may be substituted by hydroxyl, $(C_1-C_4)$-alkoxy, amino, mono- or di-$(C_1-C_4)$-alkylamino and up to three times by fluorine,
$R^{Z2}$ represents hydrogen, $(C_3-C_6)$-cycloalkyl, 4- to 6-membered heterocyclyl or 5- or 6-membered heteroaryl
or
represents $(C_1-C_6)$-alkyl which may be substituted by hydroxyl, $(C_1-C_4)$-alkoxy, amino, mono- or di-$(C_1-C_4)$-alkylamino, $(C_1-C_4)$-alkylcarbonylamino, $(C_1-C_4)$-alkoxycarbonylamino, $(C_1-C_4)$-alkylsulfinyl,
$(C_1-C_4)$-alkylsulfonyl, $(C_3-C_6)$-cycloalkyl, phenyl, 4- to 6-membered heterocyclyl, 5- or 6-membered heteroaryl or a group of the formula —C(=O)—$NR^{Z5}R^{Z6}$ and up to three times by fluorine,
where the alkoxy substituent mentioned for its part may be substituted up to three times by fluorine,
and where
the heterocyclyl groups mentioned may be substituted up to two times by identical or different substituents from the group consisting of fluorine, $(C_1-C_4)$-alkyl, oxo, hydroxyl, $(C_1-C_4)$-alkoxy, amino, mono- and di-$(C_1-C_4)$-alkylamino
and
the phenyl group mentioned and the heteroaryl groups mentioned may be substituted up to two times by identical or different substituents from the group consisting of fluorine, chlorine, cyano, $(C_1-C_4)$-alkyl, difluoromethyl, trifluoromethyl and $(C_1-C_4)$-alkoxy,
and where
$R^{Z5}$ and $R^{Z6}$ are identical or different and independently of one another represent hydrogen or $(C_1-C_4)$-alkyl
or
$R^{Z5}$ and $R^{Z6}$ together with the nitrogen atom to which they are attached form a 4- to 6-membered aza heterocycle which may contain a further ring heteroatom from the group consisting of N, O and S and may be substituted by $(C_1-C_4)$-alkyl, oxo, hydroxyl, $(C_1-C_4)$-alkoxy, amino, mono- or di-$(C_1-C_4)$-alkylamino,
or
$R^{Z1}$ and $R^{Z2}$ together with the nitrogen atom to which they are attached form a 4- to 10-membered aza heterocycle which may contain a further ring heteroatom from the group consisting of N, O and S and may be substituted up to two times by identical or different substituents from the group consisting of fluorine, $(C_1-C_4)$-alkyl, oxo, hydroxyl, $(C_1-C_4)$-alkoxy, amino, mono- and di-$(C_1-C_4)$-alkylamino,
$R^{Z3}$ represents $(C_1-C_6)$-alkyl which may be substituted by $(C_3-C_6)$-cycloalkyl or up to three times by fluorine, or represents phenyl which may be substituted up to two times by identical or different substituents from the group consisting of fluorine, chlorine, cyano, $(C_1-C_4)$-alkyl, difluoromethyl and trifluoromethyl, or represents $(C_3-C_6)$-cycloalkyl,
and
$R^{Z4}$ represents hydrogen, $(C_1-C_4)$-alkyl or $(C_3-C_6)$-cycloalkyl,
$R^1$ represents cyano or acetyl,
$R^2$ represents hydrogen, represents $(C_1-C_4)$-alkyl or $(C_1-C_4)$-alkylsulfonyl which may be substituted up to three times by fluorine, or represents a group of the formula —$CH_2$—C(=O)—NH—$R^4$ in which
$R^4$ represents hydrogen, represents $(C_1-C_4)$-alkyl which may be substituted by $(C_3-C_6)$-cycloalkyl or up to three times by fluorine, or represents $(C_3-C_6)$-cycloalkyl,
and
$R^5$ represents hydrogen, fluorine or chlorine,
and their salts, solvates and solvates of the salts.

Compounds according to the invention are the compounds of the formula (I) and the salts, solvates and solvates of the salts thereof, the compounds of the formulae mentioned hereinafter and encompassed by formula (I) and the salts, solvates and solvates of the salts thereof, and the compounds which are mentioned hereinafter as exemplary embodiments and encompassed by formula (I) and the salts, solvates and solvates of the salts thereof, insofar as the compounds encompassed by formula (I) and mentioned hereinafter are not already salts, solvates and solvates of the salts.

The compounds according to the invention may, depending on their structure, exist in various stereoisomeric forms, i.e. in the form of configurational isomers or, if appropriate, also in the form of conformational isomers (enantiomers and/or diastereomers, including those in the case of atropisomers). The present invention therefore embraces the enantiomers and diastereomers and also their respective mixtures. The stereoisomerically pure constituents can be isolated in a known manner from such mixtures of enantiomers and/or diastereomers.

If the compounds according to the invention may occur in tautomeric forms, the present invention encompasses all tautomeric forms.

Salts which are preferred for the purposes of the present invention are physiologically acceptable salts of the compounds according to the invention. Also encompassed are salts which are themselves unsuitable for pharmaceutical uses but can be used for example for isolating or purifying the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds according to the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds according to the invention (for example by metabolism or hydrolysis).

In the context of the present invention, the substituents have the following meaning, unless specified otherwise:

$(C_1-C_6)$-Alkyl and $(C_1-C_4)$-alkyl stand for the purposes of the invention for a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, isobutyl, sec-butyl, tert-butyl, 1-ethylpropyl, n-pentyl, neopentyl and n-hexyl.

$(C_1-C_4)$-Alkylcarbonyl stands for the purposes of the invention for a straight-chain or branched alkyl radical which has 1 to 4 carbon atoms and is attached via a carbonyl group. Examples which may be preferably mentioned are: acetyl, propionyl, n-butyryl, isobutyryl, n-pentanoyl and pivaloyl.

$(C_1-C_4)$-Alkoxy stands for the purposes of the invention for a straight-chain or branched alkoxy radical having 1 to 4 carbon atoms. Examples which may be preferably mentioned are: methoxy, ethoxy, n-propoxy, isopropoxy, n-butoxy and tert-butoxy.

$(C_1-C_4)$-Alkoxycarbonyl stands for the purposes of the invention for a straight-chain or branched alkoxy radical having 1 to 4 carbon atoms which is attached via a carbonyl group. Examples which may be preferably mentioned are: methoxycarbonyl, ethoxycarbonyl, n-propoxycarbonyl, isopropoxycarbonyl, n-butoxycarbonyl and tert-butoxycarbonyl.

Mono-$(C_1-C_4)$-alkylamino stands for the purposes of the invention for an amino group having a straight-chain or branched alkyl substituent having 1 to 4 carbon atoms. Examples which may be preferably mentioned are: methylamino, ethylamino, n-propylamino, isopropylamino, n-butylamino and tert-butylamino.

Di-$(C_1-C_4)$-alkylamino stands for the purposes of the invention for an amino group having two identical or different straight-chain or branched alkyl substituents having in each case 1 to 4 carbon atoms. Examples which may be preferably mentioned are: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino and N-tert-butyl-N-methylamino.

$(C_1-C_4)$-Alkylcarbonylamino stands for the purposes of the invention for an amino group having a straight-chain or branched alkylcarbonyl substituent which has 1 to 4 carbon atoms in the alkyl radical and is attached via the carbonyl group to the nitrogen atom. Examples which may be preferably mentioned are: acetylamino, propionylamino, n-butyrylamino, isobutyrylamino, n-pentanoylamino and pivaloylamino.

$(C_1-C_4)$-Alkoxycarbonylamino stands for the purposes of the invention for an amino group having a straight-chain or branched alkoxycarbonyl substituent which has 1 to 4 carbon atoms in the alkoxy radical and is attached via the carbonyl group to the nitrogen atom. Examples which may be preferably mentioned are: methoxycarbonylamino, ethoxycarbonylamino, n-propoxycarbonylamino, isopropoxycarbonylamino, n-butoxycarbonylamino and tert-butoxycarbonylamino.

$(C_1-C_4)$-Alkylsulfinyl stands for the purposes of the invention for a straight-chain or branched alkyl radical which has 1 to 4 carbon atoms and is attached via a sulfinyl group [—S(=O)—]. Examples which may be preferably mentioned are: methylsulfinyl, ethylsulfinyl, n-propylsulfinyl, isopropylsulfinyl, n-butylsulfinyl and tert-butylsulfinyl.

$(C_1-C_4)$-Alkylsulfonyl stands for the purposes of the invention for a straight-chain or branched alkyl radical which has 1 to 4 carbon atoms and is attached via a sulfonyl group [—S(=O)$_2$—]. Examples which may be preferably mentioned are: methylsulfonyl, ethylsulfonyl, n-propylsulfonyl, isopropylsulfonyl, n-butylsulfonyl and tert-butylsulfonyl.

$(C_3-C_6)$-Cycloalkyl stands for the purposes of the invention for a monocyclic saturated cycloalkyl group having 3 to 6 ring carbon atoms. Examples which may be preferably mentioned are: cyclopropyl, cyclobutyl, cyclopentyl and cyclohexyl.

A 4- to 10-membered aza heterocycle stands for the purposes of the invention for a mono- or optionally bicyclic saturated heterocycle which has a total of 4 to 10 ring atoms, which contains a ring nitrogen atom through which it is also attached, and which may additionally contain a further ring heteroatom from the group consisting of N, O and S. Examples which may be preferably mentioned are: azetidinyl, pyrrolidinyl, pyrazolidinyl, 1,3-oxazolidinyl, 1,3-thiazolidinyl, piperidinyl, piperazinyl, morpholinyl, thiomorpholinyl, hexahydroazepinyl, hexahydro-1,4-diazepinyl, octahydroazocinyl, octahydropyrrolo[3,4-b]pyrrolyl, octahydroindolyl, octahydroisoindolyl, octahydropyrrolo[3,2-b]pyridyl, octahydropyrrolo[3,4-b]pyridyl, octahydropyrrolo[3,4-c]pyridyl, octahydropyrrolo[1,2-a]pyrazinyl, decahydroquinolinyl, decahydroisoquinolinyl, octahydropyrido[1,2-a]pyrazinyl, 7-azabicyclo[2.2.1]heptyl, 3-azabicyclo[3.2.0]heptyl, 3-azabicyclo[3.2.1]octyl, 8-azabicyclo[3.2.1]octyl, 8-oxa-3-azabicyclo[3.2.1]octyl and 9-azabicyclo[3.3.1]nonyl. Preference is given to a mono- or optionally bicyclic 5- to 10-membered aza heterocycle which may, in addition to the nitrogen atom, contain a further ring heteroatom from the group consisting of N and O, such as, for example, pyrrolidinyl, pyrazolidinyl, 1,3-oxazolidinyl, piperidinyl, piperazinyl, morpholinyl, hexahydroazepinyl, hexahydro-1,4-diazepinyl, octahydroazocinyl, octahydropyrrolo[3,4-b]-pyrrolyl, octahydroindolyl, octahydroisoindolyl, octahydropyrrolo[3,2-b]pyridyl, octahydropyrrolo[3,4-b]pyridyl, octahydropyrrolo[3,4-c]pyridyl, octahydropyrrolo[1,2-a]pyrazinyl, decahydroquinolinyl, decahydroisoquinolinyl, octahydropyrido[1,2-a]pyrazinyl, 7-azabicyclo[2.2.1]heptyl, 3-azabicyclo[3.2.0]heptyl, 3-Aazabicyclo[3.2.1]octyl, 8-azabicyclo[3.2.1]-octyl, 8-oxa-3-azabicyclo[3.2.1]octyl and 9-azabicyclo[3.3.1]nonyl. Particular preference is given to a monocyclic 5- or 6-membered aza heterocycle which may, in addition to the nitrogen atom, contain a further ring heteroatom from the group consisting of N and O, such as, for example, pyrrolidinyl, 1,3-oxazolidinyl, piperidinyl, piperazinyl and morpholinyl.

4- to 6-membered heterocyclyl stands for the purposes of the invention for a monocyclic saturated heterocycle which has a total of 4 to 6 ring atoms, which contains one or two ring heteroatoms from the group consisting of N, O and S and which is attached via a ring carbon atom or optionally a ring nitrogen atom. Examples which may be mentioned are: azetidinyl, oxetanyl, pyrrolidinyl, pyrazolidinyl, tetrahydrofuranyl, 1,3-oxazolidinyl, thiolanyl, 1,3-thiazolidinyl, piperidinyl, piperazinyl, tetrahydropyranyl, 1,4-dioxanyl, tetrahydrothiopyranyl, morpholinyl and thiomorpholinyl. Preference is given to a 4- to 6-membered heterocycle having one or two ring heteroatoms from the group consisting of N and O, such as, for example, azetidinyl, oxetanyl, pyrrolidinyl, tetrahydrofuranyl, piperidinyl, piperazinyl, tetrahydropyranyl, 1,4-dioxanyl and morpholinyl. Particular preference is given to a 5- or 6-membered heterocycle having one or two ring heteroatoms from the group consisting of N and O, such as, for example, pyrrolidinyl, tetrahydrofuranyl, piperidinyl, piperazinyl, tetrahydropyranyl, 1,4-dioxanyl and morpholinyl.

5- or 6-membered heteroaryl stands for the purposes of the invention for an aromatic heterocycle (heteroaromatic) having a total of 5 or 6 ring atoms which contains up to three identical or different ring heteroatoms from the group consisting of N, O and S and which is attached via a ring carbon atom or, if appropriate, via a ring nitrogen atom. Examples which may be mentioned are: furyl, pyrrolyl, thienyl, pyrazolyl, imidazolyl, oxazolyl, thiazolyl, isoxazolyl, isothiazolyl, triazolyl, oxadiazolyl, thiadiazolyl, pyridyl, pyrimidinyl, pyridazinyl, pyrazinyl and triazinyl. Preference is given to 5- or 6-membered heteroaryl radicals having one or two ring heteroatoms from the group consisting of N, O and S, such as, for example, furyl, pyrrolyl, thienyl, pyrazolyl, imidazolyl, oxazolyl, thiazolyl, isoxazolyl, isothiazolyl, pyridyl, pyrimidinyl, pyridazinyl and pyrazinyl.

For the purposes of the invention, an oxo substituent is an oxygen atom which is attached via a double bond to a carbon atom.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one or two identical or different substituents. Very particularly preferred is substitution by one substituent.

Preferred for the purposes of the present invention are compounds of the formula (I) in which Z represents a sulfonamide grouping of the formula

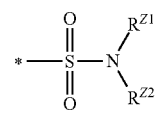

or represents a sulfoximine grouping of the formula

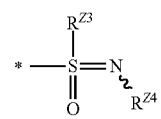

in which

* denotes the point of attachment to the phenyl ring, $R^{Z1}$ represents hydrogen or represents $(C_1-C_4)$-alkyl which may be substituted by hydroxyl, methoxy or ethoxy, $R^{Z2}$ represents hydrogen, $(C_3-C_6)$-cycloalkyl, 5- or 6-membered heterocyclyl or 5- or 6-membered heteroaryl or represents $(C_1-C_4)$-alkyl which may be substituted by hydroxyl, $(C_1-C_4)$-alkoxy, amino, mono- or di-$(C_1-C_4)$-alkylamino, $(C_1-C_4)$-alkylcarbonylamino, $(C_1-C_4)$-alkoxycarbonylamino, $(C_1-C_4)$-alkylsulfinyl, $(C_1-C_4)$-alkylsulfonyl, $(C_3-C_6)$-cycloalkyl, phenyl, 5- or 6-membered heterocyclyl, 5- or 6-membered heteroaryl or a group of the formula —C(=O)—$NR^{Z5}R^{Z6}$ and up to three times by fluorine, where the alkoxy substituent mentioned for its part may be substituted up to three times by fluorine, and where the heterocyclyl groups mentioned may be substituted up to two times by identical or different substituents from the group consisting of $(C_1-C_4)$-alkyl, oxo, hydroxyl and $(C_1-C_4)$-alkoxy and the phenyl group mentioned and the heteroaryl groups mentioned may be substituted up to two times by identical or different substituents from the group consisting of fluorine, chlorine, cyano, $(C_1-C_4)$-alkyl, trifluoromethyl and $(C_1-C_4)$-alkoxy, and where $R^{Z5}$ and $R^{Z6}$ are identical or different and independently of one another represent hydrogen or $(C_1-C_4)$-alkyl or R$^{Z5}$ and R$^{Z6}$ together with the nitrogen atom to which they are attached form a 5- or 6-membered aza heterocycle which may contain a further ring heteroatom from the group consisting of N and O and may be substituted by (C$_1$-C$_4$)-alkyl, oxo, hydroxyl or (C$_1$-C$_4$)-alkoxy, or R$^{Z1}$ and R$^{Z2}$ together with the nitrogen atom to which they are attached form a 5- to 10-membered aza heterocycle which may contain a further ring heteroatom from the group consisting of N and O and may be substituted up to two times by identical or different substituents from the group consisting of (C$_1$-C$_4$)-alkyl, oxo, hydroxyl and (C$_1$-C$_4$)-alkoxy, R$^{Z3}$ represents (C$_1$-C$_4$)-alkyl which may be substituted by (C$_3$-C$_6$)-cycloalkyl or up to three times by fluorine, or represents phenyl which may be substituted up to two times by identical or different substituents from the group consisting of fluorine, chlorine, cyano, methyl and trifluoromethyl, or represents (C$_3$-C$_6$)-cycloalkyl, and R$^{Z4}$ represents hydrogen, methyl or cyclopropyl, R$^1$ represents cyano, R$^2$ represents hydrogen, (C$_1$-C$_4$)-alkyl or (C$_1$-C$_4$)-alkylsulfonyl, each of which may be substituted up to three times by fluorine, or represents a group of the formula —CH$_2$—C(=O)—NH—R$^4$ in which R$^4$ represents hydrogen, methyl, cyclopropyl or cyclopropylmethyl, and R$^3$ represents hydrogen or fluorine, and their salts, solvates and solvates of the salts.

Particular preference in the context of the present invention is given to compounds of the formula (I) in which Z represents a sulfonamide grouping of the formula

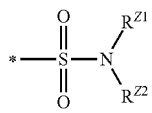

in which

* denotes the point of attachment to the phenyl ring,

R$^{Z1}$ represents hydrogen, methyl or 2-hydroxyethyl,

R$^{Z2}$ represents hydrogen, cyclopropyl, 5- or 6-membered heterocyclyl or 5- or 6-membered heteroaryl or represents (C$_1$-C$_4$)-alkyl which may be substituted by hydroxyl, methoxy, ethoxy, amino, methylamino, ethylamino, dimethylamino, diethylamino, acetylamino, cyclopropyl, 5- or 6-membered heterocyclyl or a group of the formula —C(=O)—NR$^{Z5}$R$^{Z6}$, where methoxy and ethoxy substituents mentioned for their part may be substituted up to three times by fluorine, and where the heterocyclyl groups mentioned may be substituted up to two times by identical or different substituents from the group consisting of methyl, ethyl, oxo, hydroxyl, methoxy and ethoxy and the heteroaryl group mentioned may be substituted up to two times by identical or different substituents from the group consisting of fluorine, chlorine, cyano, methyl, ethyl, trifluoromethyl, methoxy and ethoxy, and where R$^{Z5}$ and R$^{Z6}$ independently of one another represent hydrogen or methyl or together with the nitrogen atom to which they are attached form a pyrrolidine, piperidine or morpholine ring, or R$^{Z1}$ and R$^{Z2}$ together with the nitrogen atom to which they are attached form a pyrrolidine, piperidine or morpholine ring, R$^1$ represents cyano, R$^2$ represents hydrogen, methyl, methylsulfonyl or the group of the formula —CH$_2$—C(=O)—NH$_2$, and R$^3$ represents hydrogen, and their salts, solvates and solvates of the salts.

Particular preference in the context of the present invention is also given to compounds of the formula (I) in which Z represents a sulfoximine grouping of the formula

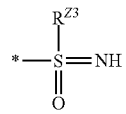

in which

* denotes the point of attachment to the phenyl ring and

R$^{Z3}$ represents (C$_1$-C$_4$)-alkyl which may be substituted by cyclopropyl or up to three times by fluorine, or represents cyclopropyl, R$^1$ represents cyano, R$^2$ represents hydrogen, methyl, methylsulfonyl or the group of the formula —CH$_2$—C(=O)—NH$_2$, and R$^3$ represents hydrogen, and their salts, solvates and solvates of the salts.

Very particular preference in the context of the present invention is given to compounds of the formula (I) in which Z represents a sulfonamide grouping of the formula

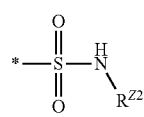

in which

* denotes the point of attachment to the phenyl ring and

R$^{Z2}$ represents hydrogen, methyl or the group of the formula —CH$_2$—C(=O)—NH$_2$, R$^1$ represents cyano, R$^2$ represents hydrogen, methyl or methylsulfonyl, and R$^3$ represents hydrogen, and their salts, solvates and solvates of the salts.

Very particular preference in the context of the present invention is also given to compounds of the formula (I) in which Z represents a sulfoximine grouping of the formula

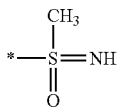

in which
* denotes the point of attachment to the phenyl ring,
$R^1$ represents cyano,
$R^2$ represents hydrogen, methyl or methylsulfonyl,
and
$R^3$ represents hydrogen,
and their salts, solvates and solvates of the salts.

Of particular importance are compounds of the formula (I) having the S configuration, shown in formula (I-ent), at the 4-position of the dihydropyrimidinone ring

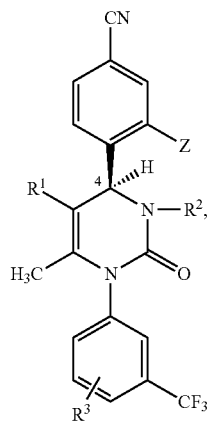

(I-ent)

where Z, $R^1$, $R^2$ and $R^3$ each have the meanings given above, and their salts, solvates and solvates of the salts.

Specific radical definitions given in the respective combinations or preferred combinations of radicals are, independently of the combinations of radicals given in each case, also replaced by any radical definitions of other combinations.

Very particular preference is given to combinations of two or more of the preferred ranges mentioned above.

The invention furthermore provides a process for preparing the compounds of the formula (I) according to the invention in which
Z represents a sulfonamide grouping of the formula

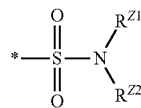

in which
* denotes the point of attachment to the phenyl ring
and
$R^{Z1}$ and $R^{Z2}$ have the meanings given above,
characterized in that initially an aniline derivative of the formula (II)

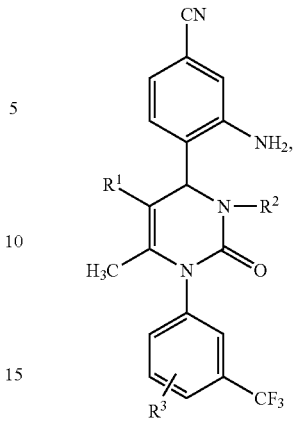

(II)

in which $R^1$, $R^2$ and $R^3$ have the meanings given above, is converted with sodium nitrite and hydrochloric acid into the corresponding diazonium salt and then reacted in a one-pot reaction with sulfur dioxide in the presence of copper(I) chloride to give a sulfonyl chloride of the formula (III)

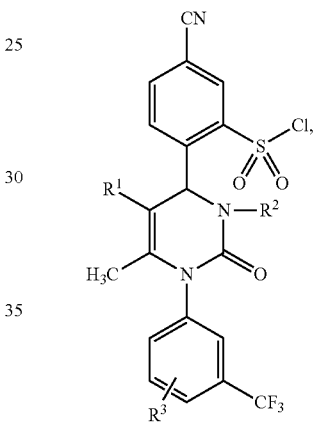

(III)

in which $R^1$, $R^2$ and $R^3$ have the meanings given above, and this is then reacted with an amine of the formula (IV)

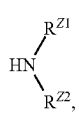

(IV)

in which $R^{Z1}$ and $R^{Z2}$ have the meanings given above, if appropriate in the presence of an auxiliary base, to give the sulfonamide of the formula (I-A)

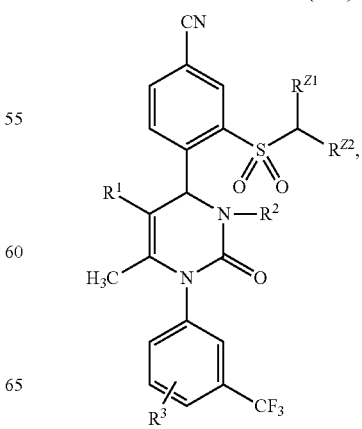

(I-A)

in which R¹, R², R³, R^{Z1} and R^{Z2} have the meanings given above,
and the compounds of the formula (I-A) obtained in this manner are, if appropriate, separated by methods known to the person skilled in the art into their enantiomers and/or diastereomers and/or converted with the appropriate (i) solvents and/or (ii) bases or acids into their solvates, salts and/or solvates of the salts.

The diazotization and the subsequent sulfochlorination in process step (II)→(III) are carried out by methods familiar to the person skilled in the art by initially converting the aniline derivative of the formula (II) by reaction with sodium nitrite in aqueous hydrochloric acid at from −20° C. to 0° C. into the diazonium salt which is then reacted further in situ at from −20° C. to +20° C. with a saturated solution of sulfur dioxide in acetic acid in the presence of copper(I) chloride as catalyst.

Inert solvents for the sulfonamide formation in process step (III)+(IV)→(I-A) are customary organic solvents which do not change under the reaction conditions. These include, for example, ethers such as diethyl ether, diisopropyl ether, methyl tert-butyl ether, 1,2-dimethoxyethane, 1,4-dioxane or tetrahydrofuran, hydrocarbons such as pentane, hexane, cyclohexane, benzene, toluene or xylene, halogenated hydrocarbons such as dichloromethane, 1,2-dichloroethane, trichloromethane or chlorobenzene, or other solvents such as ethyl acetate, acetonitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using tetrahydrofuran, 1,4-dioxane, dichloromethane or 1,2-dichloroethane.

The reaction (III)+(IV)→(I-A) is usually carried out in the presence of an auxiliary base. Suitable for this purpose are in particular tertiary organic amine bases such as triethylamine, N,N-diisopropylethylamine, N-methylmorpholine, N-methylpiperidine, 1,5-diazabicyclo[4.3.0]non-5-ene (DBN), 1,8-diazabicyclo[5.4.0]undec-7-ene (DBU), pyridine or 4-N,N-dimethylaminopyridine; preference is given to using triethylamine or N,N-diisopropylethylamine. If appropriate, the reaction can also be carried out using an excess of the amine (IV), without further addition of an auxiliary base.

The process step (III)+(IV)→(I-A) is generally carried out in a temperature range of from −20° C. to +60° C., preferably at from 0° C. to +40° C. The reaction can be carried out at atmospheric, at elevated or at reduced pressure (for example at from 0.5 to 5 bar); in general, the reaction is carried out at atmospheric pressure.

The invention furthermore provides a process for preparing compounds of the formula (I) according to the invention in which
Z represents a sulfoximine grouping of the formula

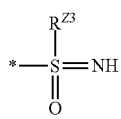

in which
* denotes the point of attachment to the phenyl ring and
R^{Z3} has the meaning given above,
characterized in that a phenyl thioether derivative of the formula (V)

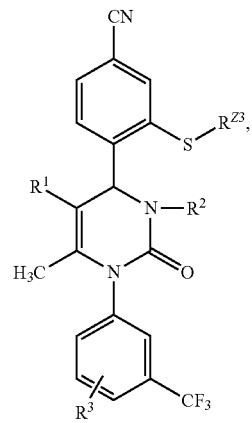

(V)

in which R¹, R², R³ and R^{Z3} have the meanings given above, is initially oxidized with hydrogen peroxide, a peracid or a periodate to give the sulfoxide of the formula (VI)

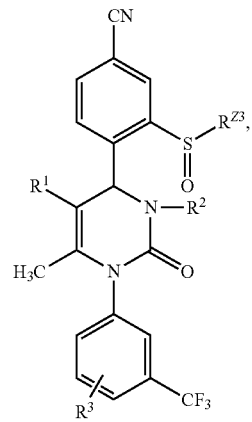

(VI)

in which R¹, R², R³ and R^{Z3} have the meanings given above, then converted with 2,2,2-trifluoroacetamide and (diacetoxyiodo)benzene in the presence of dimeric rhodium(II) acetate as catalyst and magnesium oxide as base into an N-acylsulfoximine of the formula (VII)

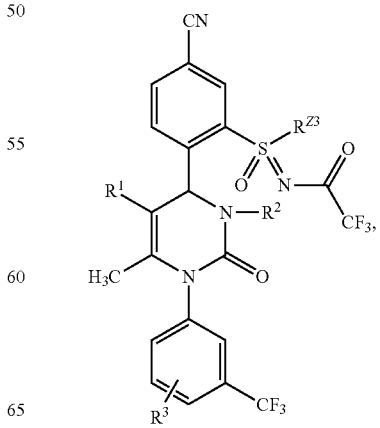

(VII)

in which $R^1$, $R^2$, $R^3$ and $R^{Z3}$ have the meanings given above, and the trifluoroacetyl group in (VII) is then removed under basic conditions to give the sulfoximine of the formula (I-B)

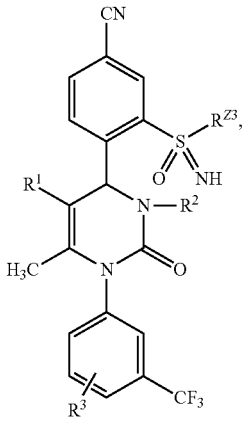

(I-B)

in which $R^1$, $R^2$, $R^3$ and $R^{Z3}$ have the meanings given above, and the compounds of the formula (I-B) obtained in this manner are, if appropriate, separated by methods known to the person skilled in the art into their enantiomers and/or diastereomers and/or converted with the appropriate (i) solvents and/or (ii) bases or acids into their solvates, salts and/or solvates of the salts.

Suitable oxidizing agents for the process step (V)→(VI) are in particular organic or inorganic peroxo compounds. These include, for example, hydrogen peroxide, if appropriate with catalyst assistance, peracids such as peracetic acid or m-chloroperbenzoic acid, or salts of such compounds, such as sodium periodate. Preference is given to using hydrogen peroxide, in the presence of the catalyst methyltrioxorhenium, or sodium periodate.

The oxidation (V)→(VI) is preferably carried out in alcoholic solvents such as methanol or ethanol, if appropriate with addition of water, in a temperature range of from –20° C. to +100° C., preferably at from 0° C. to +60° C.

The transformation of the sulfoxide (VI) into the N-trifluoroacetylsulfoximine (VII) is carried out in accordance with a method described in the literature via a metal-catalyzed oxidative imination reaction with 2,2,2-trifluoroacetamide and (diacetoxyiodo)benzene in the presence of dimeric rhodium (II) acetate as catalyst and magnesium oxide as base [cf. H. Okamura and C. Bolm, *Org. Lett.* 6 (8), 1305-1307 (2004)]. The reaction is preferably carried out in the solvent dichloromethane in a temperature range of from 0° C. to +40° C.

The removal of the trifluoroacetyl group in process step (VII)→(I-B) is effected in a customary manner by treatment with an alkali metal carbonate or hydroxide in an alcoholic or aqueous solvent. Preference is given to using potassium carbonate in methanol or acetonitrile/methanol mixtures. The reaction is generally carried out in a temperature range of from –10° C. to +30° C.

Sulfoximine derivatives of the formula (I-C) according to the invention

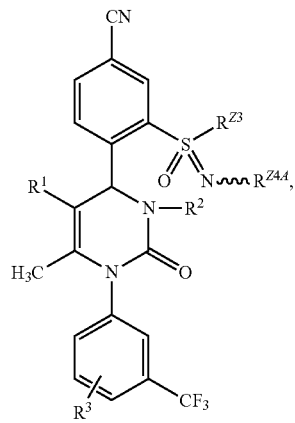

(I-C)

in which $R^1$, $R^2$, $R^3$ and $R^{Z3}$ have the meanings given above and
$R^{Z4A}$ represents $(C_1-C_4)$-alkyl or $(C_3-C_6)$-cycloalkyl,
can be obtained by reaction of the compounds (I-B) described above with a compound of the formula (VIII)

$$R^{Z4A}-X^1 \quad (VIII),$$

in which $R^{Z4A}$ has the meaning given above
and
$X^1$ represents a leaving group such as, for example, halogen, mesylate, tosylate or triflate,
in the presence of a strong base such as, for example, sodium tert-butoxide or potassium tert-butoxide or sodium hydride or potassium hydride. If appropriate, the use of a phase-transfer catalyst such as tetrabutylammonium bromide or benzyltriethylammonium chloride may be advantageous [cf., for example, C. R. Johnson and O. M. Layergne, *J. Org. Chem.* 58 (7), 1922-1923 (1993)].

The compounds of the formula (II) can be prepared analogously to processes described in the literature, for example by condensing 4-cyano-2-nitrobenzaldehyde of the formula (IX)

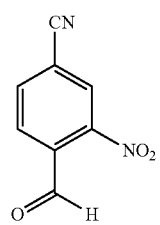

(IX)

in the presence of an acid or an acid anhydride in a 3-component one-pot reaction or sequentially with a keto compound of the formula (X)

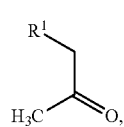

(X)

in which $R^1$ has the meaning given above, and a phenylurea derivative of the formula (XI)

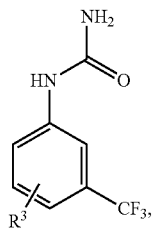

in which $R^3$ has the meaning given above,
to give a compound of the formula (XII-A)

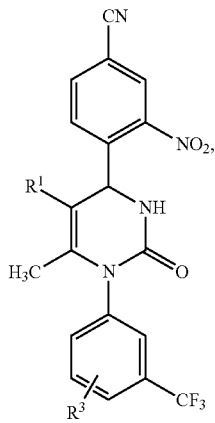

in which $R^1$ and $R^3$ have the meanings given above,
which is then, if the radical $R^2$ in formula (I) does not represent hydrogen, reacted in the presence of a base with a compound of the formula (XIII)

$$R^{2A}-X^2 \quad \text{(XIII),}$$

in which
$R^{2A}$ has the meaning of $R^2$ given above, but does not represent hydrogen,
and
$X^2$ represents a leaving group such as, for example, halogen, mesylate, tosylate or triflate, to give a compound of the formula (XII-B)

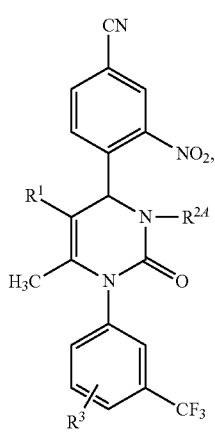

in which $R^1$, $R^{2A}$ and $R^3$ have the meanings given above, and the nitro compound of the formula (XII-A) or (XII-B) is then reduced to the aniline derivative of the formula (II)

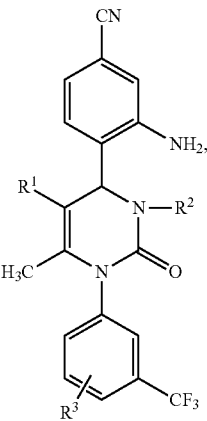

in which $R^1$, $R^2$ and $R^3$ have the meanings given above.

Suitable solvents for the process step (IX)+(X)+(XI)→(XII-A) are customary organic solvents which do not change under the reaction conditions. These include, for example, ethers, such as diethyl ether, diisopropyl ether, methyl tert-butyl ether, 1,2-dimethoxyethane, 1,4-dioxane or tetrahydrofuran, alcohols, such as methanol, ethanol, n-propanol, isopropanol, n-butanol or tertbutanol, hydrocarbons, such as pentane, hexane, cyclohexane, benzene, toluene or xylene, halogenated hydrocarbons, such as dichloromethane, 1,2-dichloroethan, trichloromethane or chlorobenzene, or other solvents, such as ethyl acetate, acetonitrile, dimethyl sulfoxide or N,N-dimethylformamide. It is also possible to use mixtures of the solvents mentioned. Preference is given to using methyl tert-butyl ether, tetrahydrofuran or 1,4-dioxane.

Suitable acids for the process step (IX)+(X)+(XI)→(XII-A) are customary inorganic or organic acids or acid anhydrides. These preferably include carboxylic acids, such as, for example, acetic acid or trifluoroacetic acid, sulfonic acids, such as methanesulfonic acid, trifluoromethanesulfonic acid or p-toluenesulfonic acid, hydrochloric acid, sulfuric acid, phosphoric acid, phosphonic acids, or phosphoric or phosphonic anhydrides or esters, such as polyphosphoric acid, phosphoric acid triethyl ester, polyphosphoric acid ethyl ester, phosphorus pentoxide or propanephosphonic anhydride. Preference is given to using phosphoric acid triethyl ester in combination with phosphorus pentoxide. The acid is generally employed in an amount of from 0.25 mol to 100 mol based on 1 mol of the compound (X).

The process step (IX)+(X)+(XI)→(XII-A) is generally carried out in a temperature range of from +20° C. to +150° C., preferably at from +50° C. to +100° C. The reaction can be carried out at atmospheric, elevated or reduced pressure (for example from 0.5 to 5 bar); in general, the process is carried out at atmospheric pressure.

Suitable solvents for the process step (XII-A)+(XIII)→(XII-B) are customary organic solvents which do not change under the reaction conditions. These include, for example, ethers, such as diethyl ether, diisopropyl ether, methyl tert-butyl ether, 1,2-dimethoxyethane, 1,4-dioxane or tetrahydrofuran, hydrocarbons, such as pentane, hexane, cyclohexane, benzene, toluene or xylene, halogenated hydrocarbons, such as dichloromethane, 1,2-dichloroethane, trichloromethane or chlorobenzene, or other solvents, such as acetone, methyl ethyl ketone, methyl tert-butyl ketone, acetonitrile, dimethyl sulfoxide, N,N-dimethylformamide, N,N'-dimethylpropyleneurea (DMPU) or N-methylpyrrolidinone (NMP). It is also possible to use mixtures of such solvents. Preference is given to using tetrahydrofuran, acetonitrile or N,N-dimethylformamide.

Suitable bases for the process step (XII-A)+(XIII)→(XII-B) are customary inorganic or organic bases. These include in particular alkali metal or alkaline earth metal carbonates, such as lithium carbonate, sodium carbonate, potassium carbonate, calcium carbonate or caesium carbonate, alkali metal alkoxides, such as sodium tert-butoxide or potassium tert-butoxide, alkali metal hydrides, such as sodium hydride or potassium hydride, amides, such as lithium bis(trimethylsilyl)amide or potassium bis(trimethylsilyl)amide or lithium diisopropylamide (LDA), organic amines, such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU), pyridine or 4-N,N-dimethylaminopyridine, or phosphazene bases ("Schwesinger bases"), such as, for example, P1-t-Bu, P2-t-Bu or P4-t-Bu. Preference is given to using potassium carbonate, caesium carbonate, sodium hydride, triethylamine, N,N-diisopropylethylamine or lithium bis(trimethylsilyl)amide; particular preference is given to sodium hydride and lithium bis(trimethylsilyl)amide. The base is generally employed in an amount of from 0.1 mol to 10 mol, preferably from 1 mol to 3 mol, based on 1 mol of the compound (XII-A).

The process step (XII-A)+(XIII)→(XII-B) is generally carried out in a temperature range of from −78° C. to +100° C., preferably at from −78° C. to +80° C., particularly preferably at from −78° C. to +25° C. The reaction can be carried out at atmospheric, elevated or reduced pressure (for example from 0.5 to 5 bar); in general, the process is carried out at atmospheric pressure.

The reduction of the nitro compound (XII-A) or (XII-B) to the aniline derivative (II) is carried out in accordance with standard methods by catalytic hydrogenation in the presence of a customary palladium or platinum catalyst; preference is given to using palladium on activated carbon. The hydrogenation can take place at atmospheric or at elevated hydrogen pressure; in general, it is carried out at atmospheric pressure. The reaction is preferably carried out at room temperature in alcoholic solvents such as methanol or ethanol, if appropriate with the use of inert cosolvents such as, for example, tetrahydrofuran or ethyl acetate.

According to one process variant, if the radical $R^1$ in formula (I) represents cyano, instead of the compound (X) it is also possible to use an acetoacetic ester of the formula (XIV)

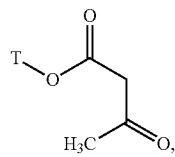
(XIV)

in which

T represents $(C_1-C_4)$-alkyl or allyl, in the condensation reaction with the compounds (IX) and (XI); the resulting product of the formula (XV)

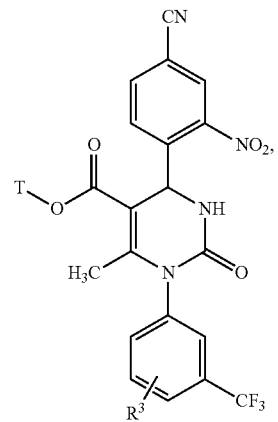
(XV)

in which $R^3$ and T have the meanings given above, can then, by standard methods via ester cleavage to give the carboxylic acid of the formula (XVI)

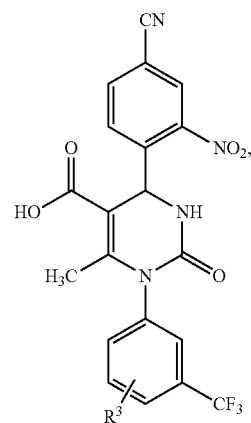
(XVI)

in which $R^3$ has the meaning given above, subsequent conversion into the primary carboxamide of the formula (XVII)

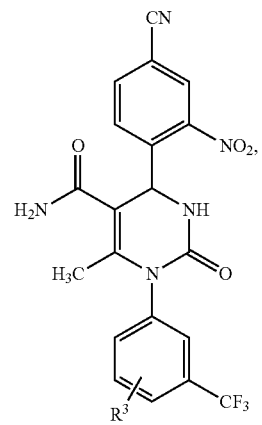
(XVII)

in which $R^3$ has the meaning given above, and subsequent dehydration of the amide grouping be converted into the 5-cyanodihydropyrimidinone of the formula (XII-A) [$R^1$=CN] (cf. Reaction Scheme 1 below).

The compounds of the formula (V) can be prepared in an analogous manner by initially reacting 4-cyano-2-fluorobenzaldehyde of the formula (XVIII)

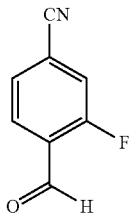

(XVIII)

with a thiol of the formula (XIX)

$R^{Z3}$—SH (XIX), in which $R^{Z3}$ has the meaning given above,
in the presence of a base to give a 2-sulfanyl-substituted benzaldehyde of the formula (XX)

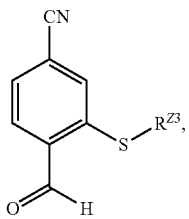

(XX)

in which $R^{Z3}$ has the meaning given above, and then reacting this compound further in exchange for the compound (IX) according to the reaction sequence (IX)+(X)+(XI)→(XII-A)→(XII-B) or (IX)+(XIV)+(XI)→(XV)→(XVI)→(XVII)→(XII-A) described above (cf. Reaction Scheme 2 below).

If expedient, further compounds of the formula (I) according to the invention can also be prepared by transformations of functional groups of individual substituents, in particular those listed under $R^{Z1}$ and $R^{Z2}$, starting with other compounds of the formula (I) obtained by the above process. These transformations are carried out according to customary methods known to the person skilled in the art and include, for example, reactions such as nucleophilic or electrophilic substitution reactions, transition metal-mediated coupling reactions (for example Suzuki, Heck or Hartwig-Buchwald reaction), oxidation, reduction, hydrogenation, alkylation, acylation, amination, hydroxylation, etherification, esterification, ester cleavage and ester hydrolysis, formation of nitriles, carboxamides and carbamates, and also the introduction and removal of temporary protective groups Separation of the compounds according to the invention into the corresponding enantiomers and/or diastereomers is possible, as expedient, at the stage of the compounds (I-A), (I-B) and (I-C) or even at the stage of the compounds (II), (V), (VI) or (VII) or else of the intermediates (XII-A), (XII-B), (XV), (XVI) or (XVII) or their $R^{Z3}$S-substituted analogs, where these intermediates can then, in separated form, be reacted further according to the process steps described above. Such a separation of stereoisomers can be carried out by customary methods known to the person skilled in the art; preference is given to chromatographic methods, in particular to HPLC chromatography on a chiral phase.

The compounds of the formulae (IV), (VIII), (IX), (X), (XI), (XIII), (XIV), (XVIII) and (XIX) are commercially available, known per se from the literature or can be prepared by customary methods described in the literature.

The processes described above can be illustrated in an exemplary manner by the reaction schemes below:

Scheme 1 (part 1)

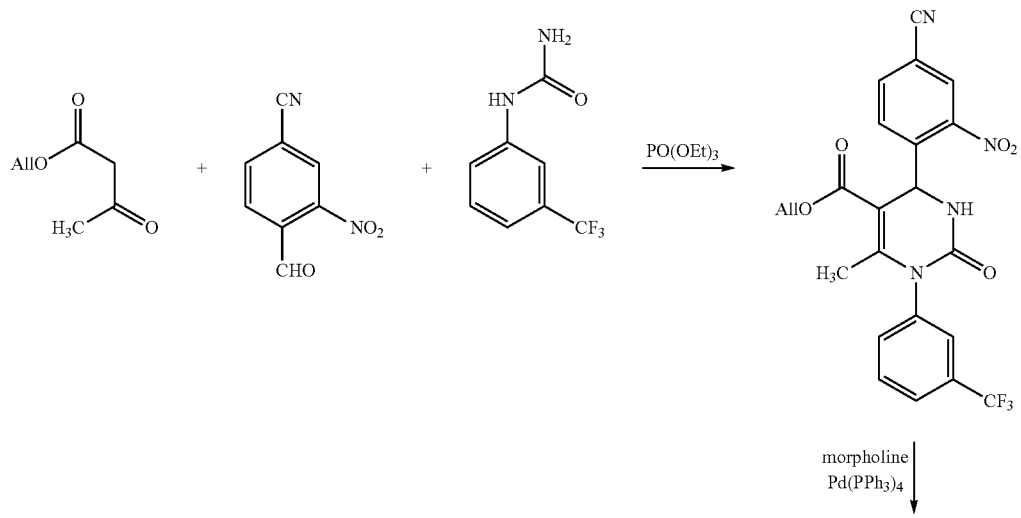

-continued
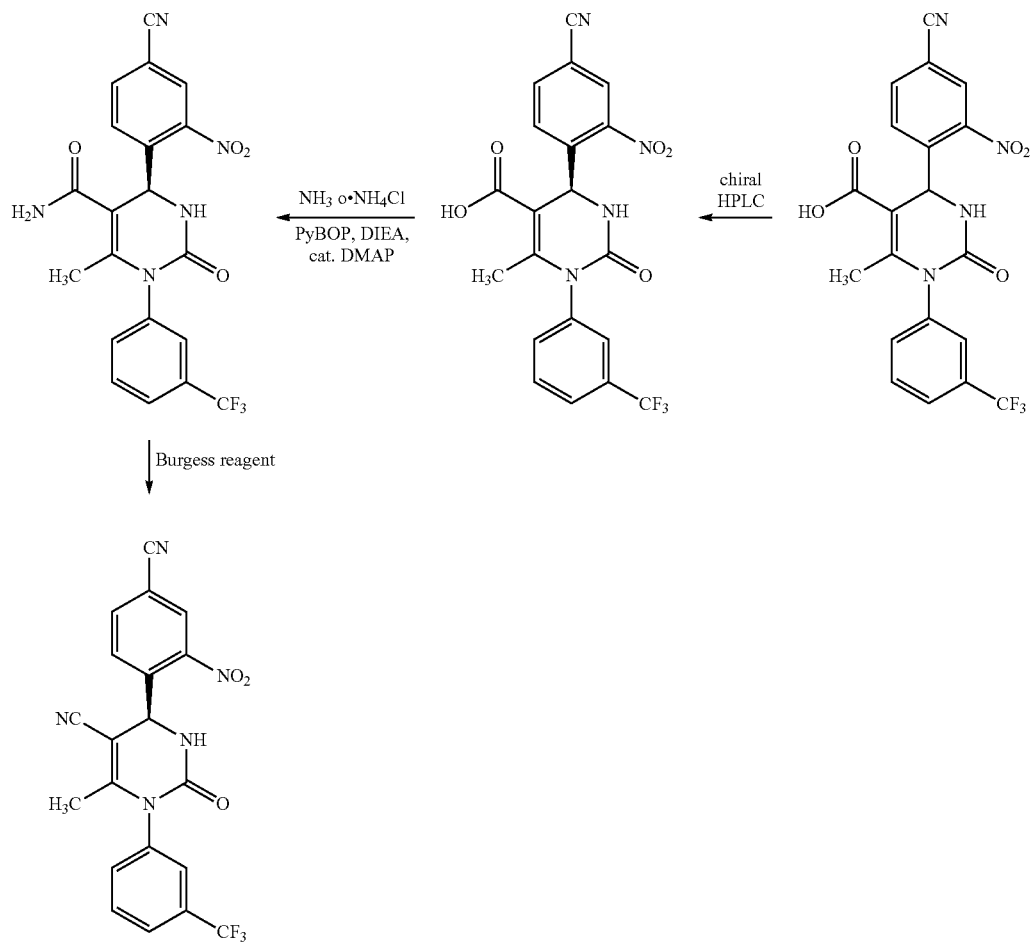
[All = Allyl; Burgess reagent = methoxycarbonylsulfamoyltriethylammonium hydroxide (inner salt)].
Scheme 1 (part 2)
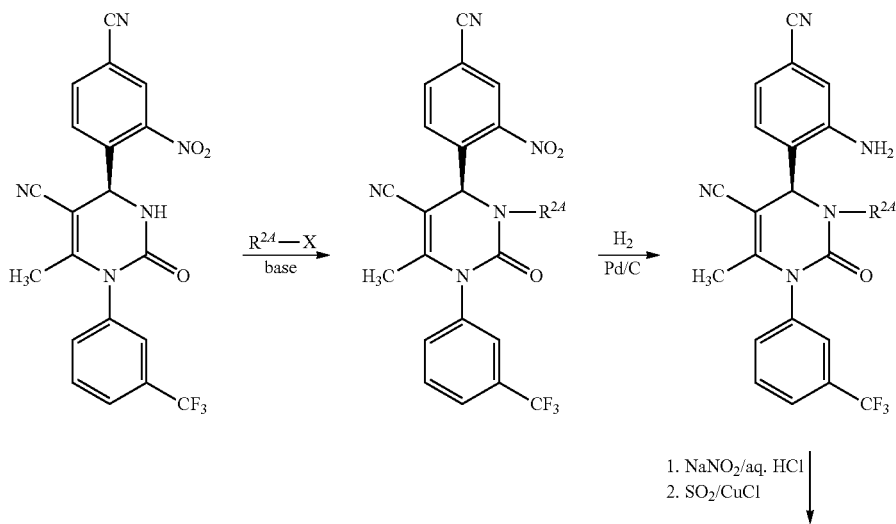
1. NaNO₂/aq. HCl
2. SO₂/CuCl

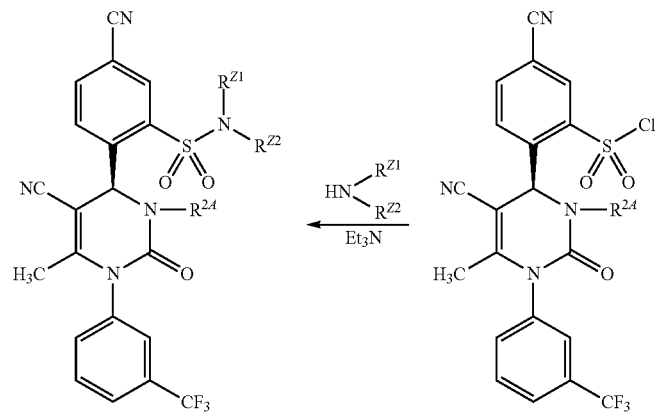
[X = halogen].
Scheme 2 (part 1)
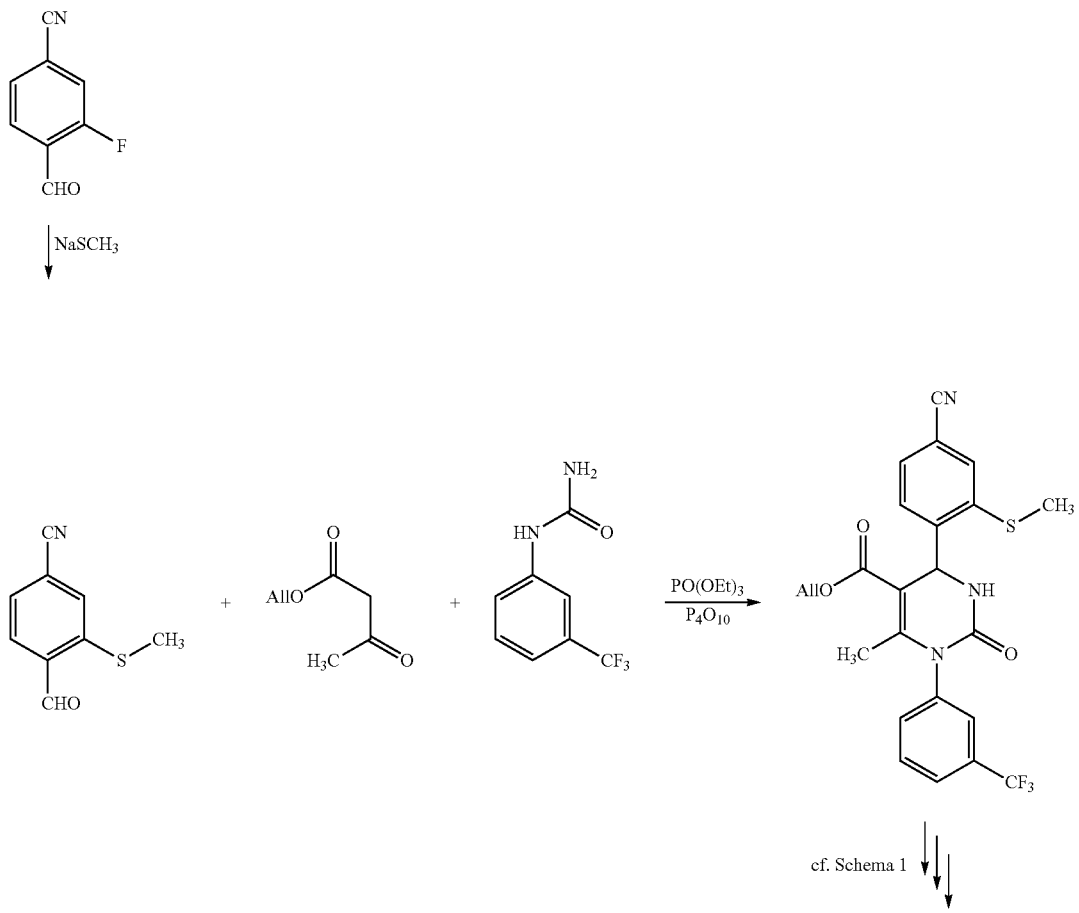

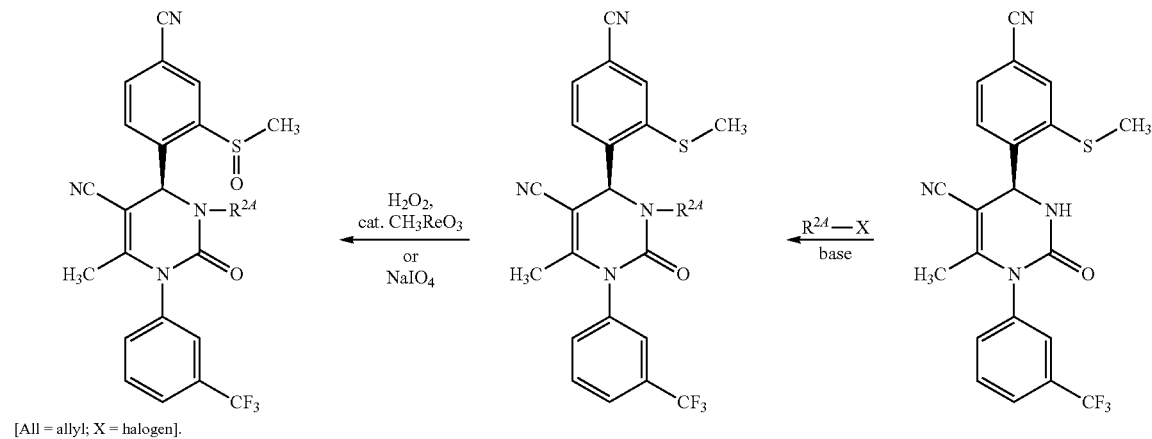

[All = allyl; X = halogen].

Scheme 2 (part 2)

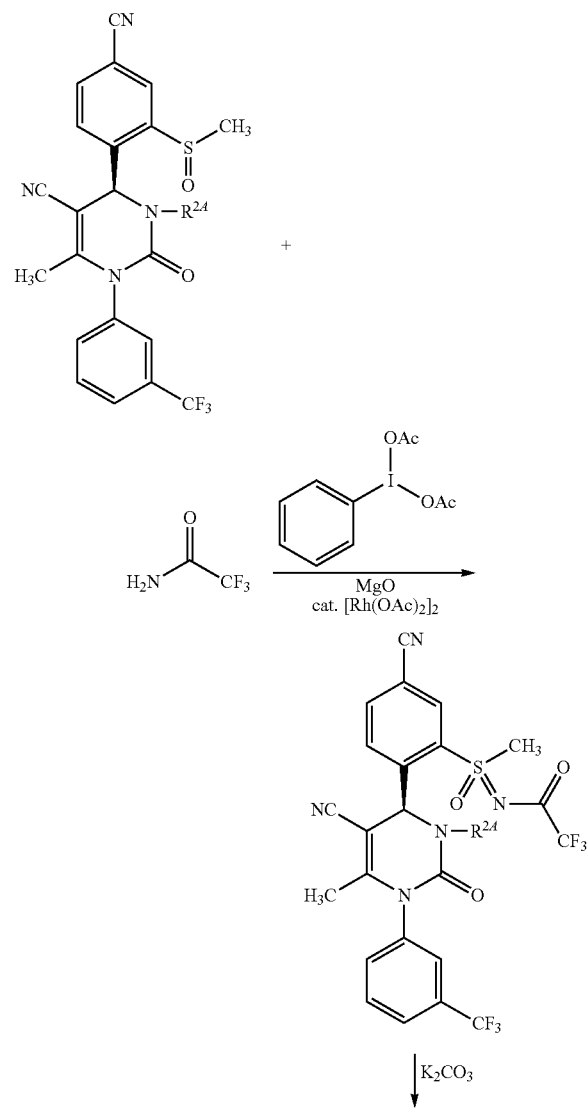

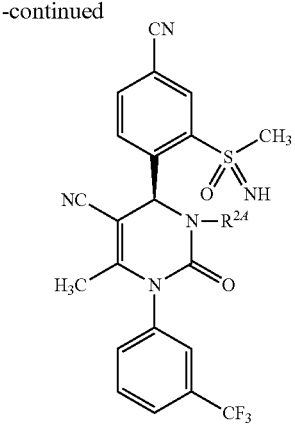

The compounds according to the invention have useful pharmacological properties and can be used for prevention and treatment of disorders in humans and animals.

The compounds according to the invention are low-molecular-weight, unreactive and selective inhibitors of human neutrophil elastase which, surprisingly, effect a considerably stronger inhibition of this protease than the compounds known from the prior art. In addition, the compounds according to the invention unexpectedly have a low in vitro clearance with respect to hepatocytes and thus have improved metabolic stability. Moreover, some of the compounds according to the invention have good solubility in aqueous systems which is advantageous with regard to their general formulatibility and/or intravenous administrability.

Accordingly, the compounds according to the invention are particularly suitable for the treatment and/or prevention of disorders and pathological processes, in particular those where neutrophil elastase (HNE) is involved in an inflammatory event and/or a tissue or vessel remodeling.

For the purposes of the present invention, this includes in particular disorders such as pulmonary arterial hypertension (PAH) and other forms of pulmonary hypertension (PH), chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. cigarette-smoke-induced pulmonary emphysema), cystic fibrosis (CF), acute coronary syndrome (ACS), inflammations of the heart muscle (myocarditis) and other autoimmune heart conditions (pericarditis, endocarditis, valvolitis, aortitis, cardiomyopathies), myocardial infarction, cardiogenic shock, heart failure, aneurysms, sepsis (SIRS), multi-organ failure (MODS, MOF), arteriosclerosis, inflammatory disorders of the kidney, chronic inflammations of the intestine (IBD, CD, UC), pancreatitis, peritonitis, rheumatoid disorders, inflammatory skin disorders and also inflammatory eye disorders.

The compounds according to the invention can furthermore be used for the treatment and/or prevention of asthmatic disorders of various degrees of severity with intermittent or persistent course (refractive asthma, bronchial asthma, allergic asthma, intrinsic asthma, extrinsic asthma, asthma induced by medicaments or by dust), of various forms of bronchitis (chronic bronchitis, infectious bronchitis, eosinophilic bronchitis), of Bronchiolitis obliterans, bronchiectasia, pneumonia, farmer's lung and related diseases, coughs and colds (chronic inflammatory cough, iatrogenic cough), inflammations of the nasal mucosa (including medicament-related rhinitis, vasomotoric rhinitis and seasonal allergic rhinitis, for example hay fever) and of polyps.

In addition, the compounds according to the invention can also be used for the treatment and/or prevention of micro- and macrovascular injuries (vasculitis), reperfusion damage, arterial and venous thromboses, thromboses in connection with orthopedic interventions in patients with rheumatoid arthritis, diabetic and non-diabetic nephropathy, glomerulonephritis, glomerulosclerosis, nephrotic syndrome, hypertensive nephrosclerosis, microalbuminuria, acute and chronic renal insufficiency, acute and chronic renal failure, cystitis, urethritis, prostatitis, epidymitis, oophoritis, salpingitis, vulvovaginitis, erectile dysfunction, Hunner's ulcer, Peyronie's disease, arterial hypertension, shock, atrial and ventricular arrhythmias, transitory and ischemic attacks, heart failure, stroke, endothelial dysfunction, peripheral and cardiovascular disorders, impaired peripheral perfusion, edema formation such as, for example, pulmonary edema, brain edema, renal edema and heart failure-related edema, restenoses, for example after thrombolysis therapies, percutaneous transluminal angioplasties (PTA), transluminal coronary angioplasties (PTCA), heart transplants and bypass operations, for increased levels of fibrinogen and low-density LDL and also for increased concentrations of plasminogen activator inhibitor 1 (PAI-1), of dyslipidemias (hypercholesterolemia, hypertriglyceridemia, increased concentrations of postprandial plasma triglycerides, hypoalphalipoproteinemia, combined hyperlipidemias) and also metabolic disorders (metabolic syndrome, hyperglycemia, insulin-dependent diabetes, non-insulin-dependent diabetes, gestational diabetes, hyperinsulinemia, insulin resistance, glucose intolerance, adipositas and diabetic sequelae, such as retinopathy, nephropathy and neuropathy), neoplastic disorders (skin cancer, brain tumors, breast cancer, bone marrow tumors, leukaemias, liposarcomas, carcinomas of the gastrointestinal tract, the liver, the pancreas, the lungs, the kidneys, the urethra, the prostate and the genital tract and also malignant tumors of the lymphoproliferative system, such as, for example, Hodgkin's and non-Hodgkin's lymphoma), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathias, such as, for example, arthropathie deformans, arthropathie neuropathica, arthropathie ovaripriva, arthropathie psoriatica and arthropathie tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Gunther syndrome and the Münchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

By virtue of their property profile, the compounds according to the invention are suitable in particular for the treatment and/or prevention of pulmonary arterial hypertension (PAH) and other forms of pulmonary hypertension (PH), chronic obstructive lung disease (COPD), acute lung injury (ALI), acute respiratory distress syndrome (ARDS), bronchiectasia, bronchiolitis obliterans, pulmonary emphysema, alpha-1-antitrypsin deficiency (AATD), cystic fibrosis (CF), sepsis and systemic-inflammatory response syndrome (SIRS), multiple organ failure (MOF, MODS), inflammatory intestinal disorders (IBD, Crohn's disease, colitis), chronic bronchitis, asthma, rhinitis, rheumatoid arthritis, inflammatory skin and eye diseases, arterioscleroses and cancerous disorders.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed alone or, if required, in combination with other active compounds. Accordingly, the present invention furthermore provides medicaments comprising at least one of the compounds according to the invention and one or more further active compounds, in particular for the treatment and/or prevention of the disorders mentioned above. Suitable active compounds for combinations are, by way of example and preferably:

compounds which inhibit the signal transduction cascade, for example and preferably from the group of the kinase inhibitors, in particular from the group of the tyrosine kinase and/or serine/threonine kinase inhibitors;

compounds which inhibit the degradation and remodelling of the extracellular matrix, for example and preferably inhibitors of matrix metalloproteases (MMPs), in particular inhibitors of stromelysin, collagenases, gelatinases and aggrecanases (here in particular of MMP-1, MMP-3, MMP-8, MMP-9, MMP-10, MMP-11 and MMP-13) and of metalloelastase (MMP-12);

compounds which block the binding of serotonin to its receptor, for example and preferably antagonists of the 5-HT$_{2b}$ receptor;

organic nitrates and NO donors, such as, for example, sodium nitroprusside, nitroglycerin, isosorbide mononitrate, isosorbide dinitrate, molsidomine or SIN-1, and also inhaled NO;

NO-independent but hem-dependent stimulators of soluble guanylate cyclase, such as, in particular, the compounds described in WO 00/06568, WO 00/06569, WO 02/42301 and WO 03/095451;

NO- and hem-independent activators of soluble guanylate cyclase, such as, in particular, the compounds described in WO 01/19355, WO 01/19776, WO 01/19778, WO 01/19780, WO 02/070462 and WO 02/070510;

prostacycline analogs, such as, by way of example and preferably, iloprost, beraprost, treprostinil or epoprostenol;

compounds which inhibit soluble epoxide hydrolase (sEH), such as, for example, N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, such as, by way of example and preferably, etomoxir, dichloroacetate, ranolazine or trimetazidine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil;

agents having antithrombotic action, by way of example and preferably from the group of the platelet aggregation inhibitors, of anticoagulants or of profibrinolytic substances;

active compounds which lower blood pressure, by way of example and preferably from the group of the calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, Rho kinase inhibitors and diuretics;

agents having a bronchodilatory effect, by way of example and preferably from the group of the beta-adrenergic receptor agonists, such as, in particular, albuterol, isoproterenol, metaproterenol, terbutalin, formoterol or salmeterol, or from the group of the anticholinergics, such as, in particular, ipratropium bromide;

agents having antiinflammatory action, by way of example and preferably from the group of the glucocorticoids, such as, in particular, prednisone, prednisolone, methylprednisolone, triamcinolone, dexamethasone, beclomethasone, betamethasone, flunisolide, budesonide or fluticasone; and/or active compounds which alter lipid metabolism, for example and preferably from the group of the thyroid receptor agonists, cholesterol synthesis inhibitors, such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists.

In a preferred embodiment of the invention, the compounds according to the invention are employed in combination with a kinase inhibitor such as by way of example and preferably bortezomib, canertinib, erlotinib, gefitinib, imatinib, lapatinib, lestaurtinib, lonafarnib, pegaptinib, pelitinib, semaxanib, sorafenib, sunitinib, tandutinib, tipifarnib, vatalanib, fasudil, lonidamine, leflunomide, BMS-3354825 or Y-27632.

In a preferred embodiment of the invention, the compounds according to the invention are employed in combination with a serotonin receptor antagonist such as, by way of example and preferably, PRX-08066.

Agents having an antithrombotic effect preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as by way of example and preferably aspirin, clopidogrel, ticlopidine or dipyridamole.

In a preferred embodiment of the invention, the compounds according to the invention are administered in combination with a thrombin inhibitor such as by way of example and preferably ximelagatran, melagatran, bivalirudin or clexane.

In a preferred embodiment of the invention, the compounds according to the invention are administered in combination with a GPIIb/IIIa antagonist such as by way of example and preferably tirofiban or abciximab.

In a preferred embodiment of the invention, the compounds according to the invention are administered in combination with a factor Xa inhibitor such as by way of example and preferably rivaroxaban, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as by way of example and preferably coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, Rho kinase inhibitors, and diuretics.

In a preferred embodiment of the invention, the compounds according to the invention are administered in combination with a calcium antagonist such as by way of example and preferably nifedipine, amlodipine, verapamil or diltiazem.

In a preferred embodiment of the invention, the compounds according to the invention are administered in combination with an alpha-1 receptor blocker such as by way of example and preferably prazosin.

In a preferred embodiment of the invention, the compounds according to the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as by way of example and preferably losartan, candesartan, valsartan, telmisartan or embusartan.

In a preferred embodiment of the invention, the compounds according to the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist such as by way of example and preferably bosentan, darusentan, ambrisentan or sitaxsentan.

In a preferred embodiment of the invention, the compounds according to the invention are administered in combination with a renin inhibitor such as by way of example and preferably aliskiren, SPP-600 or SPP-800.

In a preferred embodiment of the invention, the compounds according to the invention are administered in combination with a mineralocorticoid receptor antagonist such as by way of example and preferably spironolactone or eplerenone.

In a preferred embodiment of the invention, the compounds according to the invention are administered in combination with a Rho kinase inhibitor such as by way of example and preferably fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic such as by way of example and preferably furosemide.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor such as by way of example and preferably torcetrapib (CP-529 414), JJT-705 or CETP vaccine (Avant).

In a preferred embodiment of the invention, the compounds according to the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as by way of example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as by way of example and preferably BMS-188494 or TAK-475.

In a preferred embodiment of the invention, the compounds according to the invention are administered in combination with an ACAT inhibitor such as by way of example and preferably avasimibe, melinamide, pactimibe, eflucimibe or SMP-797.

In a preferred embodiment of the invention, the compounds according to the invention are administered in combination with an MTP inhibitor such as by way of example and preferably implitapide, BMS-201038, R-103757 or JTT-130.

In a preferred embodiment of the invention, the compounds according to the invention are administered in combination with a PPAR-gamma agonist such as by way of example and preferably pioglitazone or rosiglitazone.

In a preferred embodiment of the invention, the compounds according to the invention are administered in combination with a PPAR-delta agonist such as by way of example and preferably GW-501516 or BAY 68-5042.

In a preferred embodiment of the invention, the compounds according to the invention are administered in combination with a cholesterol absorption inhibitor such as by way of example and preferably ezetimibe, tiqueside or pamaqueside.

In a preferred embodiment of the invention, the compounds according to the invention are administered in combination with a lipase inhibitor such as by way of example and preferably orlistat.

In a preferred embodiment of the invention, the compounds according to the invention are administered in combination with a polymeric bile acid adsorbent such as by way of example and preferably cholestyramine, colestipol, colesolvam, CholestaGel or colestimide.

In a preferred embodiment of the invention, the compounds according to the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein(a) antagonist such as by way of example and preferably gemcabene calcium (CI-1027) or nicotinic acid.

The present invention further provides medicaments comprising at least one compound according to the invention, usually in combination with one or more inert, non-toxic, pharmaceutically suitable excipients, and their use for the purposes mentioned above.

The compounds according to the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds according to the invention can be administered in administration forms suitable for these administration routes.

Suitable for oral administration are administration forms which function according to the prior art and deliver the compounds according to the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. inhalative, intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers, aerosols), nasal drops, solutions or sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration and administration by inhalation.

The compounds according to the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight to achieve effective results. On oral administration, the dosage is about 0.01 to 100 mg/kg, preferably about 0.01 to 20 mg/kg, and very particularly preferably 0.1 to 10 mg/kg of body weight.

It may nevertheless be necessary where appropriate to deviate from the stated amounts, in particular as a function of body weight, administration route, individual response to the active compound, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are in each case, unless indicated otherwise, based on the volume.

A. EXAMPLES

Abbreviations

Ac acetyl
aq. aqueous, aqueous solution
c concentration
cat. catalytic
TLC thin-layer chromatography
DCI direct chemical ionization (in MS)
dist. distilled
DIEA N,N-diisopropylethylamine
DMAP 4-N,N-dimethylaminopyridine
DMF dimethylformamide
DMSO dimethyl sulfoxide
ee enantiomeric excess
ent enantiomerically pure, enantiomer
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium hexafluorophosphate
HPLC high-pressure, high-performance liquid chromatography
conc. concentrated
LC-MS liquid chromatography-coupled mass spectrometry
Me methyl
min minute(s)
MPLC medium-pressure liquid chromatography
MS mass spectrometry
MTBE methyl tert-butyl ether
NMR nuclear magnetic resonance spectrometry
Pd/C palladium on activated carbon
Ph phenyl
PyBOP benzotriazol-1-yloxytris(pyrrolidino)phosphonium hexafluorophosphate
quant. quantitative (in yield)
rac racemic, racemate
RT room temperature
$R_t$ retention time (in HPLC)
m.p. melting point
tBu tert-butyl TFA trifluoroacetic acid
TFAA trifluoroacetic anhydride
THF tetrahydrofuran
UV ultraviolet spectrometry
cf. compare
v/v volume to volume ratio (of a solution)
HPLC, GC-MS and LC-MS Methods:
Method 1 (GC-MS):
 Instrument: Micromass GCT, GC 6890; column: Restek RTX-35, 15 m×200 µm×0.33 µm; constant helium flow: 0.88 ml/min; oven: 70° C.; inlet: 250° C.; gradient: 70° C., 30° C./min→310° C. (maintained for 3 min)
Method 2 (Analytical HPLC):
 Instrument: HP 1100 with DAD detection; column: Kromasil 100 RP-18, 60 mm×2.1 mm, 3.5 µm; mobile phase A: 5 ml of $HClO_4$ (70% strength)/liter of water, mobile phase B: acetonitrile; gradient: 0 min 2% B→0.5 min 2% B→4.5 min 90% B→9.0 min 90% B→9.2 min 2% B→10 min 2% B; flow rate: 0.75 ml/min; column temperature: 30° C.; UV detection: 210 nm.
Method 3 (Analytical HPLC):
 Instrument: HP 1100 with DAD detection; column: Kromasil 100 RP-18, 60 mm×2.1 mm, 3.5 µm; mobile phase A: 5 ml of $HClO_4$ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.
Method 4 (LC-MS):
 Instrument: Micromass QuattroPremier with Waters HPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient 0.0 min 90% A→0.1 min 90% A→1.5 min 10% A→2.2 min 10% A; flow rate: 0.33 ml/min; oven: 50° C.; UV detection: 210 nm.
Method 5 (LC-MS):
 MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
Method 6 (LC-MS):
 MS instrument type: Micromass ZQ; HPLC instrument type: HP 1100 Series; UV DAD; column: Phenomenex Gemini 3µ 30 mm×3.0 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 7 (LC-MS):
 MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.
Method 8 (LC-MS):
 Instrument: Waters Acquity SQD HPLC System; column: Waters Acquity HPLC HSS T3 1.8µ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.
Method 9 (LC-MS):
 Instrument: Micromass Quattro Micro MS mit HPLC Agilent Serie 1100; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Method 10 (LC-MS):
 MS instrument type: Waters ZQ; HPLC instrument type: Agilent 1100 Series; UV DAD; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.
Method 11 (LC-MS):
 MS instrument: Waters ZQ 2000; HPLC instrument: Agilent 1100, 2-column circuit; autosampler: HTC PAL; column: YMC-ODS-AQ, 50 mm×4.6 mm, 3.0 µm; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Starting Materials and Intermediates

Example 1A (rac)-Allyl 4-(4-cyano-2-nitrophenyl)-6-methyl-2-oxo-1-[3-(trifluoromethyl)phenyl]-1,2,3,4-tetrahydropyrimidine-5-carboxylate

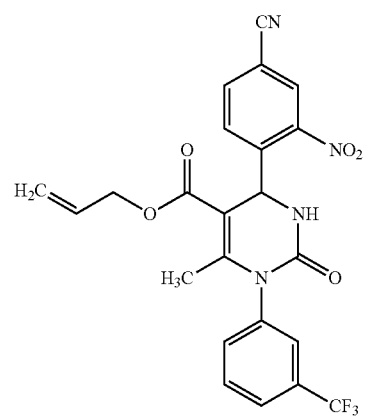 [SMILES: C=CCOC(=O)C1=C(C)N(c2cccc(C(F)(F)F)c2)C(=O)NC1c1ccc(C#N)cc1[N+](=O)[O-]]

The reaction was carried out under argon. At RT, allyl acetoacetate (5.94 g, 41.5 mmol; 1.0 eq.) was initially charged in THF (117 ml). 4-Cyano-2-nitrobenzaldehyde (10.45 g, 70% pure, 41.5 mmol; 1.0 eq.), 1-[3-(trifluoromethyl)phenyl]urea (8.48 g, 41.5 mmol) and triethyl phosphate (17.7 g) were then added. The mixture was stirred under reflux for 16 h. For work-up, ice-water was initially added, and the mixture was then taken up in ethyl acetate (400 ml). The organic phase was dried over solid sodium sulfate, filtered and concentrated under reduced pressure. The crude product was recrystallized from hot water/isopropanol (2:1, ~400 ml). The solid obtained was stirred in diethyl ether (60 ml), once more filtered off with suction, washed with a little diethyl ether and dried under high vacuum. The title compound was obtained as a solid (16.63 g, 82% of theory).

LC-MS (Method 7): $R_t$=3.70 min; MS (ESIpos): m/z (%)=487.1 (100) [M+H]$^+$ $^1$H-NMR (400 MHz, DMSO-d$_6$): δ=2.10 (s, 3H), 4.40 (m, 2H), 4.95 (d, 1H), 5.05 (d, 1H), 5.70 (m, 1H), 6.15 (d, 1H), 6.05 (d, 1H), 7.70-7.90 (m, 4H), 8.10 (br. d, 1H), 8.25 (dd, 1H), 8.45 (d, 1H), 8.55 (d, 1H).

Example 2A (rac)-4-(4-Cyano-2-nitrophenyl)-6-methyl-2-oxo-1-[3-(trifluoromethyl)phenyl]-1,2,3,4-tetrahydropyrimidine-5-carboxylic acid

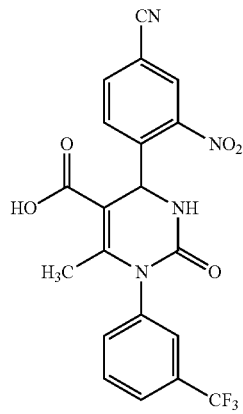 [SMILES: CC1=C(C(=O)O)C(c2ccc(C#N)cc2[N+](=O)[O-])NC(=O)N1c1cccc(C(F)(F)F)c1]

The reaction was carried out under argon. (rac)-Allyl 4-(4-cyano-2-nitrophenyl)-6-methyl-2-oxo-1-[3-(trifluoromethyl)phenyl]-1,2,3,4-tetrahydropyrimidine-5-carboxylate (15.0 g, 30.8 mmol) and morpholine (1.5 eq., 4.03 g, 46.3 mmol) were initially charged in dry THF (300 ml) at RT. The reaction mixture was degassed repeatedly (evacuation followed by venting with argon). Under protective gas, tetrakis(triphenylphosphine)palladium(0) (0.05 eq., 1.78 g, 1.54 mmol) was added and the reaction mixture was stirred at RT for 2 h (monitored by HPLC). The mixture was then concentrated and the residue was taken up in ethyl acetate (700 ml). The organic phase was washed with 0.5 N hydrochloric acid (500 ml) and with saturated sodium chloride solution (300 ml), dried over sodium sulfate, filtered and concentrated under reduced pressure. The crude product was recrystallized from ethyl acetate and dried under high vacuum. The title compound was obtained as a solid (12.87 g, 93% of theory).

$^1$H-NMR (400 MHz, DMSO-d$_6$): δ=2.05 (s, 3H), 6.00 (d, 1H), 7.65-7.90 (m, 4H), 8.10 (d, 1H), 8.25 (dd, 1H), 8.40 (d, 1H), 8.50 (d, 1H), 12.5 (br. s, 1H).

Example 3A (4R)-4-(4-Cyano-2-nitrophenyl)-6-methyl-2-oxo-1-[3-(trifluoromethyl)phenyl]-1,2,3,4-tetrahydropyrimidine-5-carboxylic acid

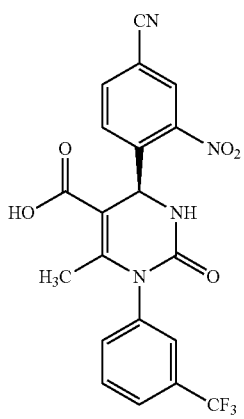 [SMILES: CC1=C(C(=O)O)[C@@H](c2ccc(C#N)cc2[N+](=O)[O-])NC(=O)N1c1cccc(C(F)(F)F)c1]

(rac)-4-(4-Cyano-2-nitrophenyl)-6-methyl-2-oxo-1-[3-(trifluoromethyl)phenyl]-1,2,3,4-tetrahydropyrimidine-5-carboxylic acid (590 g) was separated into the enantiomers by preparative HPLC chromatography on a chiral phase [column: chiral silica gel phase based on the selector poly(N-methacryloyl-L-leucine-tert-butylamide); column dimensions: 670 mm×40 mm; sample preparation: 100 g of sample dissolved in 2000 ml of THF; injection volume: 70 ml; mobile phase: ethyl acetate/methanol 100:1→1:100; flow rate: 80 ml/min; temperature: 24° C.; detection: 260 nm]. This gave 280 g (95% of theory; 99.6% ee) of the 4R enantiomer.

The enantiomeric excess (ee) was determined chromatographically [column: chiral silica gel phase based on the selector poly(N-methacryloyl-L-leucine-tert-butylamide); column dimensions: 250 mm×4.6 mm; mobile phase: ethyl acetate/methanol 10:1; flow rate: 2 ml/min; detection: 265 nm; $R_t$=1.38 min].

Example 4A (4R)-4-(4-Cyano-2-nitrophenyl)-6-methyl-2-oxo-1-[3-(trifluoromethyl)phenyl]-1,2,3,4-tetrahydropyrimidine-5-carboxamide

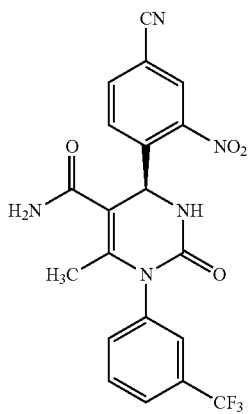 [SMILES: CC1=C(C(N)=O)[C@@H](c2ccc(C#N)cc2[N+](=O)[O-])NC(=O)N1c1cccc(C(F)(F)F)c1]

The reaction was carried out under argon. At RT, (4R)-4-(4-Cyano-2-nitrophenyl)-6-methyl-2-oxo-1-[3-(trifluoromethyl)phenyl]-1,2,3,4-tetrahydropyrimidine-5-carboxylic acid (6.0 g, 11.4 mmol, 85% pure), DMAP (140 mg, 1.143 mmol; 0.1 eq.), DIEA (1.77 g, 13.7 mmol; 1.2 eq.) and PyBOP (7.14 g, 13.71 mmol; 1.2 eq.) were initially charged in dry THF (34 ml), after brief stirring (15 min), a 0.5 M solution of ammonia in THF (5 eq., 57.1 mmol) was added and the mixture was then stirred at RT for 1 h. Ethyl acetate (250 ml) was then added to the reaction mixture. The organic phase was washed successively with saturated sodium bicarbonate solution, water and saturated sodium chloride solution, dried over sodium sulfate, filtered and concentrated under reduced pressure. The crude product was subjected to flash chromatography on silica gel (mobile phase: dichloromethane/methanol 20:1). The title compound was obtained as a colorless solid (5.0 g, 98% of theory).

MS (ESIpos): m/z (%)=446.2 (100) $[M+H]^+$.

Example 5A (4R)-4-(4-Cyano-2-nitrophenyl)-6-methyl-2-oxo-1-[3-(trifluoromethyl)phenyl]-1,2,3,4-tetrahydropyrimidine-5-carbonitrile

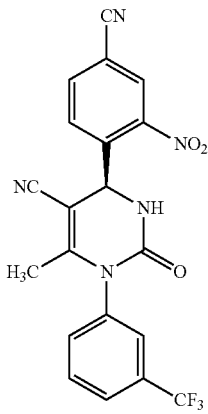 [SMILES: CC1=C(C#N)[C@@H](c2ccc(C#N)cc2[N+](=O)[O-])NC(=O)N1c1cccc(C(F)(F)F)c1]

The reaction was carried out under argon. (4R)-4-(4-Cyano-2-nitrophenyl)-6-methyl-2-oxo-1-[3-(trifluoromethyl)phenyl]-1,2,3,4-tetrahydropyrimidine-5-carboxamide (5.0 g, 10.1 mmol; 90% pure) was initially charged in dry THF (135 ml), methoxycarbonylsulfamoyltriethylammonium hydroxide (Burgess reagent; 3.85 g, 16.17 mmol; 1.6 eq.) was added and the mixture was then stirred at RT for 2 h. Ethyl acetate (300 ml) was then added to the reaction mixture. The organic phase was washed twice with water and once with saturated sodium chloride solution, dried over sodium sulfate, filtered and concentrated under reduced pressure. The crude product was recrystallized from cyclohexane/ethyl acetate. The crystals obtained were dried under high vacuum. The title compound was obtained as a solid (2.8 g, 65% of theory).

$^1$H-NMR (400 MHz, DMSO-$d_6$): δ=1.80 (s, 3H), 5.95 (s, 1H), 7.75-8.25 (m, 6H), 8.35 (dd, 1H), 8.65 (s, 1H).

Example 6A (4R)-4-(4-Cyano-2-nitrophenyl)-3,6-dimethyl-2-oxo-1-[3-(trifluoromethyl)phenyl]-1,2,3,4-tetrahydropyrimidine-5-carbonitrile

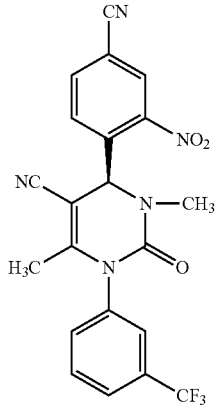

The reaction was carried out under argon. (4R)-4-(4-Cyano-2-nitrophenyl)-6-methyl-2-oxo-1-[3-(trifluoromethyl)phenyl]-1,2,3,4-tetrahydropyrimidine-5-carbonitrile (5.0 g, 11.7 mmol) was initially charged in absolute THF (500 ml), and a 1 M solution of lithium hexamethyldisilazide (LiHMDS) in THF (13.5 ml, 13.5 mmol; 1.15 eq.) was added at −78° C. After 30 min of stirring, iodomethane (8.30 g, 58.5 mmol; 5 eq.) in THF was added and the mixture was stirred for 16 h while slowly warming from −78° C. to RT. The reaction mixture was then concentrated under reduced pressure, and initially 1 N hydrochloric acid (14.0 ml) and then MTBE (500 ml) were added. The organic phase was washed successively with water (2×), saturated sodium bicarbonate solution, saturated ammonium chloride solution and saturated sodium chloride solution, dried over sodium sulfate, filtered and concentrated under reduced pressure. The title compound was obtained as a solid (4.3 g, 83% of theory).

LC-MS (Method 4): $R_t$=1.28 min; MS (ESIpos): m/z (%)=442.2 (100) $[M+H]^+$; MS (ESIneg): m/z (%)=440.2 (50) $[M-H]^-$ $^1$H-NMR (400 MHz, DMSO-$d_6$): δ=1.80 (s, 3H), 2.70 (s, 3H), 5.95 (s, 1H), 7.75-8.25 (m, 5H), 8.35 (dd, 1H), 8.65 (s, 1H).

Example 7A (4R)-4-(2-Amino-4-cyanophenyl)-3,6-dimethyl-2-oxo-1-[3-(trifluoromethyl)phenyl]-1,2,3,4-tetrahydropyrimidine-5-carbonitrile

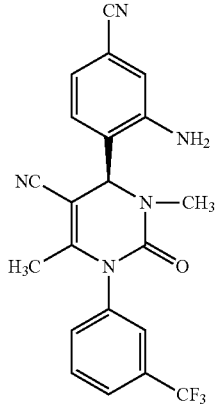

Under argon, (4R)-4-(4-cyano-2-nitrophenyl)-3,6-dimethyl-2-oxo-1-[3-(trifluoromethyl)phenyl]-1,2,3,4-tetrahydropyrimidine-5-carbonitrile (6.0 g, 11.3 mmol) was dissolved in methanol (420 ml). 10% Palladium on activated carbon (5.5 g) was then added, and the mixture was hydrogenated at RT and atmospheric pressure for 5.5 h (strictly monitored by HPLC). The reaction mixture was then filtered through kieselguhr and the filter residue was washed with methanol (1000 ml). The filtrate was concentrated and the crude product was subjected to flash chromatography on silica gel (mobile phase: ethyl acetate/cyclohexane 2:1). The title compound was obtained as a solid (2.28 g, 40% of theory).

LC-MS (Method 8): $R_t$=1.06 min; MS (ESIpos): m/z (%)=412.3 (80) [M+H]$^+$; MS (ESIneg): m/z (%)=410.3 (100) [M−H]$^−$.

Example 8A

5-Cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride

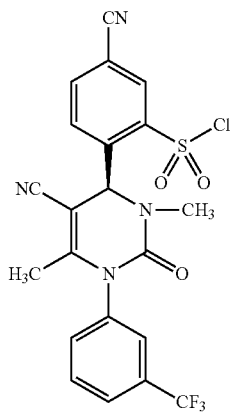 [SMILES: CC1=C(C#N)[C@@H](c2ccc(C#N)cc2S(=O)(=O)Cl)N(C)C(=O)N1c1cccc(C(F)(F)F)c1]

Under argon, (4R)-4-(2-amino-4-cyanophenyl)-3,6-dimethyl-2-oxo-1-[3-(trifluoromethyl)phenyl]-1,2,3,4-tetrahydropyrimidine-5-carbonitrile (2.1 g, 5.1 mmol) was initially charged in a 2:1:1 mixture of acetic acid/conc. hydrochloric acid/water (50 ml in total) at −10° C. A solution of sodium nitrite (371 mg, 5.38 mmol) in water (2 ml) was slowly added dropwise, and the mixture was stirred at −10° C. to −5° C. for 40 min. This solution was then added to 45 ml of a suspension, pre-cooled to −10° C. and saturated with sulfur dioxide, of copper(I) chloride (101.4 mg, 1.0 mmol) in glacial acetic acid (44 ml). The mixture was stirred at 0° C. for about 30 min and then at +15° C. for 1 h (reaction monitored by HPLC and LC-MS). The reaction mixture was then once more cooled to 0° C. and then pipetted into about 300 ml of ice-cold water. The precipitate was filtered off and taken up in ethyl acetate (150 ml). The solution was washed twice with saturated sodium chloride solution, dried over sodium sulfate, filtered and concentrated under reduced pressure. The title compound was obtained as a solid (2.13 g, 77% of theory, 92% pure) which was used without further purification for subsequent reactions.

LC-MS (Method 4): $R_t$=1.37 min; MS (ESIpos): m/z (%)=495.1 (100) [M+H]$^+$ $^1$H-NMR (400 MHz, DMSO-d$_6$): δ=1.80 (s, 3H), 2.70 (s, 3H), 6.55 (s, 1H), 7.75-8.00 (m, 6H), 8.10 (s, 1H).

Example 9A (4R)-4-(2-Amino-4-cyanophenyl)-6-methyl-2-oxo-1-[3-(trifluoromethyl)phenyl]-1,2,3,4-tetrahydropyrimidine-5-carbonitrile

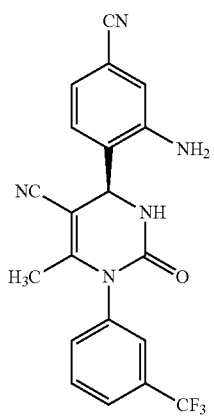 [SMILES: CC1=C(C#N)[C@@H](c2ccc(C#N)cc2N)NC(=O)N1c1cccc(C(F)(F)F)c1]

Under argon, (4R)-4-(4-cyano-2-nitrophenyl)-6-methyl-2-oxo-1-[3-(trifluoromethyl)phenyl]-1,2,3,4-tetrahydropyrimidine-5-carbonitrile (39.5 g, 92.4 mmol) was dissolved in ethanol (1975 ml). 10% Palladium on activated carbon (19.8 g) was then added, and the mixture was hydrogenated at RT and atmospheric pressure for 2 h (strictly monitored by TLC). The reaction mixture was then filtered through kieselguhr. The filtrate was concentrated and the crude product obtained was subjected to flash chromatography on silica gel (mobile phase: ethyl acetate/cyclohexane 2:1). The title compound was obtained as a solid (25.5 g, 68% of theory).

LC-MS (Method 10): $R_t$=2.21 min; MS (ESIpos): m/z (%)=398.2 (100) [M+H]$^+$.

Example 10A

5-Cyano-2-{(4S)-5-cyano-6-methyl-2-oxo-1-[3-(trifluoromethyl)phenyl]-1,2,3,4-tetrahydropyrimidin-4-yl}benzenesulfonyl chloride

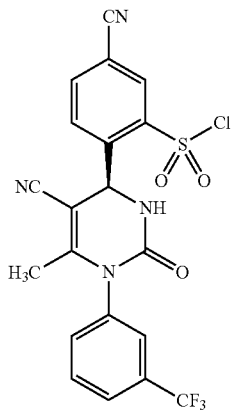 [SMILES: CC1=C(C#N)[C@@H](c2ccc(C#N)cc2S(=O)(=O)Cl)NC(=O)N1c1cccc(C(F)(F)F)c1]

Under argon, (4R)-4-(2-amino-4-cyanophenyl)-6-methyl-2-oxo-1-[3-(trifluoromethyl)phenyl]-1,2,3,4-tetrahydropyrimidine-5-carbonitrile (3.0 g, 7.55 mmol) was initially charged in a 2:1:1 mixture of acetic acid/conc. hydrochloric acid/water (50 ml in total) at −10° C. A solution of sodium nitrite (547 mg, 7.93 mmol) in water (6 ml) was added, and the mixture was stirred at −10° C. for 15 min. This solution was then added to a suspension, pre-cooled to −10° C. and saturated with sulfur dioxide, of copper(I) chloride (75 mg, 755 µmol; 0.1 eq.) in glacial acetic acid (60 ml). The reaction was stirred at −10° C. (internal temperature) for 60 min and then slowly, over a period of 3 h, warmed to +15° C. (reaction monitored by HPLC and LC-MS). The reaction mixture was then once more cooled to 0° C., and then pipetted into about 300 ml of ice-cold water. The aqueous phase was extracted repeatedly with MTBE. The combined organic phases were washed twice with saturated sodium chloride solution, dried over sodium sulfate, filtered and concentrated under reduced pressure. The title compound was obtained as a solid (1.67 g, 73% pure according to LC-MS, 32% of theory) and used without further purification for subsequent reactions.

LC-MS (Method 6): $R_t$=2.52 min; MS (ESIpos): m/z (%)=481.0 (100) [M+H]$^+$.

Example 11A

3-Fluoro-4-formylbenzonitrile

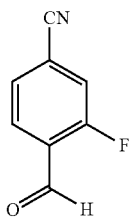

The reaction was carried out under argon. 3-Fluoro-4-methylbenzonitrile (121 g, 895 mmol) and N,N-dimethylformamide dimethylacetal (245 g, 2.06 mol) were dissolved in DMF (1.8 liters) and stirred under reflux overnight. The content of the flask was then poured into water (2 liters), the mixture was extracted twice with ethyl acetate and the combined organic phases were washed with saturated sodium chloride solution. The organic phase was concentrated and the residue was redissolved in THF/water (1:1, 2.7 liters). Sodium periodate (503 g, 2.35 mol) was added, and the mixture was stirred at room temperature for one hour. The precipitate was then removed and the filtrate was recovered and extracted repeatedly with ethyl acetate. The combined organic phases were washed once with saturated sodium bicarbonate solution and once with saturated sodium chloride solution, dried and concentrated to give an oil. This oil was purified by column chromatography on silica gel (mobile phase: petroleum ether/dichloromethane 6:4, then 4:6, finally pure dichloromethane). The product fractions were concentrated. This gave 28.0 g (20% of theory) of the target compound as a white crystalline solid.

GC-MS (Method 1): $R_t$=3.63 min; MS (ESIpos): m/z (%)=149.0 (48) [M]$^+$, 150.0 (5) [M+H]$^+$ $^1$H-NMR (400 MHz, DMSO-d$_6$): δ=7.89 (d, 1H), 8.00 (t, 1H), 8.11 (d, 1H), 10.24 (s, 1H).

Example 12A

4-Formyl-3-(methylsulfanyl)benzonitrile

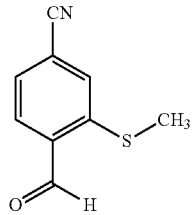

3-Fluoro-4-formylbenzonitrile (2.00 g, 13.4 mmol) was dissolved in DMSO (27 ml), and sodium methanethiolate (1.50 g, 21.5 mmol) was added with ice-bath cooling. The mixture was stirred for 45 min and then diluted with water (100 ml). The resulting precipitated product was filtered off with suction, washed with water and dried under reduced pressure. This gave 1.36 g (51% of theory) of the target compound as a yellow crystalline solid.

GC-MS (Method 1): $R_t$=5.90 min; MS (ESIpos): m/z (%)=177.0 (100) [M]$^+$, 178.0 (11) [M+H]$^+$.

Example 13A

Allyl (rac)-4-[4-cyano-2-(methylsulfanyl)phenyl]-6-methyl-2-oxo-1-[3-(trifluoromethyl)phenyl]-1,2,3,4-tetrahydropyrimidine-5-carboxylate

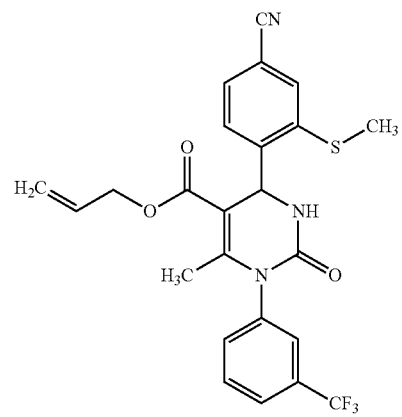 [SMILES: C=CCOC(=O)C1=C(C)N(c2cccc(C(F)(F)F)c2)C(=O)NC1c1ccc(C#N)cc1SC]

The reaction was carried out under argon. Triethyl phosphate (1.46 g, 8.04 mmol) and phosphorus pentoxide (761 mg, 5.36 mmol) were stirred at 50° C. overnight. The mixture was then diluted with MTBE (27 ml), and 4-formyl-3-(methylsulfanyl)benzonitrile (1.18 g, 6.70 mmol), 1-[3-(trifluoromethyl)phenyl]urea (1.37 g, 6.70 mmol) and allyl acetoacetate (1.43 g, 10.1 mmol) were added. The mixture was stirred under reflux overnight. For work-up, the solvent was removed under reduced pressure and the residue was suspended in diethyl ether and then filtered off with suction. This gave 978 mg (19% of theory) of the title compound.

LC-MS (Method 4): $R_t$=1.37 min; MS (ESIpos): m/z (%)=488.3 (100) [M+H]$^+$; MS (ESIneg): m/z (%)=486.2 (65) [M−H]$^-$.

Example 14A (rac)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid

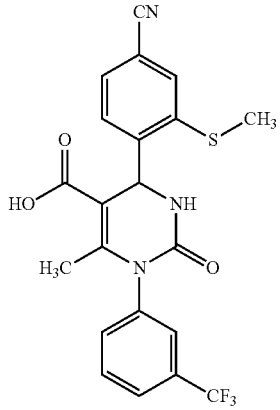 [SMILES: CSc1cc(C#N)ccc1C1NC(=O)N(c2cccc(C(F)(F)F)c2)C(C)=C1C(=O)O]

Allyl (rac)-4-[4-cyano-2-(methylsulfanyl)phenyl]-6-methyl-2-oxo-1-[3-(trifluoromethyl)phenyl]-1,2,3,4-tetrahydropyrimidine-5-carboxylate (750 mg, 1.54 mmol) was dissolved in THF (10 ml), and morpholine (201 mg, 2.308 mmol) was added. The reaction solution was saturated with argon (argon was passed through the solution for 30 min). Tetrakis(triphenylphosphine)palladium(0) (7.47 mg, 0.006 mmol) was then added, and the mixture was stirred at RT overnight. Since HPLC showed little conversion, more tetrakis(triphenylphosphine)palladium(0) (7.47 mg, 0.006 mmol) was added and the mixture was stirred at RT for a further 3 h. The content of the flask was then filtered through kieselguhr and the residue was washed with THF. The filtrate was concentrated under reduced pressure and the residue was recrystallized from diethyl ether (15 ml). The crystals were filtered off with suction and dried under high vacuum. This gave 663 mg (96% of theory) of the target compound.

LC-MS (Method 4): $R_t$=1.10 min; MS (ESIpos): m/z (%)=448.0 (100) [M+H]$^+$; MS (ESIneg): m/z (%)=446.3 (100) [M−H]$^-$.

Example 15A (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid

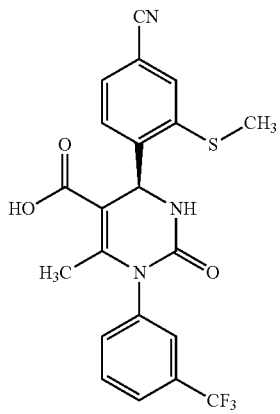 [SMILES: CSc1cc(C#N)ccc1[C@H]1NC(=O)N(c2cccc(C(F)(F)F)c2)C(C)=C1C(=O)O]

(rac)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid (663 mg, 1.48 mmol) was separated into the enantiomers by preparative HPLC chromatography on a chiral phase [column: chiral silica gel phase based on the selector poly(N-methacryloyl-D-leucine-dicyclopropylmethylamide); column dimensions: 670 mm×40 mm; sample preparation: the sample was dissolved in 20 ml of methanol/ethyl acetate 1:3; injection volume: 15 ml; gradient elution: ethyl acetate (100%)→methanol (100%); flow rate: 80 ml/min; temperature: 25° C.; detection: 260 nm]. This gave 279 mg (84% of theory, 96% ee) of the 4S enantiomer as a colorless amorphous solid.

HPLC (Method 2): $R_t$=4.15 min.

MS (DCI/NH$_3$): m/z=448.1 [M+H]$^+$ $^1$H-NMR (400 MHz, DMSO-d$_6$): δ=2.07 (s, 3H), 2.57 (s, 3H), 5.80 (d, 1H), 7.62-7.83 (m, 7H), 8.02 (d, 1H).

Optical rotation: $[\alpha]^{20}_{Na}$=+14.0° (c=0.210 in DMF).

Example 16A (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxamide

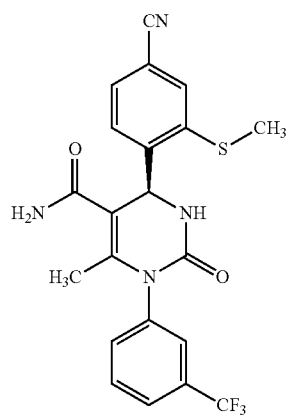 [SMILES: CSc1cc(C#N)ccc1[C@H]1NC(=O)N(c2cccc(C(F)(F)F)c2)C(C)=C1C(N)=O]

The reaction was carried out under argon. (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid (240 mg, 0.536 mmol) was dissolved in THF (5 ml), and PyBOP (419 mg, 0.805 mmol) and triethylamine (380 mg, 3.76 mmol) were added. After brief stirring the mixture was cooled to 0° C., and ammonium chloride (143 mg, 2.68 mmol) was added. The reaction mixture was stirred at RT overnight and the content of the flask was then added to 1 N hydrochloric acid. The mixture was extracted twice with ethyl acetate, and the combined organic phases were washed with 1 N hydrochloric acid and with saturated sodium chloride solution, dried and concentrated. The residue was purified by preparative HPLC. This gave 161 mg (67% of theory) of the title compound.

LC-MS (Method 4): $R_t$=0.99 min; MS (ESIpos): m/z (%)=447.1 (100) [M+H]$^+$; MS (ESIneg): m/z (%)=445.3 (100) [M−H]$^-$.

Example 17A (4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile

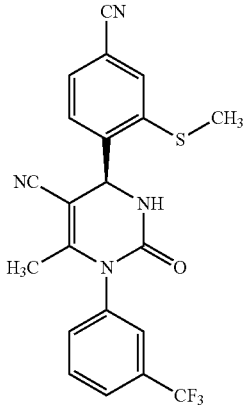

The reaction was carried out under argon. (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxamide (95.0 mg, 0.213 mmol) was dissolved in THF (4 ml), and methoxycarbonylsulfamoyltriethylammonium hydroxide (Burgess reagent; 101 mg, 0.426 mmol) was added. After 30 min of stirring at room temperature, HPLC showed complete conversion. The mixture was diluted with ethyl acetate (4 ml), and water (1 ml) was added. The mixture was then applied to a Merck Extrelut® NT3 column and the filtrate was purified by preparative HPLC. Concentration of the product fractions gave 96.0 mg (quant.) of the title compound.

HPLC (Method 3): $R_t$=4.61 min.
MS (DCI/NH$_3$): m/z=429.1 [M+H]$^+$, 446.1 [M+NH$_4$]$^+$
$^1$H-NMR (400 MHz, DMSO-d$_6$): δ=1.80 (s, 3H), 2.61 (s, 3H), 5.76 (s, 1H), 7.67-7.89 (m, 7H), 8.28 (s, 1H).

Example 18A (R$_S$,4S)-4-[4-Cyano-2-(methylsulfinyl)phenyl]-6-methyl-2-oxo-1-[3-(trifluoromethyl)phenyl]-1,2,3,4-tetrahydropyrimidine-5-carbonitrile and (S$_S$,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile (diastereomer mixture)

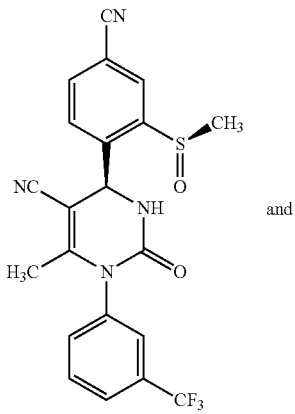

and

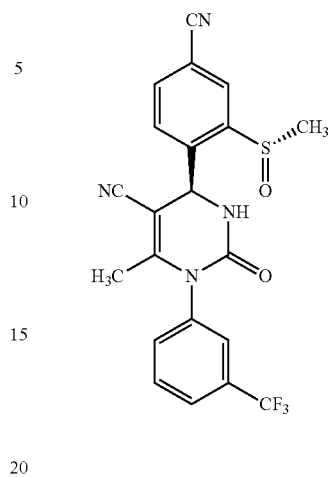

Method A:

(4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile (55 mg, 0.13 mmol) was dissolved in ethanol (5.5 ml), and methyltrioxorhenium (3.20 mg, 0.013 mmol) and hydrogen peroxide (16.0 mg, 0.14 mmol) were added. The reaction mixture was stirred at RT for 60 min and then concentrated under reduced pressure, and the residue was purified by preparative HPLC. This gave 27 mg (47% of theory) of the target compound as a diastereomer mixture.

LC-MS (Method 4): $R_t$=1.05 min; MS (ESIpos): m/z (%)=445.0 (100) [M+H]$^+$.

Method B:

(4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile (2.00 g, 4.67 mmol) was initially charged in methanol/water (4.4:1, ~40 ml), sodium periodate (1.90 g, 8.87 mmol; 1.9 eq.) was added and the mixture was stirred at 30° C. for 16 h. More sodium periodate (0.45 g, 2.10 mmol; 0.45 eq.) was then added, and the reaction was stirred at 50° C. for a further 4 h (monitored by HPLC). The reaction mixture was then added to saturated aqueous sodium bicarbonate solution (~200 ml) and extracted with ethyl acetate (4×50 ml). The combined organic phases were dried over sodium sulfate, filtered and concentrated under reduced pressure. The crude product was subjected to flash chromatography on silica gel (gradient cyclohexane→ethyl acetate). The target compound was obtained as a diastereomer mixture in the form of a colorless solid (2.18 g, quant.).

LC-MS (Method 9): $R_t$=1.98 min; MS (ESIpos): m/z (%)=402.0 (100), 445.0 (60) [M+H]$^+$; MS (ESIneg): m/z (%)=400.1 (100), 443.1 (40) [M−H]$^-$.

$^1$H-NMR (400 MHz, DMSO-d$_6$): δ=1.85 (2 s, 3H), 2.85 (2 s, 3H), 5.75 (2 s, 1H), 7.70-8.50 (m, 8H).

Example 19A ($R_S$,4S)-4-[4-Cyano-2-(methylsulfinyl)phenyl]-3,6-dimethyl-2-oxo-1-[3-(trifluoromethyl)phenyl]-1,2,3,4-tetrahydropyrimidine-5-carbonitrile and ($S_S$,4S)-4-[4-cyano-2-(methylsulfinyl)phenyl]-3,6-dimethyl-2-oxo-1-[3-(trifluoromethyl)phenyl]-1,2,3,4-tetrahydropyrimidine-5-carbonitrile (diastereomer mixture)

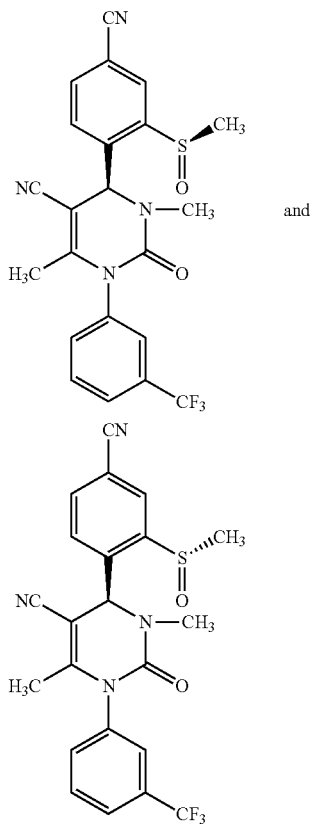

The reaction was carried out under argon. The diastereomer mixture of ($R_S$,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile and ($S_S$,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile (535 mg, 1.2 mmol) was initially charged in absolute THF (12 ml), and a 1 M solution of lithium hexamethyldisilazide (LiHMDS) in THF (1.45 ml; 1.2 eq.) was added at −78° C. After 20 min of stirring at −78° C., iodomethane (854 mg; 5 eq.) was added and the mixture was stirred for 16 h with gradual warming from −78° C. to RT. The reaction mixture was then concentrated under reduced pressure, saturated ammonium chloride solution (50 ml) was added and the mixture was then extracted with ethyl acetate (3×30 ml). The combined organic phases were dried over solid sodium sulfate, filtered and concentrated under reduced pressure and the residue was purified by preparative HPLC (column: Gromsil C-18 10 μm; mobile phase: acetonitrile/water+0.1% TFA 10:90→90:10). This gave the title compound as a solid (488 mg, 88% of theory).

LC-MS (Method 6): $R_t$=2.12 min; MS (ESIpos): m/z (%)=459.0 (100) [M+H]$^+$; MS (ESIneg): m/z (%)=456.9 (100) [M−H]$^-$.

$^1$H-NMR (400 MHz, DMSO-$d_6$): δ=1.80 (2 s, 3H), 2.65 (2 s, 3H), 2.90 (2 s, 3H), 5.80 (2 s, 1H), 7.70-8.20 (m, 6H), 8.45 (2 s, 1H).

Example 20A ($R_S$)—N-[(5-Cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide and ($S_S$)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide (diastereomer mixture)

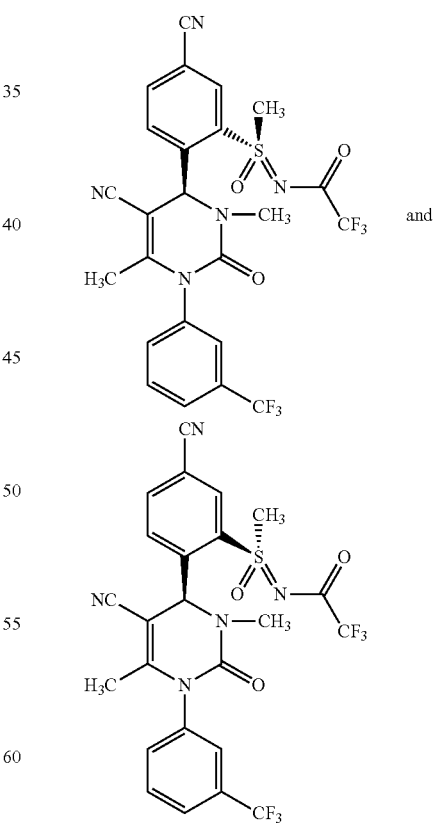

The reaction was carried out under argon. The diastereomer mixture of ($R_S$,4S)-4-[4-cyano-2-(methylsulfinyl)phenyl]-3,6-dimethyl-2-oxo-1-[3-(trifluoromethyl)phenyl]-1,2, 3,4-tetrahydropyrimidine-5-carbonitrile and (S$_S$,4S)-4-[4-cyano-2-(methylsulfinyl)phenyl]-3,6-dimethyl-2-oxo-1-[3-(trifluoromethyl)phenyl]-1,2,3,4-tetrahydropyrimidine-5-carbonitrile (488 mg, 1.1 mmol) was initially charged in dichloromethane (10 ml), and 2,2,2-trifluoroacetamide (241 mg, 2.13 mmol; 2.0 eq.), magnesium oxide (172 mg, 4.26 mmol; 4.0 eq.), rhodium(II) acetate dimer (24 mg, 53 μmol; 0.05 eq.) and (diacetoxyiodo)benzene (514 mg, 1.60 mmol; 1.5 eq.) were added in succession. The mixture was stirred at room temperature for 16 h. More 2,2,2-trifluoroacetamide (120 mg, 1.06 mmol; 1.0 eq.), magnesium oxide (86 mg, 2.13 mmol; 2.0 eq.), rhodium(II) acetate dimer (12 mg, 27 μmol; 0.025 eq.) and (diacetoxyiodo)benzene (257 mg, 798 μmol; 0.75 eq.) were then added, and the mixture was stirred at room temperature for a further 24 h. The reaction mixture was then filtered through kieselguhr, the filtrate was concentrated under reduced pressure and the residue was purified by preparative HPLC (column: Gromsil C-18 10 μm; mobile phase: acetonitrile/water+0.1% TFA 10:90→80:20). This gave the title compound as a diastereomer mixture in the form of a solid (160 mg, 25% of theory).

LC-MS (Method 4): R$_t$=1.35 min and 1.37 min; MS (ESIpos): m/z (%)=570.1 (100) [M+H]$^+$; MS (ESIneg): m/z (%)=567.9 (100) [M−H]$^-$.

Example 21A (R$_S$)—N-[(5-Cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide or (S$_S$)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide (diastereomer 1)

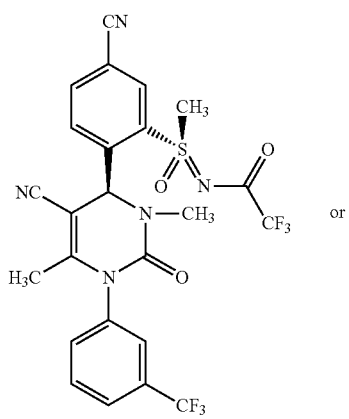

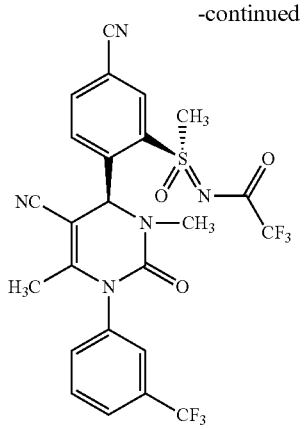

The diastereomer mixture of (R$_S$)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide and (S$_S$)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide (160 mg) was separated by flash chromatography on silica gel (mobile phase gradient cyclohexane→cyclohexane/ethyl acetate 45:55). Diastereomer 1 was obtained as initially-eluting fraction (yield: 52 mg).

LC-MS (Method 4): R$_t$=1.38 min; MS (ESIpos): m/z (%)=570.1 (100) [M+H]$^+$; MS (ESIneg):
m/z (%)=568.3 (100) [M−H]$^-$.

Example 22A (S$_S$)—N-[(5-Cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide or (R$_S$)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide (diastereomer 2)

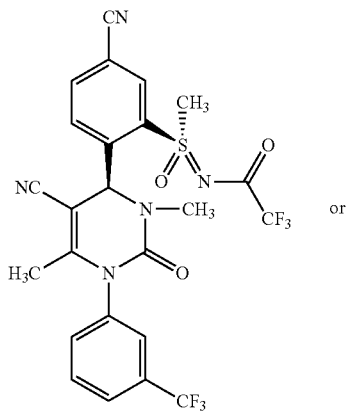
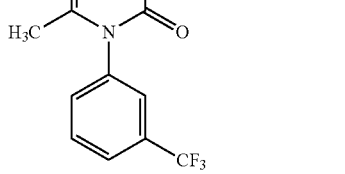

-continued

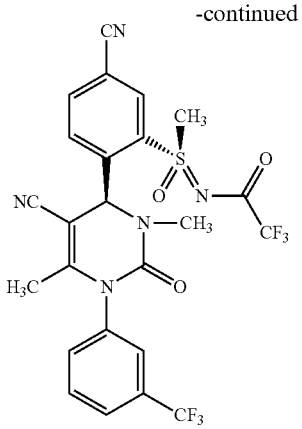

The diastereomer mixture of (R_S)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide and (S_S)—N-[(5-cyano-2-{(4S)-5-cyano-3,6-dimethyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide (160 mg) was separated by flash chromatography on silica gel (mobile phase gradient cyclohexane cyclohexane/ethyl acetate 45:55). Diastereomer 2 was obtained as later-eluting fraction (yield: 68 mg).

LC-MS (Method 4): R_f=1.35 min; MS (ESIpos): m/z (%)=570.1 (100) [M+H]$^+$; MS (ESIneg): m/z (%)=568.4 (100) [M−H]$^-$.

Example 23A (R_S)—N-[(5-Cyano-2-{(4S)-5-cyano-6-methyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide and (S_S)—N-[(5-cyano-2-{(4S)-5-cyano-6-methyl-2-oxo-1-[3-(trifluoromethyl)phenyl]-1,2,3,4-tetrahydropyrimidin-4-yl}phenyl)(methyl)oxido-$\lambda^6$-sulfanilidene]-2,2,2-trifluoroacetamide (diastereomer mixture)

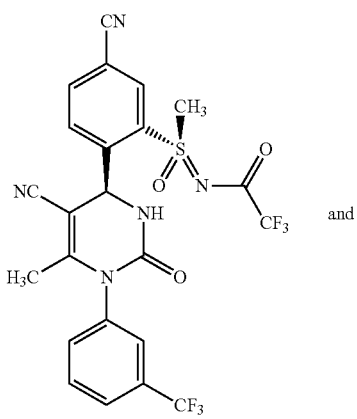 and

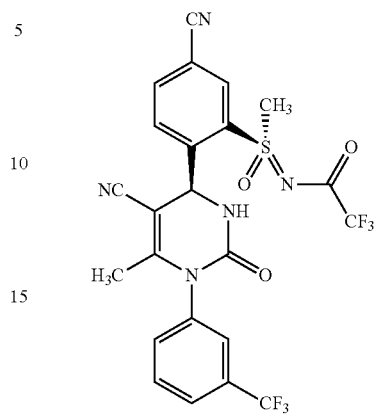

The reaction was carried out under argon. The diastereomer mixture of (R_S,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile and (S_S,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile (600 mg, 1.35 mmol) was initially charged in dichloromethane (13.5 ml), and 2,2,2-trifluoroacetamide (305 mg, 2.7 mmol; 2.0 eq.), magnesium oxide (217 mg, 5.4 mmol; 4.0 eq.), rhodium(II) acetate dimer (29.8 mg, 68 µmol; 0.05 eq.) and (diacetoxyiodo)benzene (652 mg, 2.03 mmol; 1.5 eq.) were added in succession. The mixture was stirred at room temperature for 16 h. More 2,2,2-trifluoroacetamide (152.6 mg, 1.35 mmol; 1.0 eq.), magnesium oxide (109 mg, 2.7 mmol; 2.0 eq.), rhodium(II) acetate dimer (15 mg, 34 µmol; 0.025 eq.) and (diacetoxyiodo)benzene (326 mg, 1013 µmol; 0.75 eq.) were then added and the mixture was stirred at room temperature for a further 3 h. The reaction mixture was then filtered through kieselguhr, the filtrate was concentrated under reduced pressure and the residue was subjected to flash chromatography on silica gel (gradient cyclohexane→ethyl acetate). This gave the title compound as diastereomer mixture in the form of a solid (485 mg, 65% of theory).

LC-MS (Method 4): R_f=1.28 min; MS (ESIpos): m/z (%)=556.0 (100) [M+H]$^+$.

$^1$H-NMR (400 MHz, DMSO-d_6): δ=1.85 (2 s, 3H), 4.00 (2 s, 3H), 6.50 (2 s, 1H), 7.70-8.55 (m, 8H).

Example 24A (R$_S$,4S)-4-[4-Cyano-2-(methylsulfinyl)phenyl]-6-methyl-3-(methylsulfonyl)-2-oxo-1-[3-(trifluoromethyl)phenyl]-1,2,3,4-tetrahydropyrimidine-5-carbonitrile and (S$_S$,4S)-4-[4-cyano-2-(methylsulfinyl)phenyl]-6-methyl-3-(methylsulfonyl)-2-oxo-1-[3-(trifluoromethyl)phenyl]-1,2,3,4-tetrahydropyrimidine-5-carbonitrile (diastereomer mixture)

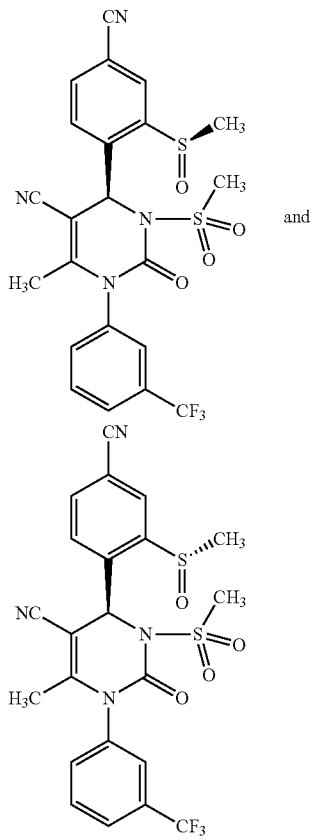

and

The reaction was carried out under argon. The diastereomer mixture of (R$_S$,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile and (S$_S$,4S)-4-[4-cyano-2-(methylsulfinyl)phenyl]-6-methyl-2-oxo-1-[3-(trifluoromethyl)phenyl]-1,2,3,4-tetrahydropyrimidine-5-carbonitrile (444.4 mg, 1000 μmol) was initially charged in THF (10 ml), and sodium hydride (60% in mineral oil; 56 mg, 1400 μmol) was added at 0° C. The mixture was warmed to RT and stirred for 20 min. A solution of methanesulfonyl chloride (160.4 mg, 1400 μmol; 1.4 eq.) in THF (5 ml) was then slowly added dropwise. After a reaction time of 16 h, more methanesulfonyl chloride (54 mg, 467 μmol; 0.47 eq.) was added and the mixture was stirred at RT for another 60 min. Saturated ammonium chloride solution (50 ml) was added, and the reaction mixture then extracted with ethyl acetate (3×30 ml). The combined organic phases were dried over solid sodium sulfate, filtered and concentrated under reduced pressure. The crude product was purified by preparative HPLC (column: Gromsil C-18 10 μm; mobile phase: acetonitrile/water+0.1% TFA 10:90→80:20). This gave the title compound as a colorless solid (245 mg, 47% of theory).

LC-MS (Method 6): R$_t$=2.20 min; MS (ESIpos): m/z (%)=522.9 (100) [M+H]$^+$; MS (ESIneg): m/z (%)=440.9 (100), 520.9 (100) [M−H]$^−$.

$^1$H-NMR (400 MHz, DMSO-d$_6$): δ=1.80 (2 s, 3H), 2.90 (2 s, 3H), ~3.40 (2 s, 3H), 6.40 (2 s, 1H), 7.75-8.20 (m, 6H), 8.50 (2 s, 1H).

Example 25A (R$_S$)—N-[(5-Cyano-2-{(4S)-5-cyano-6-methyl-3-(methylsulfonyl)-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide and (S$_S$)—N-[(5-cyano-2-{(4S)-5-cyano-6-methyl-3-(methylsulfonyl)-2-oxo-1-[3-(trifluoromethyl)phenyl]-1,2,3,4-tetrahydropyrimidin-4-yl}phenyl)(methyl)oxido-λ$^6$-sulfanilidene]-2,2,2-trifluoroacetamide (diastereomer mixture)

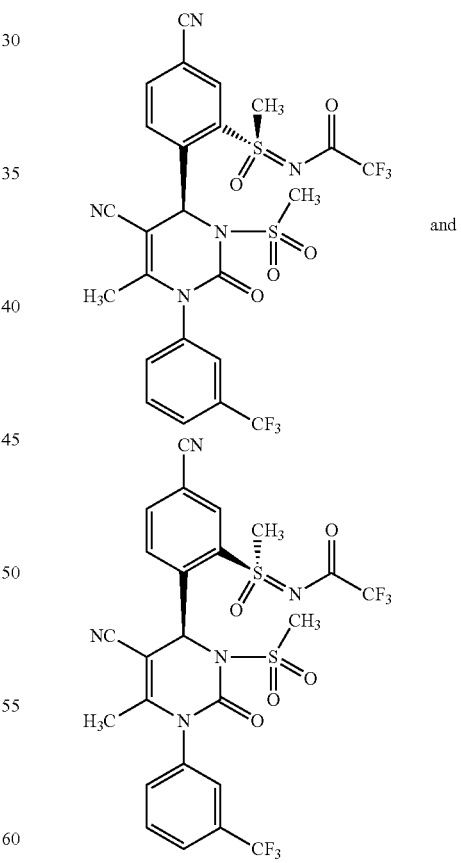

and

The reaction was carried out under argon. The diastereomer mixture of (R$_S$,4S)-4-[4-cyano-2-(methylsulfinyl)phenyl]-6-methyl-3-(methylsulfonyl)-2-oxo-1-[3-(trifluoromethyl)phenyl]-1,2,3,4-tetrahydropyrimidine-5-carbonitrile and (S$_S$,4S)-4-[4-cyano-2-(methylsulfinyl)phenyl]-6-methyl-3-(methylsulfonyl)-2-oxo-1-[3-(trifluoromethyl)phenyl]-1,2,3,4-tetrahydropyrimidine-5-carbonitrile (160 mg, 0.306 mmol) was initially charged in dichloromethane (3 ml), and 2,2,2-trifluoroacetamide (69 mg, 0.612 mmol; 2.0 eq.), magnesium oxide (49.4 mg, 1.225 mmol; 4.0 eq.), rhodium (II) acetate dimer (6.8 mg, 15 µmol; 0.05 eq.) and (diacetoxyiodo)benzene (147.9 mg, 0.459 mmol; 1.5 eq.) were added in succession. The mixture was stirred at room temperature for 16 h. More 2,2,2-trifluoroacetamide (34.6 mg, 0.306 mmol; 1.0 eq.), magnesium oxide (24.7 mg, 0.612 mmol; 2.0 eq.), rhodium(II) acetate dimer (3.4 mg, 8 µmol; 0.025 eq.) and (diacetoxyiodo)benzene (74 mg, 230 µmol; 0.75 eq.) were then added, and the mixture was stirred at room temperature for another 24 h. The reaction mixture was then filtered through kieselguhr, the filtrate was concentrated under reduced pressure and the residue was subjected to flash chromatography on silica gel (gradient cyclohexane→cyclohexane/ethyl acetate 1:2→ethyl acetate). This gave the title compound as diastereomer mixture in the form of a solid (25 mg, 8% of theory, 61% pure). This product was used without further work-up for the subsequent reaction.

LC-MS (Method 5): $R_t$=2.27 min; MS (ESIpos): m/z (%)=634.1 (100) [M+H]$^+$; MS (ESIneg): m/z (%)=632.1 (100) [M−H]$^−$.

Exemplary Embodiments

Example 1

5-Cyano-2-{(4S)-5-cyano-6-methyl-2-oxo-1-[3-(trifluoromethyl)phenyl]-1,2,3,4-tetrahydropyrimidin-4-yl}benzenesulfonamide

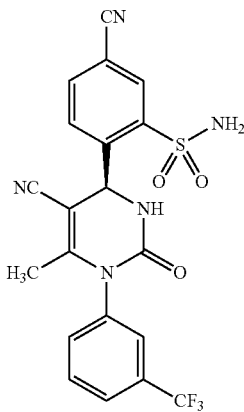 [SMILES: CC1=C(C#N)[C@@H](c2ccc(C#N)cc2S(N)(=O)=O)NC(=O)N1c1cccc(C(F)(F)F)c1]

At room temperature, a 0.5 M solution of ammonia in dioxane (25.79 ml, 12.9 mmol; 10 eq.) and triethylamine (130 mg, 1.3 mmol; 1 eq.) were added to 5-cyano-2-{(4S)-5-cyano-6-methyl-2-oxo-1-[3-(trifluoromethyl)phenyl]-1,2,3,4-tetrahydropyrimidin-4-yl}benzenesulfonyl chloride (3.10 g, content 20%, 1.29 mmol), and the mixture was stirred overnight. The reaction mixture was then concentrated under reduced pressure, water/acetonitrile (~10:1) was added to the residue and the solution was lyophilized. The substance obtained was dissolved in acetonitrile and then purified by preparative HPLC (column: Waters Sunfire C18, 5 µm; column dimensions: 250 mm×20 mm; detection: 240 nm; temperature: 28° C.; flow rate: 25 ml/min; injection volume: 500 µl; mobile phase: acetonitrile/0.2% trifluoroacetic acid 45:55). The title compound was obtained as a solid (0.155 g, 26% of theory).

LC-MS (Method 4): $R_t$=1.10 min; MS (ESIpos): m/z (%)=462.0 (100) [M+H]$^+$.

$^1$H-NMR (400 MHz, DMSO-d$_6$): δ=1.85 (s, 3H), 6.30 (s, 1H), 7.73-7.90 (m, 6H), 7.99 (d, 1H), 8.20-8.30 (m, 3H).

Example 2

5-Cyano-2-{(4S)-5-cyano-6-methyl-2-oxo-1-[3-(trifluoromethyl)phenyl]-1,2,3,4-tetrahydropyrimidin-4-yl}-N-methylbenzenesulfonamide

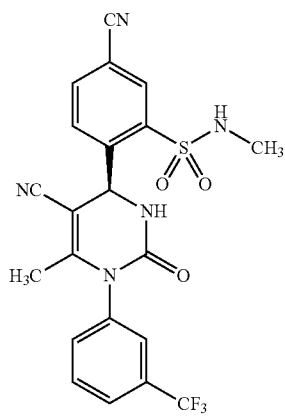

5-Cyano-2-{(4S)-5-cyano-6-methyl-2-oxo-1-[3-(trifluoromethyl)phenyl]-1,2,3,4-tetrahydropyrimidin-4-yl}benzenesulfonyl chloride (40 mg, 83 µmol) was dissolved in THF (5 ml), a 2 M solution of methylamine in THF (208 µl, 415 µmol; 5 eq.) was added at room temperature and the mixture was stirred overnight. The reaction mixture was then concentrated under reduced pressure and the residue was purified by preparative HPLC (column: Gromsil C-18, 10 µm; mobile phase: acetonitrile/water+0.1% TFA 10:90→90:10). This gave a colorless amorphous solid (14.3 mg, 36% of theory).

LC-MS (Method 6): $R_t$=2.29 min; MS (ESIpos): m/z (%)=476.0 (100) [M+H]$^+$.

$^1$H-NMR (400 MHz, DMSO-d$_6$): δ=1.85 (s, 3H), 2.55 (s, 3H), 6.30 (s, 1H), 7.70-8.00 (m, 5H), 8.20-8.30 (m, 4H).

Example 3

5-Cyano-2-{(4S)-5-cyano-6-methyl-2-oxo-1-[3-(trifluoromethyl)phenyl]-1,2,3,4-tetrahydropyrimidin-4-yl}-N,N-dimethylbenzenesulfonamide

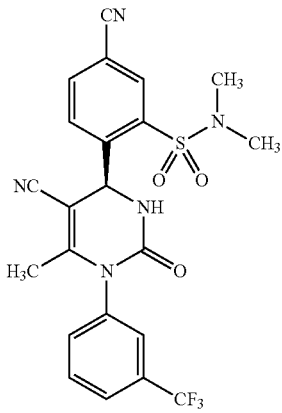

5-Cyano-2-{(4S)-5-cyano-6-methyl-2-oxo-1-[3-(trifluoromethyl)phenyl]-1,2,3,4-tetrahydropyrimidin-4-yl}benzenesulfonyl chloride (40 mg, 83 μmol) was dissolved in THF (5 ml), a 33% strength solution of dimethylamine in ethanol (37 μl, 208 μmol; 2.5 eq.) was added at room temperature and the mixture was stirred overnight. The reaction mixture was then concentrated under reduced pressure and the residue was purified by preparative HPLC (column: Gromsil C-18, 10 μm; mobile phase: acetonitrile/water+0.1% TFA 10:90→90:10). This gave a colorless amorphous solid (13.8 mg, 34% of theory).

LC-MS (Method 6): $R_t$=2.41 min; MS (ESIpos): m/z (%)=489.9 (100) [M+H]$^+$.

$^1$H-NMR (400 MHz, DMSO-d$_6$): δ=1.80 (s, 3H), 2.80 (s, 6H), 6.20 (s, 1H), 7.70-8.00 (m, 4H), 8.25-8.40 (m, 4H).

Example 4

(4S)-4-[4-Cyano-2-(morpholin-4-ylsulfonyl)phenyl]-6-methyl-2-oxo-1-[3-(trifluoromethyl)phenyl]-1,2,3,4-tetrahydropyrimidine-5-carbonitrile

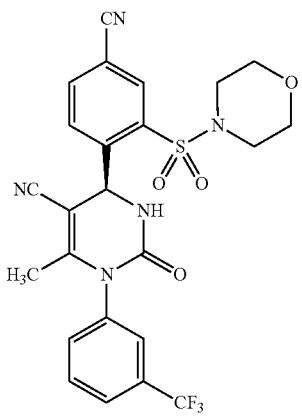

Under an atmosphere of argon protective gas, 5-cyano-2-{(4S)-5-cyano-6-methyl-2-oxo-1-[3-(trifluoromethyl)phenyl]-1,2,3,4-tetrahydropyrimidin-4-yl}benzenesulfonyl chloride (20 mg, 42 μmol) was dissolved in absolute dichloromethane (2.5 ml), morpholine (7.3 μl, 83 μmol; 2 eq.) was added at room temperature and the mixture was stirred overnight. The reaction mixture was then concentrated under reduced pressure and the residue was purified by preparative HPLC (column: Gromsil C-18, 10 μm; mobile phase: acetonitrile/water+0.1% TFA 10:90→90:10). This gave a colorless amorphous solid (8.6 mg, 35% of theory).

LC-MS (Method 6): $R_t$=2.39 min; MS (ESIpos): m/z (%)=532.0 (100) [M+H]$^+$.

$^1$H-NMR (400 MHz, DMSO-d$_6$): δ=1.80 (s, 3H), 3.10 (m, 2H), 3.15 (m, 2H), 3.70 (m, 4H), 6.20 (s, 1H), 7.70-8.00 (m, 4H), 8.25-8.40 (m, 4H).

Example 5

5-Cyano-2-{(4S)-5-cyano-3,6-dimethyl-2-oxo-1-[3-(trifluoromethyl)phenyl]-1,2,3,4-tetrahydropyrimidin-4-yl}-N,N-bis(2-hydroxyethyl)benzenesulfonamide

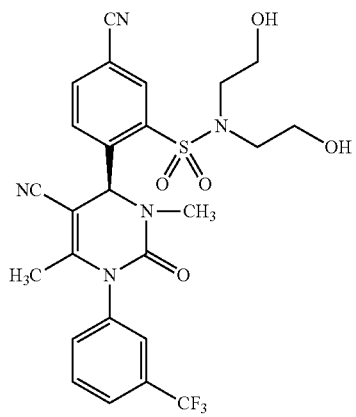 [SMILES: CC1=C(C#N)[C@@H](c2ccc(C#N)cc2S(=O)(=O)N(CCO)CCO)N(C)C(=O)N1c1cccc(C(F)(F)F)c1]

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (50 mg, 101 μmol) was dissolved in absolute THF (2.5 ml), diethanolamine (29 μl, 303 μmol; 3 eq.) and triethylamine (10.2 mg, 101 μmol; 1 eq.) were added at room temperature and the mixture was stirred overnight. The reaction mixture was then concentrated under reduced pressure and the residue was purified by preparative HPLC (column: Gromsil C-18, 10 μm; mobile phase: acetonitrile/water+0.1% TFA 10:90→90:10). This gave a colorless amorphous solid (4.9 mg, 9% of theory).

LC-MS (Method 4): $R_t$=1.11 min; MS (ESIpos): m/z (%)=564.0 (100) [M+H]$^+$; MS (ESIneg): m/z (%)=562.8 (100) [M-H]$^-$.

$^1$H-NMR (400 MHz, DMSO-d$_6$): δ=1.80 (s, 3H), 2.65 (s, 3H), 3.45 (m, 4H), 3.65 (m, 4H), 5.00 (br. s, 2H), 6.20 (s, 1H), 7.70-8.00 (m, 4H), 8.25-8.40 (m, 3H).

Example 6

(4S)-4-[4-Cyano-2-(morpholin-4-ylsulfonyl)phenyl]-3,6-dimethyl-2-oxo-1-[3-(trifluoromethyl)phenyl]-1,2,3,4-tetrahydropyrimidine-5-carbonitrile

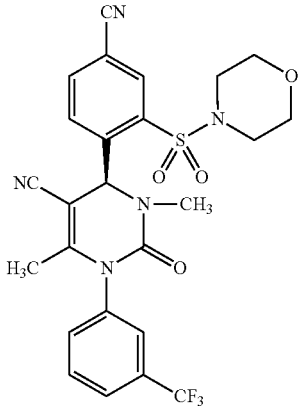

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (50 mg, 101 μmol) was dissolved in absolute THF (2.5 ml), morpholine (26 μl, 303 μmol; 3 eq.) and triethylamine (10.2 mg, 101 μmol; 1 eq.) were added at room temperature and the mixture was stirred overnight. The reaction mixture was then concentrated under reduced pressure and the residue was purified by preparative HPLC (column: Kromasil C-18, 5 μm; mobile phase: acetonitrile/water+0.1% TFA 10:90→90:10). This gave a colorless amorphous solid (44 mg, 80% of theory).

LC-MS (Method 4): $R_t$=1.27 min; MS (ESIpos): m/z (%)=545.9 (100) [M+H]$^+$; MS (ESIneg): m/z (%)=544.0 (100) [M−H]$^−$.

$^1$H-NMR (400 MHz, DMSO-d$_6$): δ=1.80 (s, 3H), 2.70 (s, 3H), 3.30 (m, 4H), 3.70 (m, 4H), 6.20 (s, 1H), 7.70-8.05 (m, 4H), 8.25-8.40 (m, 3H).

Example 7

5-Cyano-2-{(4S)-5-cyano-3,6-dimethyl-2-oxo-1-[3-(trifluoromethyl)phenyl]-1,2,3,4-tetrahydropyrimidin-4-yl}-N-(morpholin-4-yl)benzenesulfonamide Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (50 mg, 101 μmol) was dissolved in absolute THF (2.5 ml), N-aminomorpholine (29 μl, 303 μmol; 3 eq.) and triethylamine (10.2 mg, 101 μmol; 1 eq.) were added at room temperature and the mixture was stirred overnight. The reaction mixture was then concentrated under reduced pressure and the residue was purified by preparative HPLC (column: Kromasil C-18, 5 μm; mobile phase: acetonitrile/water+0.1% TFA 10:90→90:10). This gave a colorless amorphous solid (38 mg, 67% of theory).

LC-MS (Method 5): $R_t$=1.98 min; MS (ESIpos): m/z (%)=101.0 (100), 561.2 (15) [M+H]$^+$; MS (ESIneg): m/z (%)=459.1 (100), 475.1 (60), 559.2 (30) [M−H]$^−$.

$^1$H-NMR (400 MHz, DMSO-d$_6$): δ=1.80 (s, 3H), 2.60 (m, 4H), 2.75 (s, 3H), 3.50 (br. s, 4H), 6.50 (s, 1H), 7.70-8.00 (m, 4H), 8.10-8.40 (m, 4H).

Example 8

5-Cyano-2-{(4S)-5-cyano-3,6-dimethyl-2-oxo-1-[3-(trifluoromethyl)phenyl]-1,2,3,4-tetrahydropyrimidin-4-yl}-N,N-dimethylbenzenesulfonamide Under an atmosphere of argon protective gas, 5-cyano-2-{(4S)-5-cyano-6-methyl-2-oxo-1-[3-(trifluoromethyl)phenyl]-1,2,3,4-tetrahydropyrimidin-4-yl}-N,N-dimethylbenzene sulfonamide (50 mg, 108 μmol) was initially charged in absolute THF (4.5 ml), and a 1 M solution of lithium hexamethyldisilazide (LiHMDS) in THF (130 μl, 130 μmol; 1.2 eq.) was added at −78° C. After 30 min of stirring, iodomethane (77 mg, 542 μmol; 5 eq.) in THF (1 ml) was added, and the mixture was stirred for 16 h with gradual warming from −78° C. to RT. A little acetic acid was then added, and the reaction mixture was concentrated under reduced pressure. The residue was purified by preparative HPLC (column: Gromsil C-18; mobile phase: acetonitrile/water+0.1% TFA 10:90→90:10). This gave a colorless amorphous solid (7.6 mg, 14% of theory).

LC-MS (Method 4): $R_t$=1.29 min; MS (ESIpos): m/z (%)=504.1 (100) [M+H]$^+$; MS (ESIneg): m/z (%)=502.2 (100) [M−H]$^−$.

Example 9

5-Cyano-2-{(4S)-5-cyano-3,6-dimethyl-2-oxo-1-[3-(trifluoromethyl)phenyl]-1,2,3,4-tetrahydropyrimidin-4-yl}-N-methylbenzenesulfonamide

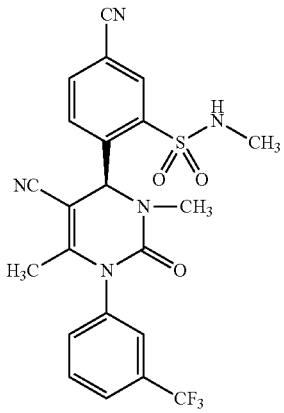

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (30 mg, 61 µmol) was dissolved in absolute THF (2 ml), a 2 M solution of methylamine in THF (91 µl, 182 µmol; 3 eq.) and triethylamine (6.1 mg, 61 µmol; 1 eq.) were added at room temperature and the mixture was stirred for 3 h. The reaction mixture was then concentrated under reduced pressure and the residue was purified by preparative HPLC (column: Gromsil C-18; mobile phase: acetonitrile/water+0.1% TFA 10:90→90:10). This gave a colorless amorphous solid (25 mg, 83% of theory).

LC-MS (Method 4): $R_t$=1.21 min; MS (ESIpos): m/z (%)=490.1 (100) [M+H]$^+$; MS (ESIneg): m/z (%)=488.1 (100) [M−H]$^-$.

$^1$H-NMR (400 MHz, DMSO-d$_6$): δ=1.80 (s, 3H), 2.60 (d, 3H), 2.65 (s, 3H), 6.25 (s, 1H), 7.70-8.30 (m, 8H).

Example 10

5-Cyano-2-{(4S)-5-cyano-3,6-dimethyl-2-oxo-1-[3-(trifluoromethyl)phenyl]-1,2,3,4-tetrahydropyrimidin-4-yl}benzenesulfonamide

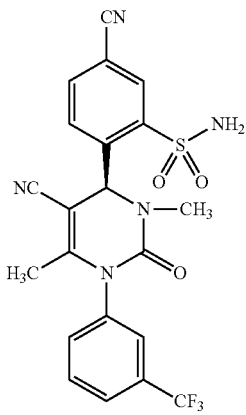 [SMILES: CC1=C(C#N)[C@@H](c2ccc(C#N)cc2S(N)(=O)=O)N(C)C(=O)N1c1cccc(C(F)(F)F)c1]

Under an atmosphere of argon protective gas, a 0.5 M solution of ammonia in dioxane (4000 µl, 2021 µmol; 10 eq.) and triethylamine (20.4 mg, 202 µmol; 1 eq.) were added to 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (100 mg, 202 µmol) at room temperature, and the mixture was stirred for 3 h. The reaction mixture was then concentrated under reduced pressure and the residue was purified by preparative HPLC (column: Gromsil C-18; mobile phase: acetonitrile/water+0.1% TFA 10:90→90:10). This gave a colorless amorphous solid (56 mg, 58% of theory).

LC-MS (Method 4): $R_t$=1.14 min; MS (ESIpos): m/z (%)=476.0 (100) [M+H]$^+$; MS (ESIneg): m/z (%)=473.9 (100) [M−H]$^-$.

$^1$H-NMR (400 MHz, DMSO-d$_6$): δ=1.80 (s, 3H), 2.70 (s, 3H), 6.25 (s, 1H), 7.60-8.30 (m, 9H).

Example 11

5-Cyano-2-{(4S)-5-cyano-3,6-dimethyl-2-oxo-1-[3-(trifluoromethyl)phenyl]-1,2,3,4-tetrahydropyrimidin-4-yl}-N-(2-hydroxyethyl)benzenesulfonamide

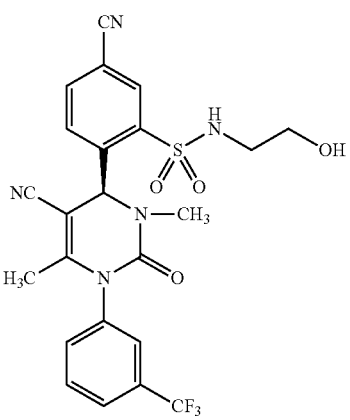 [SMILES: CC1=C(C#N)[C@@H](c2ccc(C#N)cc2S(=O)(=O)NCCO)N(C)C(=O)N1c1cccc(C(F)(F)F)c1]

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (50 mg, 101 µmol) was dissolved in absolute THF (2.5 ml), ethanolamine (18 µl, 303 µmol; 3 eq.) and triethylamine (10.2 mg, 101 µmol; 1 eq.) were added at room temperature and the mixture was stirred overnight. The reaction mixture was then concentrated under reduced pressure and the residue was purified by preparative HPLC (column: Kromasil C-18, 5 µm; mobile phase: acetonitrile/water+0.1% TFA 10:90→90:10). This gave a colorless amorphous solid (43 mg, 81% of theory).

LC-MS (Method 4): $R_t$=1.13 min; MS (ESIpos): m/z (%)=520.0 (100) $[M+H]^+$.

$^1$H-NMR (400 MHz, DMSO-$d_6$): δ=1.80 (s, 3H), 2.65 (s, 3H), 3.00 (m, 2H), 3.45 (m, 2H), 6.30 (s, 1H), 7.70-8.30 (m, 7H), 8.35 (s, 1H), 8.45 (t, 1H).

Example 12

5-Cyano-2-{(4S)-5-cyano-3,6-dimethyl-2-oxo-1-[3-(trifluoromethyl)phenyl]-1,2,3,4-tetrahydropyrimidin-4-yl}-N-(3-hydroxypropyl)benzenesulfonamide

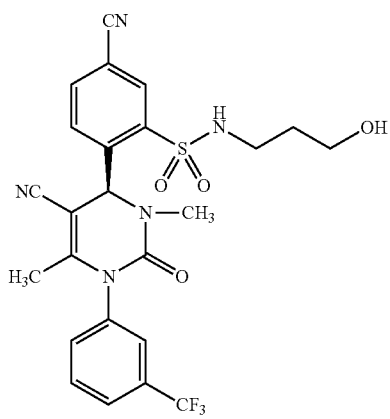 [SMILES: CC1=C(C#N)[C@@H](c2ccc(C#N)cc2S(=O)(=O)NCCCO)N(C)C(=O)N1c1cccc(C(F)(F)F)c1]

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (25 mg, 51 μmol) was dissolved in absolute THF (1.5 ml), 3-aminopropanol (11 μl, 152 μmol; 3 eq.) and triethylamine (5.1 mg, 51 μmol; 1 eq.) were added at room temperature and the mixture was stirred overnight. The reaction mixture was then concentrated under reduced pressure and the residue was purified by preparative HPLC (column: Kromasil C-18, 5 μm; mobile phase: acetonitrile/water+0.1% TFA 10:90→90:10). This gave a colorless amorphous solid (18 mg, 67% of theory).

LC-MS (Method 4): $R_t$=1.14 min; MS (ESIpos): m/z (%)=534.1 (100) $[M+H]^+$; MS (ESIneg): m/z (%)=532.1 (100) $[M-H]^-$.

Example 13

$N^2$-[(5-Cyano-2-{(4S)-5-cyano-3,6-dimethyl-2-oxo-1-[3-(trifluoromethyl)phenyl]-1,2,3,4-tetrahydropyrimidin-4-yl}phenyl)sulfonyl]glycinamide

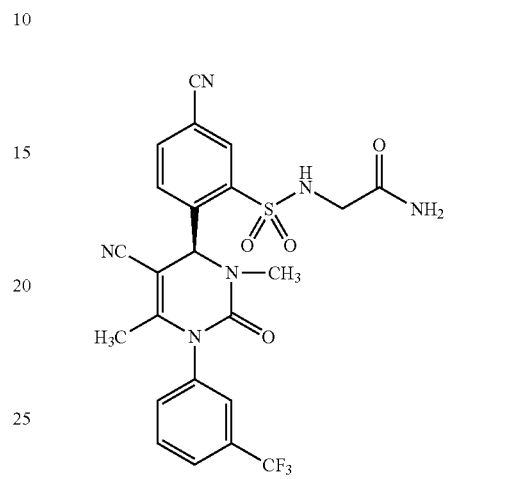

Under an atmosphere of argon protective gas, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (50 mg, 101 μmol) was dissolved in absolute THF (2.5 ml), glycinamide hydrochloride (57 mg, 505 μmol; 5 eq.) and triethylamine (102 mg, 1010 μmol; 10 eq.) were added at room temperature and the mixture was stirred overnight. The reaction mixture was then concentrated under reduced pressure and the residue was purified by preparative HPLC (column: Gromsil C-18, 10 μm; mobile phase: acetonitrile/water+0.1% TFA 10:90→90:10). This gave a colorless amorphous solid (39.2 mg, 73% of theory).

LC-MS (Method 4): $R_t$=1.09 min; MS (ESIpos): m/z (%)=532.9 (100) $[M+H]^+$.

$^1$H-NMR (400 MHz, DMSO-$d_6$): δ=1.80 (s, 3H), 2.65 (s, 3H), 3.60 (m, 2H), 6.30 (s, 1H), 7.15 (s, 1H), 7.40 (s, 1H), 7.70-8.30 (m, 6H), 8.40 (s, 1H), 8.70 (t, 1H).

General Procedure for Preparing Other Sulfonamide Derivatives:

The amine component in question (0.1 mmol) was initially charged in 1,2-dichloroethane (0.2 ml). N,N-Diisopropylethylamine (25.8 mg, 0.2 mmol) and 5-cyano-2-{(4S)-5-cyano-6-methyl-2-oxo-1-[3-(trifluoromethyl)phenyl]-1,2,3,4-tetrahydropyrimidin-4-yl}benzenesulfonyl chloride (48.1 mg, 0.1 mmol), dissolved in 1,2-dichloroethane (0.3 ml), were then added. The mixture was stirred at room temperature overnight. The dichloroethane was then evaporated in a vacuum centrifuge. The residue was dissolved in dimethyl sulfoxide (0.5 ml) and purified by preparative HPLC/MS.

The compounds listed in the table below were obtained according to this procedure:

| Example | Structure/Name | Analytical data |
|---|---|---|
| 14 | 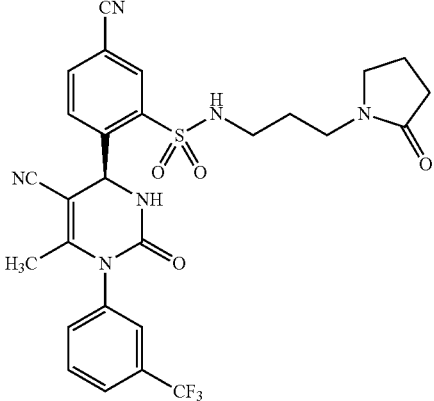 [SMILES: CC1=C(C#N)[C@@H](c2ccc(C#N)cc2S(=O)(=O)NCCCN2CCCC2=O)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-(tetrahydro-pyrimidin-4-yl}-N-[3-(2-oxopyrrolidin-1-yl)-propyl]benzenesulfonamide | MS (ESIpos): m/z = 587 (M + H)$^+$<br>LC-MS (Method 11):<br>R$_t$ = 1.97 min.<br>$^1$H-NMR (400 MHz, DMSO-d$_6$):<br>δ = 1.64 (quin, J = 7.09 Hz, 2H),<br>1.84 (s, 3H), 1.86-1.94 (m, 2H),<br>2.13-2.22 (m, 2H), 2.81-2.90 (m, 2H), 3.10-3.24 (m, 2H), 6.29 (s, 1H), 7.74 (br. s, 2H), 7.79-7.86 (m, 1H), 7.90-7.98 (m, 1H), 8.11-8.19 (m, 2H), 8.25 (s, 1H), 8.29 (s, 4H). |
| 15 | 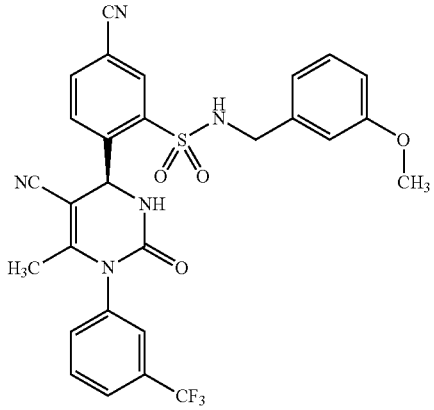<br>5-cyano-2-{(4S)-5-cyano-6-methyl-2-oxo-1-[3-(trifluoromethyl)phenyl]-1,2,3,4-tetrahydropyrimidin-4-yl}-N-(3-methoxybenzyl)benzenesulfonamide | MS (ESIpos): m/z = 582 (M + H)$^+$<br>LC-MS (Method 11):<br>R$_t$ = 2.17 min.<br>$^1$H-NMR (400 MHz, DMSO-d$_6$):<br>δ = 1.85 (s, 3H), 3.72 (s, 3H), 4.13 (br. s, 2H), 6.34 (s, 1H), 6.72-6.93 (m, 3H), 7.22 (t, J = 7.83 Hz, 1H), 7.74 (d, J = 4.89 Hz, 2H), 7.78-7.87 (m, 1H), 7.87-7.98 (m, 1H), 8.17 (s, 1H), 8.25 (s, 3H), 8.67 (br. s, 1H). |
| 16 | 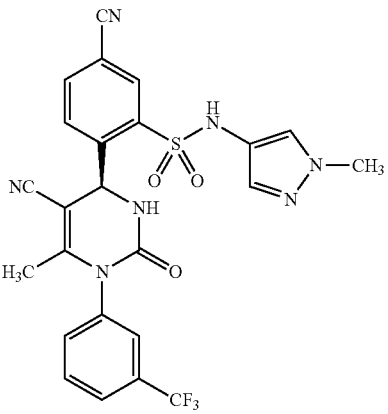<br>5-cyano-2-{(4S)-5-cyano-6-methyl-2-oxo-1-[3-(trifluoromethyl)phenyl]-1,2,3,4-tetrahydropyrimidin-4-yl}-N-(1-methyl-1H-pyrazol-4-yl)benzenesulfonamide | MS (ESIpos): m/z = 542 (M + H)$^+$<br>LC-MS (Method 11):<br>R$_t$ = 1.94 min. |

-continued

| Example | Structure/Name | Analytical data |
|---|---|---|
| 17 | 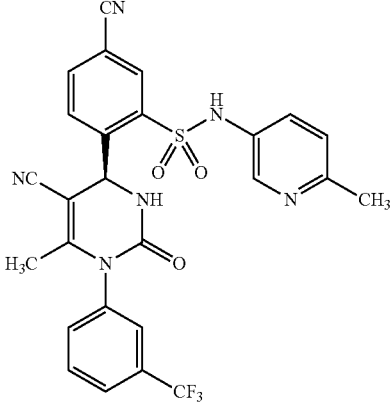<br>5-cyano-2-{(4S)-5-cyano-6-methyl-2-oxo-1-[3-(trifluoromethyl)phenyl]-1,2,3,4-tetrahydropyrimidin-4-yl}-N-(6-methylpyridin-3-yl)benzenesulfonamide | MS (ESIpos): m/z = 553 (M + H)$^+$<br>LC-MS (Method 11):<br>$R_t$ = 1.79 min. |
| 18 | 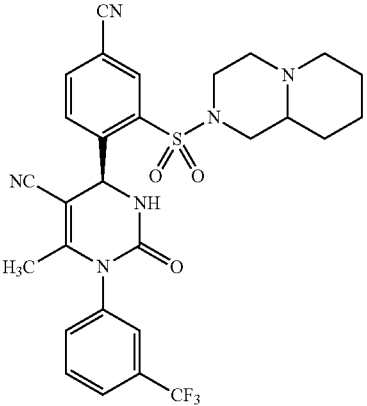 [SMILES: CC1=C(C#N)[C@@H](c2ccc(C#N)cc2S(=O)(=O)N2CCN3CCCCC3C2)NC(=O)N1c1cccc(C(F)(F)F)c1]<br>(4S)-4-[4-cyano-2-(octahydro-2H-pyrido[1,2-a]-pyrazin-2-ylsulfonyl)phenyl]-6-methyl-2-oxo-1-[3-(trifluoromethyl)phenyl]-1,2,3,4-tetrahydro-pyrimidine-5-carbonitrile | MS (ESIpos): m/z = 585 (M + H)$^+$<br>LC-MS (Method 11):<br>$R_t$ = 1.55 min.<br>$^1$H-NMR (400 MHz, DMSO-$d_6$):<br>δ = 0.93-1.14 (m, 1H), 1.22 (dd, J = 9.05, 4.65 Hz, 1H), 1.31-1.46 (m, 1H), 1.56 (d, J = 11.74 Hz, 2H), 1.65 (br. s, 1H), 1.82 (s, 3H), 1.88-2.04 (m, 2H), 2.08-2.30 (m, 2H), 2.63-2.90 (m, 3H), 3.52 (t, J = 11.00 Hz, 1H), 3.63 (t, J = 11.74 Hz, 1H), 6.21 (d, J = 6.85 Hz, 1H), 7.66-7.78 (m, 2H), 7.82 (d, J = 6.85 Hz, 1H), 7.94 (br. s, 1H), 8.20-8.43 (m, 4H). |
| 19 | 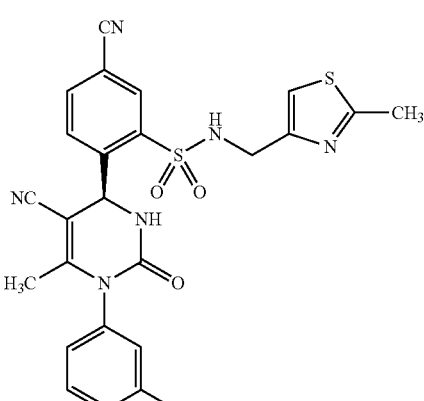<br>5-cyano-2-{(4S)-5-cyano-6-methyl-2-oxo-1-[3-(trifluoromethyl)phenyl]-1,2,3,4-tetrahydropyrimidin-4-yl}-N-[(2-methyl-1,3-thiazol-4-yl)methyl]-benzenesulfonamide | MS (ESIpos): m/z = 573 (M + H)$^+$<br>LC-MS (Method 11):<br>$R_t$ = 2.09 min. |

| Example | Structure/Name | Analytical data |
|---|---|---|
| 20 | 5-cyano-2-{(4S)-5-cyano-6-methyl-2-oxo-1-[3-(trifluoromethyl)phenyl]-1,2,3,4-tetrahydropyrimidin-4-yl}-N-[2-oxo-2-(piperidin-1-yl)ethyl]benzenesulfonamide | MS (ESIpos): m/z = 587 (M + H)+<br>LC-MS (Method 11):<br>$R_t$ = 2.13 min. |
| 21 | 5-cyano-2-{(4S)-5-cyano-6-methyl-2-oxo-1-[3-(trifluoromethyl)phenyl]-1,2,3,4-tetrahydropyrimidin-4-yl}-N-[(1-methylpyrrolidin-3-yl)methyl]-benzenesulfonamide | MS (ESIpos): m/z = 559 (M + H)+<br>LC-MS (Method 11):<br>$R_t$ = 1.51 min. |
| 22 | N-(2-{[(5-cyano-2-{(4S)-5-cyano-6-methyl-2-oxo-1-[3-(trifluoromethyl)phenyl]-1,2,3,4-tetrahydro-pyrimidin-4-yl}phenyl)sulfonyl]amino}ethyl)-acetamide | MS (ESIpos): m/z = 547 (M + H)+<br>LC-MS (Method 11):<br>$R_t$ = 1.86 min. |

| Example | Structure/Name | Analytical data |
|---|---|---|
| 23 | 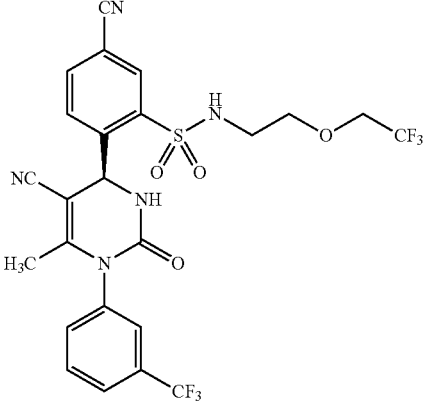 [SMILES: CC1=C(C#N)[C@@H](c2ccc(C#N)cc2S(=O)(=O)NCCOCC(F)(F)F)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-tetrahydropyrimidin-4-yl}-N-[2-(2,2,2-trifluoroethoxy)ethyl]-benzenesulfonamide | MS (ESIpos): m/z = 588 (M + H)$^+$<br>LC-MS (Method 11):<br>R$_t$ = 2.15 min. |
| 24 | 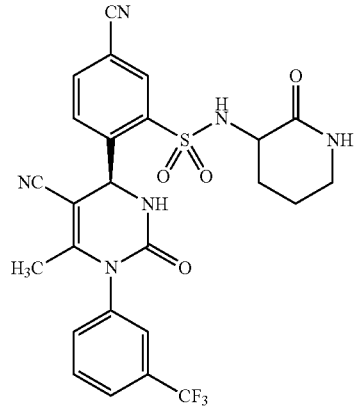 [SMILES: CC1=C(C#N)[C@@H](c2ccc(C#N)cc2S(=O)(=O)NC2CCCNC2=O)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-tetrahydropyrimidin-4-yl}-N-(2-oxopiperidin-3-yl)-benzenesulfonamide | MS (ESIpos): m/z = 559 (M + H)$^+$<br>LC-MS (Method 11):<br>R$_t$ = 1.99 min. |
| 25 | 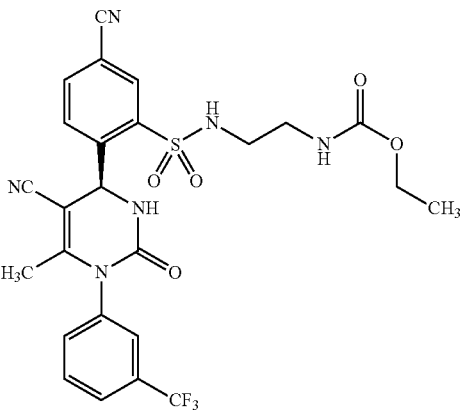 [SMILES: CCOC(=O)NCCNS(=O)(=O)c1cc(C#N)ccc1[C@H]1NC(=O)N(c2cccc(C(F)(F)F)c2)C(C)=C1C#N]<br>ethyl (2-{[(5-cyano-2-{(4S)-5-cyano-6-methyl-2-oxo-1-[3-(trifluoromethyl)phenyl]-1,2,3,4-tetrahydropyrimidin-4-yl}phenyl)sulfonyl]amino}ethyl)carbamate | MS (ESIpos): m/z = 577 (M + H)$^+$<br>LC-MS (Method 11):<br>R$_t$ = 2.01 min. |

| Example | Structure/Name | Analytical data |
|---|---|---|
| 26 | 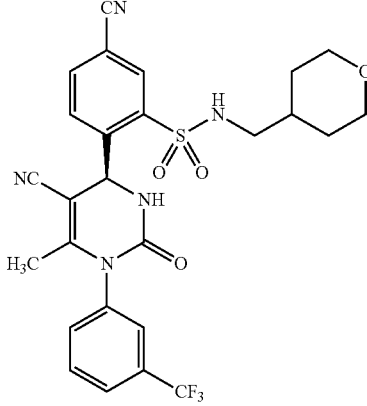<br>5-cyano-2-{(4S)-5-cyano-6-methyl-2-oxo-1-[3-(trifluoromethyl)phenyl]-1,2,3,4-tetrahydropyrimidin-4-yl}-N-(tetrahydro-2H-pyran-4-ylmethyl)-benzenesulfonamide | MS (ESIpos): m/z = 560 (M + H)$^+$<br>LC-MS (Method 11):<br>$R_t$ = 2.03 min.<br>$^1$H-NMR (400 MHz, DMSO-$d_6$):<br>δ = 1.00-1.22 (m, 2H), 1.59 (d, J = 13.21 Hz, 2H), 1.62-1.74 (m, 1H), 1.84 (s, 3H), 2.71-2.84 (m, 2H), 3.18-3.27 (m, 2H), 3.67-3.92 (m, 2H), 6.31 (s, 1H), 7.74 (d, J = 4.40 Hz, 2H), 7.82 (d, J = 3.42 Hz, 1H), 7.93 (br. s, 1H), 8.07-8.21 (m, 2H), 8.26 (d, J = 8.31 Hz, 3H). |
| 27 | 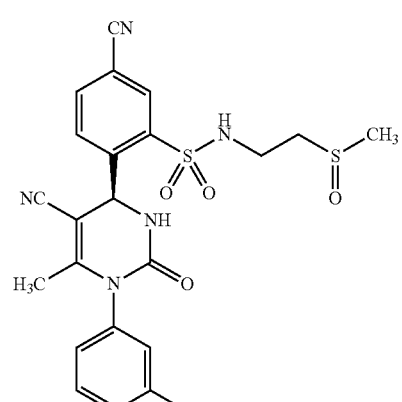<br>5-cyano-2-{(4S)-5-cyano-6-methyl-2-oxo-1-[3-(trifluoromethyl)phenyl]-1,2,3,4-tetrahydropyrimidin-4-yl}-N-[2-(methylsulfinyl)ethyl]benzenesulfonamide | MS (ESIpos): m/z = 552 (M + H)$^+$<br>LC-MS (Method 11):<br>$R_t$ = 1.83 min. |
| 28 | 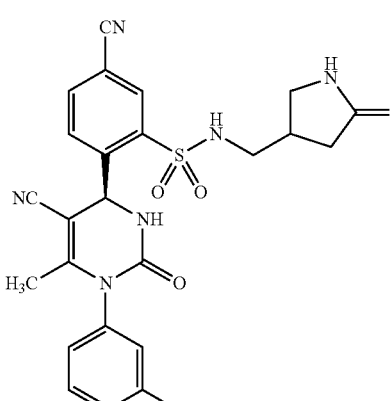<br>5-cyano-2-{(4S)-5-cyano-6-methyl-2-oxo-1-[3-(trifluoromethyl)phenyl]-1,2,3,4-tetrahydropyrimidin-4-yl}-N-[(5-oxopyrrolidin-3-yl)methyl]-benzenesulfonamide | MS (ESIpos): m/z = 559 (M + H)$^+$<br>LC-MS (Method 11):<br>$R_t$ = 1.83 min. |

| Example | Structure/Name | Analytical data |
|---|---|---|
| 29 | 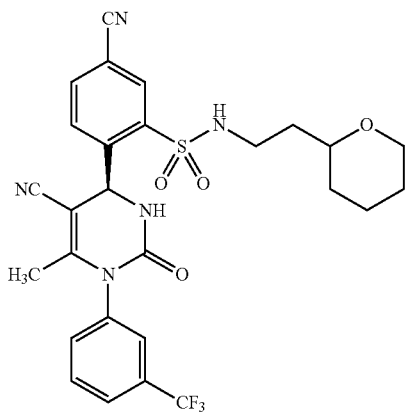 [SMILES: CC1=C(C#N)[C@@H](c2ccc(C#N)cc2S(=O)(=O)NCCC2CCCCO2)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-tetrahydropyrimidin-4-yl}-N-[2-(tetrahydro-2H-pyran-2-yl)ethyl]-benzenesulfonamide | MS (ESIpos): m/z = 574 (M + H)⁺<br>LC-MS (Method 11):<br>$R_t$ = 2.18 min.<br>¹H-NMR (400 MHz, DMS0-$d_6$):<br>δ = 1.13 (br. s, 1H), 1.41 (br. s, 3H), 1.46-1.64 (m, 3H), 1.72 (br. s, 1H), 1.84 (s, 3H), 2.94 (br. s, 2H), 3.25 (br. s, 3H), 3.68-3.89 (m, 1H), 6.29 (s, 1H), 7.74 (d, J = 4.40 Hz, 2H), 7.82 (d, J = 2.93 Hz, 1H), 7.88-8.00 (m, 1H), 8.04-8.17 (m, 1H), 8.26 (d, J = 15.16 Hz, 3H). |
| 30 | 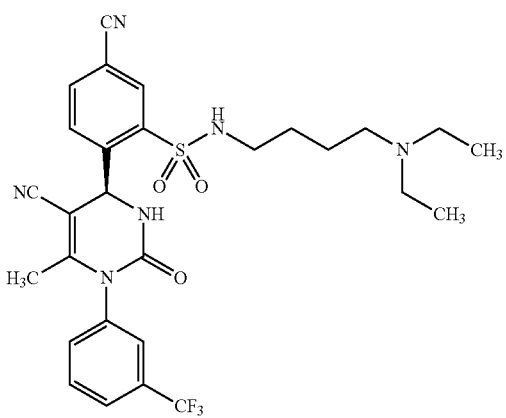 [SMILES: CCN(CC)CCCCNS(=O)(=O)c1cc(C#N)ccc1[C@H]1NC(=O)N(c2cccc(C(F)(F)F)c2)C(C)=C1C#N]<br>5-cyano-2-{(4S)-5-cyano-6-methyl-2-oxo-1-[3-(trifluoromethyl)phenyl]-1,2,3,4-tetrahydropyrimidin-4-yl}-N-[4-(diethylamino)-butyl]benzenesulfonamide | MS (ESIpos): m/z = 589 (M + H)⁺<br>LC-MS (Method 11):<br>$R_t$ = 1.55 min. |
| 31 | 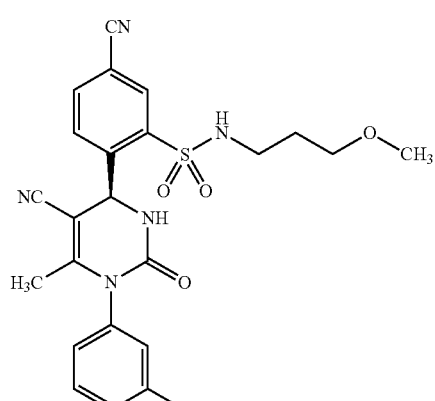<br>5-cyano-2-{(4S)-5-cyano-6-methyl-2-oxo-1-[3-(trifluoromethyl)phenyl]-1,2,3,4-tetrahydropyrimidin-4-yl}-N-(3-methoxypropyl)benzenesulfonamide | MS (ESIpos): m/z = 533 (M + H)⁺<br>LC-MS (Method 11):<br>$R_t$ = 2.05 min.<br>¹H-NMR (400 MHz, DMS0-$d_6$):<br>δ = 1.68 (quin, J = 6.60 Hz, 2H), 1.84 (s, 3H), 2.93 (q, J = 6.36 Hz, 2H), 3.20 (s, 3H), 6.29 (s, 1H), 7.74 (d, J = 4.40 Hz, 2H), 7.82 (d, J = 3.42 Hz, 1H), 7.92 (br. s, 1H), 8.08-8.16 (m, 2H), 8.24 (s, 2H), 8.28 (s, 3H). |

| Example | Structure/Name | Analytical data |
|---|---|---|
| 32 | 5-cyano-2-{(4S)-5-cyano-6-methyl-2-oxo-1-[3-(trifluoromethyl)phenyl]-1,2,3,4-tetrahydropyrimidin-4-yl}-N-[2-(1H-1,2,3-triazol-1-yl)ethyl]-benzenesulfonamide | MS (ESIpos): m/z = 557 (M + H)⁺<br>LC-MS (Method 11):<br>R$_t$ = 1.91 min.<br>¹H-NMR (400 MHz, DMSO-d$_6$):<br>δ = 1.70-1.89 (m, 3H), 1.83 (s, 3H), 3.36-3.43 (m, 2H), 4.50 (t, J = 6.11 Hz, 2H), 6.25 (s, 1H), 7.74 (s, 7H), 7.83 (br. s, 3H), 7.88-8.00 (m, 2H), 8.12 (s, 3H), 8.16 (d, J = 0.98 Hz, 2H), 8.23 (s, 2H), 8.29 (s, 3H), 8.41-8.56 (m, 1H). |
| 33 | 5-cyano-2-{(4S)-5-cyano-6-methyl-2-oxo-1-[3-(trifluoromethyl)phenyl]-1,2,3,4-tetrahydropyrimidin-4-yl}-N-[(1-methyl-1H-imidazol-2-yl)methyl]-benzenesulfonamide | MS (ESIpos): m/z = 556 (M + H)⁺<br>LC-MS (Method 11):<br>R$_t$ = 1.51 min. |
| 34 | 5-cyano-2-{(4S)-5-cyano-6-methyl-2-oxo-1-[3-(trifluoromethyl)phenyl]-1,2,3,4-tetrahydropyrimidin-4-yl}-N-(tetrahydrofuran-3-ylmethyl)-benzenesulfonamide | MS (ESIpos): m/z = 546 (M + H)⁺<br>LC-MS (Method 11):<br>R$_t$ = 2.00 min.<br>¹H-NMR (400 MHz, DMSO-d$_6$):<br>δ = 1.43-1.64 (m, 1H), 1.84 (s, 3H), 1.87-1.99 (m, 1H), 2.25-2.41 (m, 1H), 2.87 (d, J = 5.38 Hz, 2H), 3.37-3.48 (m, 1H), 3.51-3.63 (m, 1H), 3.62-3.78 (m, 3H), 6.30 (s, 1H), 7.74 (d, J = 3.91 Hz, 2H), 7.77-7.87 (m, 1H), 7.93 (br. s, 1H), 8.27 (d, J = 10.76 Hz, 4H). |

| Example | Structure/Name | Analytical data |
|---|---|---|
| 35 | 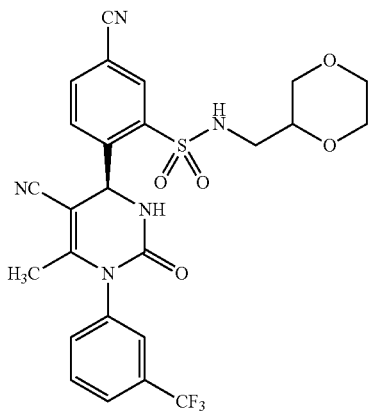 [SMILES: CC1=C(C#N)[C@@H](c2ccc(C#N)cc2S(=O)(=O)NCC2COCCO2)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-tetrahydropyrimidin-4-yl}-N-(1,4-dioxan-2-ylmethyl)-benzenesulfonamide | MS (ESIpos): m/z = 562 (M + H)$^+$<br>LC-MS (Method 11):<br>R$_t$ = 2.01 min. |
| 36 | 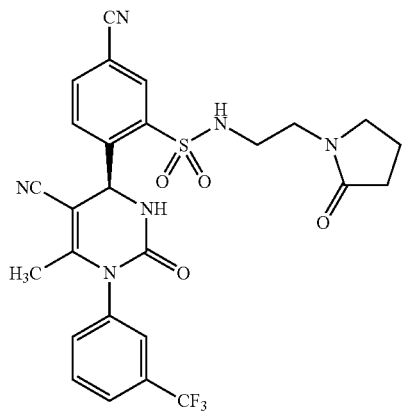 [SMILES: CC1=C(C#N)[C@@H](c2ccc(C#N)cc2S(=O)(=O)NCCN2CCCC2=O)NC(=O)N1c1cccc(C(F)(F)F)c1]<br>5-cyano-2-{(4S)-5-cyano-6-methyl-2-oxo-1-[3-(trifluoromethyl)phenyl]-1,2,3,4-tetrahydropyrimidin-4-yl}-N-[2-(2-oxopyrrolidin-1-yl)ethyl]benzenesulfonamide | MS (ESIpos): m/z = 573 (M + H)$^+$<br>LC-MS (Method 11):<br>R$_t$ = 1.93 min. |

Example 37

(R$_S$)-(4S)-4-[4-Cyano-2-(S-methylsulfonimidoyl)phenyl]-3,6-dimethyl-2-oxo-1-[3-(trifluoromethyl)phenyl]-1,2,3,4-tetrahydropyrimidine-5-carbonitrile or (S$_S$)-(4S)-4-[4-cyano-2-(S-methylsulfonimidoyl)phenyl]-3,6-dimethyl-2-oxo-1-[3-(trifluoromethyl)phenyl]-1,2,3,4-tetrahydropyrimidine-5-carbonitrile (diastereomer 1)

Example 38

(S$_S$)-(4S)-4-[4-Cyano-2-(S-methylsulfonimidoyl)phenyl]-3,6-dimethyl-2-oxo-1-[3-(trifluoromethyl)phenyl]-1,2,3,4-tetrahydropyrimidine-5-carbonitrile or (R$_S$)-(4S)-4-[4-cyano-2-(S-methylsulfonimidoyl)phenyl]-3,6-dimethyl-2-oxo-1-[3-(trifluoromethyl)phenyl]-1,2,3,4-tetrahydropyrimidine-5-carbonitrile (diastereomer 2)

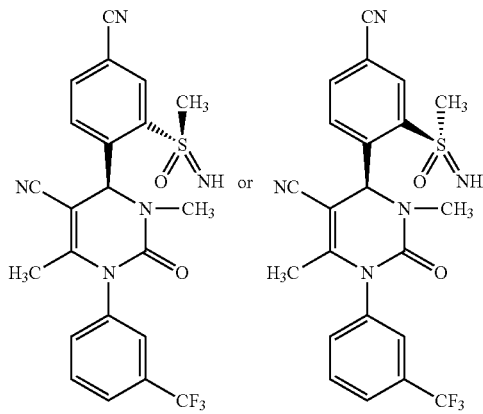 [SMILES: CC1=C(C#N)[C@@H](c2ccc(C#N)cc2[S@](C)(=N)=O)N(C)C(=O)N1c1cccc(C(F)(F)F)c1 ; CC1=C(C#N)[C@@H](c2ccc(C#N)cc2[S@@](C)(=N)=O)N(C)C(=O)N1c1cccc(C(F)(F)F)c1]

The reaction was carried out under argon. The compound from Example 21A ("diastereomer 1"; 63 mg, 111 μmol) was initially charged in an acetonitrile/methanol mixture (10:1, 6 ml). At 0° C., solid potassium carbonate (7.6 mg, 55 μmol; 0.5 eq.) was added, and the reaction was stirred for 15 min. The mixture was then neutralized with trifluoroacetic acid (6.3 mg, 55 μmol; 0.5 eq.) and concentrated under reduced pressure and the residue was purified by preparative HPLC (column: Gromsil C-18, 10 μm; mobile phase: acetonitrile/water+0.1% TFA 10:90→80:20). The title compound was isolated as a solid (48 mg, 91% of theory).

LC-MS (Method 8): R$_t$=0.99 min; MS (ESIpos): m/z (%)=474.3 (100) [M+H]$^+$; MS (ESIneg): m/z (%)=472.4 (100) [M−H]$^−$.

LC-MS (Method 4): R$_t$=1.13 min; MS (ESIpos): m/z (%)=474.1 (100) [M+H]$^+$; MS (ESIneg): m/z (%)=472.4 (100) [M−H]$^−$.

$^1$H-NMR (400 MHz, DMSO-d$_6$): δ=1.80 (s, 3H), 2.70 (s, 3H), 3.30 (s, 3H), 4.85 (s, 1H), 6.75 (s, 1H), 7.70-8.30 (m, 6H), 8.50 (s, 1H).

The reaction was carried out under argon. The compound from Example 22A ("diastereomer 2"; 78 mg, 137 μmol) was initially charged in an acetonitrile/methanol mixture (10:1, 7.7 ml). At 0° C., solid potassium carbonate (9.5 mg, 68 μmol; 0.5 eq.) was added and the reaction was stirred for 15 min. The mixture was then neutralized with trifluoroacetic acid (7.8 mg, 68 μmol; 0.5 eq.) and concentrated under reduced pressure and the residue was purified by preparative HPLC (column: Gromsil C-18, 10 μm; mobile phase: acetonitrile/water+0.1% TFA 10:90→80:20). The title compound was isolated as a solid (60 mg, 93% of theory).

LC-MS (Method 8): R$_t$=0.98 min; MS (ESIpos): m/z (%)=474.3 (100) [M+H]$^+$; MS (ESIneg): m/z (%)=472.4 (100) [M−H]$^−$.

LC-MS (Method 5): R$_t$=1.76 min; MS (ESIpos): m/z (%)=474.1 (100) [M+H]$^+$; MS (ESIneg): m/z (%)=472.2 (100) [M−H]$^−$.

Chiral analytical HPLC [column: Chiralpak AD-H, 5 μm, 250 mm×4.6 mm; mobile phase: isohexane/ethanol 50:50; flow rate: 1 ml/min; injection volume: 10 μl; temperature: 40° C.; detection: 220 nm]: R$_t$=4.40 min.

$^1$H-NMR (400 MHz, DMSO-d$_6$): δ=1.80 (s, 3H), 2.70 (s, 3H), 3.30 (s, 3H), 6.80 (s, 1H), 7.70-8.30 (m, 6H), 8.45 (s, 1H).

[α]$_D^{20°}$=−286.9° (c=0.49, chloroform).

Example 39

(R$_S$)-(4S)-4-[4-Cyano-2-(S-methylsulfonimidoyl)phenyl]-6-methyl-2-oxo-1-[3-(trifluoromethyl)phenyl]-1,2,3,4-tetrahydropyrimidine-5-carbonitrile and (S$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile (diastereomer mixture)

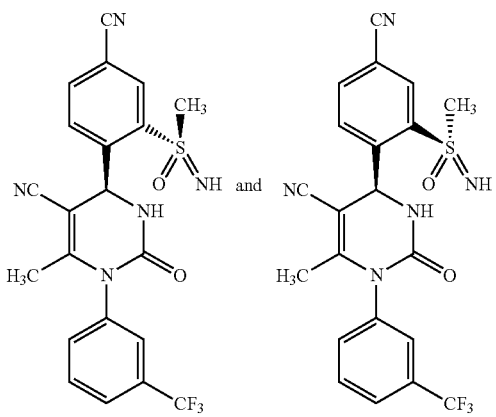 [SMILES: CC1=C(C#N)[C@@H](c2ccc(C#N)cc2[S@](C)(=N)=O)NC(=O)N1c1cccc(C(F)(F)F)c1 ; CC1=C(C#N)[C@@H](c2ccc(C#N)cc2[S@@](C)(=N)=O)NC(=O)N1c1cccc(C(F)(F)F)c1]

The reaction was carried out under argon. The diastereomer mixture from Example 23A (485 mg, 873 µmol) was initially charged in an acetonitrile/methanol mixture (10:1, 44 ml). At 0° C., solid potassium carbonate (60.3 mg, 437 µmol; 0.5 eq.) was added and the reaction was stirred for 15 min. The mixture was then neutralized with trifluoroacetic acid (49.8 mg, 437 µmol; 0.5 eq.) and concentrated under reduced pressure and the residue was taken up in ethyl acetate (50 ml). The organic phase was washed with saturated aqueous sodium chloride solution (2×15 ml), dried over sodium sulfate, filtered and concentrated under reduced pressure. The title compound was isolated as a solid (400 mg, quant.).

LC-MS (Method 6): R$_t$=2.03 min; MS (ESIpos): m/z (%)=417.0 (50), 460.0 (100) [M+H]$^+$.

$^1$H-NMR (400 MHz, DMSO-d$_6$): δ=1.80 (2 s, 3H), 3.30 (2 s, 3H), 4.75 (2 s, 1H), 6.65 (2 s, 1H), 7.70-8.40 (m, 8H).

Example 40

(R$_S$)-(4S)-4-[4-Cyano-2-(S-methylsulfonimidoyl)phenyl]-6-methyl-2-oxo-1-[3-(trifluoromethyl)phenyl]-1,2,3,4-tetrahydropyrimidine-5-carbonitrile or (S$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile (diastereomer 1)

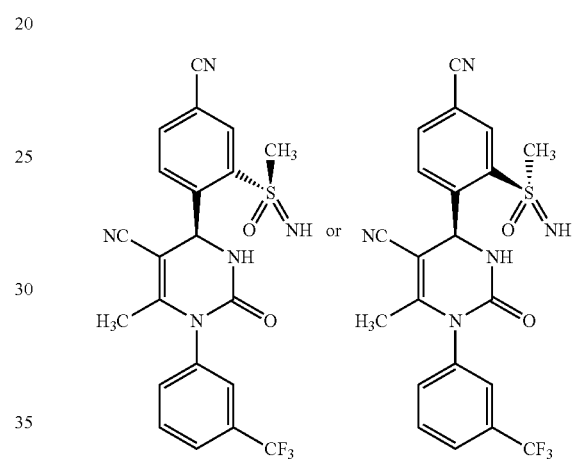

The diastereomer mixture of (R$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile and (S$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile (400 mg) was separated by preparative HPLC chromatography on a chiral phase [column: Daicel Chiralpak AD-H, 250 mm×20 mm; sample preparation: the sample was dissolved in 20 ml of ethanol; injection volume: 0.750 ml; mobile phase: isohexane/ethanol 3:7; flow rate: 15 ml/min; temperature: 40° C.; detection: 220 nm]. Diastereomer 1 was obtained as initially-eluting fraction in the form of a solid (296 mg, 74% of theory, content >99%).

LC-MS (Method 6): R$_t$=2.04 min; MS (ESIpos): m/z (%)=417.0 (40), 460.0 (100) [M+H]$^+$.

$^1$H-NMR (400 MHz, DMSO-d$_6$): δ=1.85 (s, 3H), 3.25 (s, 3H), 4.85 (s, 1H), 6.65 (s, 1H), 7.70-8.40 (m, 8H).

Chiral analytical HPLC [column: Chiralpak AD-H, 5 µm, 250 mm×4.6 mm; mobile phase: isohexane/ethanol 3:7; flow rate: 1 ml/min; injection volume: 10 µl; temperature: 40° C.; detection: 220 nm]: R$_t$=4.16 min.

Example 41

(S$_S$)-(4S)-4-[4-Cyano-2-(S-methylsulfonimidoyl)phenyl]-6-methyl-2-oxo-1-[3-(trifluoromethyl)phenyl]-1,2,3,4-tetrahydropyrimidine-5-carbonitrile or (R$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile (diastereomer 2)

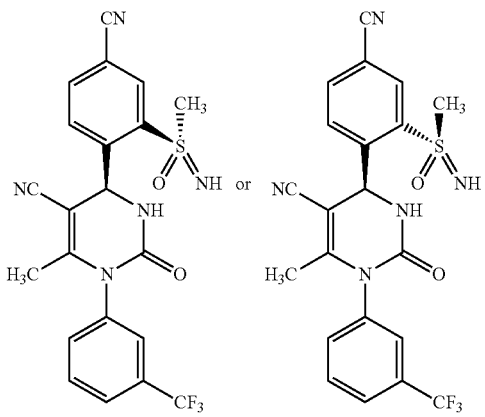 [SMILES: CC1=C(C#N)[C@@H](c2ccc(C#N)cc2[S@@](C)(=N)=O)NC(=O)N1c1cccc(C(F)(F)F)c1 ; CC1=C(C#N)[C@@H](c2ccc(C#N)cc2[S@](C)(=N)=O)NC(=O)N1c1cccc(C(F)(F)F)c1]

The diastereomer mixture of (R$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile and (S$_S$)-(4S)-4-[4-cyano-2-(S-methylsulfonimidoyl)phenyl]-6-methyl-2-oxo-1-[3-(trifluoromethyl)phenyl]-1,2,3,4-tetrahydropyrimidine-5-carbonitrile (400 mg) was separated by preparative HPLC chromatography on a chiral phase [column: Daicel Chiralpak AD-H, 250 mm×20 mm; sample preparation: the sample was dissolved in 20 ml of ethanol; injection volume: 0.750 ml; mobile phase: isohexane/ethanol 3:7; flow rate: 15 ml/min; temperature: 40° C.; detection: 220 nm]. Diastereomer 2 was obtained as later-eluting fraction in the form of a solid (103 mg, 26% of theory, content >98.5%).

LC-MS (Method 6): R$_t$=2.04 min; MS (ESIpos): m/z (%)=417.0 (40), 460.0 (100) [M+H]$^+$.

$^1$H-NMR (400 MHz, DMSO-d$_6$): δ=1.85 (s, 3H), 3.30 (s, 3H), 4.55 (s, 1H), 6.70 (s, 1H), 7.70-8.30 (m, 7H), 8.40 (s, 1H).

Chiral analytical HPLC [column: Chiralpak AD-H, 5 µm, 250 mm×4.6 mm; mobile phase: isohexane/ethanol 3:7; flow rate: 1 ml/min; injection volume: 10 µl; temperature: 40° C.; detection: 220 nm]: R$_t$=4.94 min.

Example 42

(R$_S$)-(4S)-4-[4-Cyano-2-(S-methylsulfonimidoyl)phenyl]-6-methyl-3-(methylsulfonyl)-2-oxo-1-[3-(trifluoromethyl)phenyl]-1,2,3,4-tetrahydropyrimidine-5-carbonitrile and (S$_S$)-(4S)-4-[4-cyano-2-(S-methylsulfonimidoyl)phenyl]-6-methyl-3-(methylsulfonyl)-2-oxo-1-[3-(trifluoromethyl)phenyl]-1,2,3,4-tetrahydropyrimidine-5-carbonitrile (diastereomer mixture)

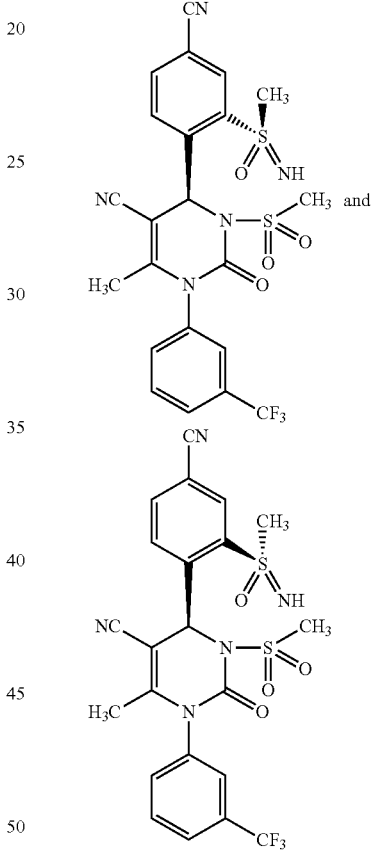

The reaction was carried out under argon. The diastereomer mixture from Example 25A (25 mg, 39 µmol) was initially charged in an acetonitrile/methanol mixture (10:1, 2.2 ml). At 0° C., solid potassium carbonate (2.7 mg, 20 µmol; 0.5 eq.) was added and the reaction was stirred for 15 min. The mixture was then neutralized with trifluoroacetic acid (2.3 mg, 20 µmol; 0.5 eq.) and concentrated under reduced pressure and the residue was purified by preparative HPLC (column: Gromsil C-18, 10 µm; mobile phase: acetonitrile/water+0.1% TFA 10:90→75:25). The title compound was isolated as a colorless solid (4.3 mg, 20% of theory).

LC-MS (Method 5): R$_t$=1.84 min; MS (ESIpos): m/z (%)=538.3 (100) [M+H]$^+$; MS (ESIneg): m/z (%)=415.3 (100), 536.3 (100) [M−H]$^−$.

B. ASSESSMENT OF THE PHARMACOLOGICAL ACTIVITY

The pharmacological effect of the compounds of the invention can be shown in the assays described below:

Abbreviations

AMC 7-amido-4-methylcoumarin
BNP brain natriuretic peptide
BSA bovine serum albumin
HEPES N-(2-hydroxyethyl)piperazine-N'-2-ethanesulfonic acid
HNE humane neutrophil elastase
IC inhibitory concentration
MeOSuc methoxysuccinyl
NADP nicotinamide adenine dinucleotide phosphate
PBS phosphate-buffered saline
PEG polyethylene glycol
v/v volume to volume ratio (of a solution)
w/v weight to volume ratio (of a solution)

B-1. In Vitro HNE Inhibition Assay

The potency of the compounds of the invention is ascertained in an in vitro inhibition assay. The HNE-mediated amidolytic cleavage of a suitable peptide substrate leads in this connection to an increase in the fluorescent light. The signal intensity of the fluorescent light is directly proportional to the enzyme activity. The effective concentration of a test compound at which half the enzyme is inhibited (50% signal intensity of the fluorescent light) is indicated as $IC_{50}$.

Procedure:

Enzyme (80 pM HNE; from Serva, Heidelberg) and substrate (20 μM MeOSuc-Ala-Ala-Pro-Val-AMC; from Bachem, Weil am Rhein) are incubated in an assay volume of in total 50 μl of assay buffer (0.1 M HEPES pH 7.4, 0.5 M NaCl, 0.1% w/v BSA, 1% v/v DMSO) in a 384-well microtiter plate in the presence and absence of the test substance at 37° C. for 2 hours. The intensity of the fluorescent light from the assay mixtures is measured (Ex. 380 nm, Em. 460 nm). The $IC_{50}$ values are determined by plotting the intensity of the fluorescent light against the active compound concentration.

Representative $IC_{50}$ values for the compounds of the invention (at an HNE concentration of 80 pM) are shown in Table A below:

TABLE A

| Inhibition of human neutrophil elastase (HNE) | |
|---|---|
| Exemplary embodiment No. | $IC_{50}$ [nM] |
| 1 | 0.4 |
| 2 | <0.3 |
| 3 | <0.3 |
| 4 | <0.3 |
| 10 | <0.3 |
| 11 | <0.3 |
| 13 | <0.3 |
| 14 | 4.5 |
| 21 | 0.7 |
| 37 | <0.3 |
| 38 | <0.3 |
| 41 | 0.9 |

B-2. Animal Model of Pulmonary Arterial Hypertension

The monocrotaline-induced pulmonary hypertension in rats is a widely used animal model of pulmonary arterial hypertension. The pyrrolizidine alkaloid monocrotaline is metabolized after subcutaneous injection to the toxic monocrotalinepyrrole in the liver and leads within a few days to endothelial damage in the pulmonary circulation, followed by a remodeling of the small pulmonary arteries (media hypertrophy, de novo muscularization). A single subcutaneous injection is sufficient to induce pronounced pulmonary hypertension in rats within 4 weeks [Cowan et al., Nature Med. 6, 698-702 (2000)].

Male Sprague-Dawley rats are used for the model. On day 0, the animals receive a subcutaneous injection of 60 mg/kg monocrotaline. Treatment of the animals begins no earlier than 14 days after the monocrotaline injection and extends over a period of at least 14 days. At the end of the study, the animals undergo hemodynamic investigations, and the arterial and central venous oxygen saturation are determined. For the hemodynamic measurement, the rats are initially anesthetized with pentobarbital (60 mg/kg). The animals are then tracheotomized and artificially ventilated (rate: 60 breaths/min; inspiration to expiration ratio: 50:50; positive end-expiratory pressure: 1 cm $H_2O$; tidal volume: 10 ml/kg of body weight; $FIO_2$: 0.5). The anesthesia is maintained by isoflurane inhalation anesthesia. The systemic blood pressure is determined in the left carotid artery using a Millar microtip catheter. A polyethylene catheter is advanced through the right jugular vein into the right ventricle to determine the right ventricular pressure. The cardiac output is determined by thermodilution. Following the hemodynamics, the heart is removed and the ratio of right to left ventricle including septum is determined. In addition, plasma samples are obtained to determine biomarkers (for example proBNP) and plasma substance levels.

B-3. Animal Model of Acute Lung Failure

Elastase-induced lung failure in mice, rats or hamsters is a widely used animal model of acute lung failure (also: "acute lung injury", "acute respiratory distress syndrome") [Tremblay et al., Chest 121, 582-588 (2002); Kuraki et al., Am. J. Resp. Crit. Care Med. 166, 596-500 (2002)]. The animals are treated 1 hour prior to orotracheal instillation of human neutrophil elastase (HNE). 2 hours after orotracheal HNE instillation, a bronchoalveolar lavage is carried out, and the hemoglobin content and the differential cell picture of the lavage are determined

B-4. Animal Model of Pulmonary Emphysema

Elastase-induced pulmonary emphysema in mice, rats or hamsters is a widely used animal model of pulmonary emphysema [Sawada et al., Exp. Lung Res. 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, the pulmonary compliance is determined, and an alveolar morphometry is carried out.

B-5. CYP Inhibition Assay

The ability of substances to be able to inhibit CYP1A2, CYP2C9, CYP2D6 and CYP3A4 in humans is investigated with pooled human liver microsomes as enzyme source in the presence of standard substrates (see below) which form CYP-specific metabolites. The inhibitory effects are investigated with six different concentrations of the test compounds [2.8, 5.6, 8.3, 16.7, 20 (or 25) and 50 μM], compared with the extent of the CYP-specific metabolite formation of the standard substrates in the absence of the test compounds, and the corresponding $IC_{50}$ values are calculated. A standard inhibitor which specifically inhibits a single CYP isoform is always included in the incubation in order to make the results comparable between different series.

Procedure:

Incubation of phenacetin, diclofenac, tolbutamide, dextromethorphan or midazolam with human liver microsomes in the presence of in each case six different concentrations of a test compound (as potential inhibitor) is carried out on a work station (Tecan, Genesis, Crailsheim, Germany). Standard incubation mixtures comprise 1.3 mM NADP, 3.3 mM $MgCl_2 \times 6$ $H_2O$, 3.3 mM glucose 6-phosphate, glucose 6-phosphate dehydrogenase (0.4 U/ml) and 100 mM phosphate buffer (pH 7.4) in a total volume of 200 µl. Test compounds are preferably dissolved in acetonitrile. 96-well plates are incubated with pooled human liver microsomes at 37° C. for a defined time. The reactions are stopped by adding 100 µl of acetonitrile in which a suitable internal standard is always present. Precipitated proteins are removed by centrifugation, and the supernatants are combined and analyzed by LC-MS/MS.

B-6. Hepatocyte Assay to Determine the Metabolic Stability

The metabolic stability of test compounds in the presence of hepatocytes is determined by incubating the compounds with low concentrations (preferably below or around 1 µM) and with low cell counts (preferably $1*10^6$ cells/ml) in order to ensure as far as possible linear kinetic conditions in the experiment. Seven samples of the incubation solution are taken in a fixed time pattern for the LD-MS analysis in order to determine the half-life (i.e. the degradation) of the compound in each case. Various clearance parameters (CL) and $F_{max}$ values are calculated from this half-life (see below).

The Cl and $F_{max}$ values represent a measure of the phase 1 and phase 2 metabolism of the compounds in the hepatocytes. In order to minimize the influence of the organic solvent on the enzymes in the incubation mixtures, this concentration is generally limited to 1% (acetonitrile) or 0.1% (DMSO).

A cell count for hepatocytes in the liver of $1.1*10^8$ cells/g of liver is used for calculation for all species and breeds. CL parameters calculated on the basis of half-lives extending substantially beyond the incubation time (normally 90 minutes) can be regarded only as rough guidelines.

The calculated parameters and their meaning are:

$F_{max}$ well-stirred [%] maximum possible bioavailability after oral administration Calculation: $(1-CL_{blood}$ well-stirred$/QH)*100$ $CL_{blood}$ well-stirred [L/(h*kg)] calculated blood clearance (well-stirred model)

Calculation: $(QH*CL'_{intrinsic})/(QH+CL'_{intrinsic})$ $CL'_{intrinsic}$ [ml/(min*kg)] maximum ability of the liver (of the hepatocytes) to metabolize a compound (on the assumption that the hepatic blood flow is not rate-limiting)

Calculation: $CL'_{intrinsic, apparent}*$species-specific hepatocyte count $[1.1*10^8$/g of liver]*species-specific liver weight [g/kg]

$CL'_{intrinsic, apparent}$ [ml/(min*mg)] normalizes the elimination constant by dividing it by the hepatocyte cell count x $(x*10^6$/ml) employed Calculation: $k_{el}$ [1/min]/(cell count $[x*10^6]$/incubation volumes [ml])

(QH=species-specific hepatic blood flow).

Representative values for the compounds according to the invention from this assay after incubation of the compounds with rat hepatocytes are shown in Table B below:

TABLE B calculated blood clearance and bioavailability after incubation with rat hepatocytes

| Exemplary embodiment No. | $CL_{blood}$ [L/(h*kg)] | $F_{max}$ [%] |
|---|---|---|
| 1 | 0.1 | 97 |
| 2 | 1.9 | 54 |
| 13 | 1.9 | 54 |
| 38 | 0.0 | 99 |
| 41 | 0.0 | 100 |

B-7. Determination of the Solubility

Reagents Required:

PBS buffer pH 6.5: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1 N hydrochloric acid (for example from Merck, Art. No. 1.09057.1000) the pH is then adjusted to 6.5.

PEG/water solution (70:30 v/v): 70 ml of polyethylene glycol 400 (for example from Merck, Art. No. 8.17003.1000) and 30 ml of distilled water are homogenized in a 100 ml measuring flask.

PEG/PBS buffer pH 6.5 (20:80 v/v): 20 ml of polyethylene glycol 400 (for example from Merck, Art. No. 8.17003.1000) and 80 ml of PBS buffer pH 6.5 are homogenized in a 100 ml measuring flask.

Dimethyl sulfoxide (for example from Baker, Art. No. 7157.2500)

Distilled water.

Preparation of the Starting Solution (Original Solution):

At least 4 mg of the test substance are weighed accurately into a wide-necked 10 mm screw V vial (from Glastechnik Gräfenroda GmbH, Art. No. 8004-WM-HN15µ) with fitting screw cap and septum, in a pipetting robot DMSO is added to a concentration of 50 mg/ml and the mixture is shaken for 10 minutes.

Preparation of the Calibration Solutions:

Preparation of the Starting Solution for Calibration Solutions (Stock Solution):

With the aid of a pipetting robot, 10 µl of the original solution are transferred into a microtiter plate and made up with DMSO to a concentration of 600 µg/ml. The sample is shaken until everything has gone into solution.

Calibration Solution 1 (20 µg/ml):

1000 µl of DMSO are added to 34.4 µl of the stock solution, and the mixture is homogenized.

Calibration Solution 2 (2.5 µg/ml):

700 µl of DMSO are added to 100 µl of calibration solution 1, and the mixture is homogenized.

Preparation of the Sample Solutions:

Sample Solution for Solubilities of Up to 5 g/Liter in PBS Buffer pH 6.5:

10 µl of the original solution are transferred into a microtiter plate, and 1000 µl of PBS buffer pH 6.5 are added.

Sample Solution for Solubilities of Up to 5 g/Liter in PEG/Water (70:30):

10 µl of the original solution are transferred into a microtiter plate, and 1000 µl of PEG/water (70:30) are added.

Sample Solution for Solubilities of Up to 5 g/Liter in PEG/PBS Buffer pH 6.5 (20:80):

10 µl of the original solution are transferred into a microtiter plate, and 1000 µl of PEG/PBS buffer pH 6.5 (20:80) are added.

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 µl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 µl of the supernatant are removed and diluted 1:5 and 1:100 with DMSO. From each dilution, a sample is transferred into a vessel suitable for HPLC analysis.

Analysis:

The samples are analysed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 µg/ml; 3) sample solution 1:5; 4) sample solution 1:100.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

Table C below shows the solubility, determined by this method, of compounds according to the invention in PBS buffer at pH 6.5:

TABLE C

| Solubility in PBS buffer pH 6.5 | |
| --- | --- |
| Exemplary embodiment No. | Solubility [mg/liter] |
| 11 | 300 |
| 38 | 300 |

C. EXEMPLARY EMBODIMENTS OF PHARMACEUTICAL COMPOSITIONS

The compounds of the invention can be converted into pharmaceutical preparations in the following ways:

Tablets:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400.20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

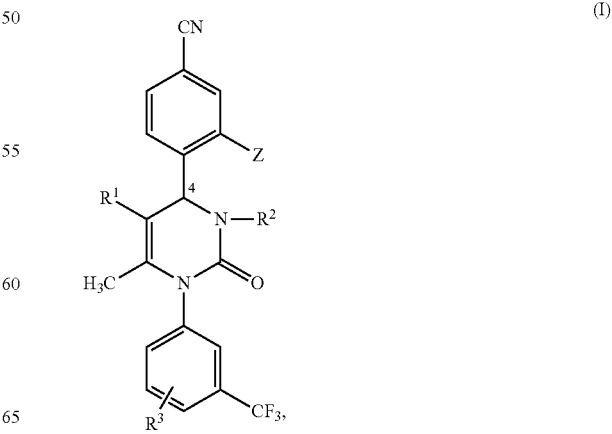

in which

Z represents a sulfonamide grouping of the formula

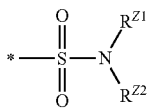

or represents a sulfoximine grouping of the formula

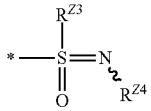

in which
* denotes the point of attachment to the phenyl ring,
$R^{Z1}$ represents hydrogen, or represents $(C_1-C_6)$-alkyl which may be substituted by hydroxyl, $(C_1-C_4)$-alkoxy, amino, mono- or di-$(C_1-C_4)$-alkylamino and up to three times by fluorine,
$R^{Z2}$ represents hydrogen, $(C_3-C_6)$-cycloalkyl, 4- to 6-membered heterocyclyl or 5- or 6-membered heteroaryl
or
represents $(C_1-C_6)$-alkyl which may be substituted by hydroxyl, $(C_1-C_4)$-alkoxy, amino, mono- or di-$(C_1-C_4)$-alkylamino, $(C_1-C_4)$-alkylcarbonylamino, $(C_1-C_4)$-alkoxycarbonylamino, $(C_1-C_4)$-alkylsulfinyl, $(C_1-C_4)$-alkylsulfonyl, $(C_3-C_6)$-cycloalkyl, phenyl, 4- to 6-membered heterocyclyl, 5- or 6-membered heteroaryl or a group of the formula —C(=O)—$NR^{Z5}R^{Z6}$ and up to three times by fluorine,
where the alkoxy substituent mentioned for its part may be substituted up to three times by fluorine,
and where
the heterocyclyl groups mentioned may be substituted up to two times by identical or different substituents from the group consisting of fluorine, $(C_1-C_4)$-alkyl, oxo, hydroxyl, $(C_1-C_4)$-alkoxy, amino, mono- and di-$(C_1-C_4)$-alkylamino
and
the phenyl group mentioned and the heteroaryl groups mentioned may be substituted up to two times by identical or different substituents from the group consisting of fluorine, chlorine, cyano, $(C_1-C_4)$-alkyl, difluoromethyl, trifluoromethyl and $(C_1-C_4)$-alkoxy,
and where
$R^{Z5}$ and $R^{Z6}$ are identical or different and independently of one another represent hydrogen or $(C_1-C_4)$-alkyl
or
$R^{Z5}$ and $R^{Z6}$ together with the nitrogen atom to which they are attached form a 4- to 6-membered aza heterocycle which may contain a further ring heteroatom from the group consisting of N, O and S and may be substituted by $(C_1-C_4)$-alkyl, oxo, hydroxyl, $(C_1-C_4)$-alkoxy, amino, mono- or di-$(C_1-C_4)$-alkylamino,
or
$R^{Z1}$ and $R^{Z2}$ together with the nitrogen atom to which they are attached form a 4- to 10-membered aza heterocycle which may contain a further ring heteroatom from the group consisting of N, O and S and may be substituted up to two times by identical or different substituents from the group consisting of fluorine, $(C_1-C_4)$-alkyl, oxo, hydroxyl, $(C_1-C_4)$-alkoxy, amino, mono- and di-$(C_1-C_4)$-alkylamino,
$R^{Z3}$ represents $(C_1-C_6)$-alkyl which may be substituted by $(C_3-C_6)$-cycloalkyl or up to three times by fluorine, or represents phenyl which may be substituted up to two times by identical or different substituents from the group consisting of fluorine, chlorine, cyano, $(C_1-C_4)$-alkyl, difluoromethyl and trifluoromethyl, or represents $(C_3-C_6)$-cycloalkyl,
and
$R^{Z4}$ represents hydrogen, $(C_1-C_4)$-alkyl or $(C_3-C_6)$-cycloalkyl,
$R^1$ represents cyano or acetyl,
$R^2$ represents hydrogen, represents $(C_1-C_4)$-alkyl or $(C_1-C_4)$-alkylsulfonyl which may be substituted up to three times by fluorine, or represents a group of the formula —$CH_2$—C(=O)—NH—$R^4$ in which
$R^4$ represents hydrogen, represents $(C_1-C_4)$-alkyl which may be substituted by $(C_3-C_6)$-cycloalkyl or up to three times by fluorine, or represents $(C_3-C_6)$-cycloalkyl,
and
$R^3$ represents hydrogen, fluorine or chlorine,
or a salt, a solvate or a solvate of a salt thereof.

2. The compound of claim 1 in which
Z represents a sulfonamide grouping of the formula

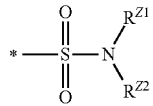

or represents a sulfoximine grouping of the formula

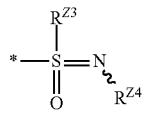

in which
* denotes the point of attachment to the phenyl ring,
$R^{Z1}$ represents hydrogen or represents $(C_1-C_4)$-alkyl which may be substituted by hydroxyl, methoxy or ethoxy,
$R^{Z2}$ represents hydrogen, $(C_3-C_6)$-cycloalkyl, 5- or 6-membered heterocyclyl or 5- or 6-membered heteroaryl
or
represents $(C_1-C_4)$-alkyl which may be substituted by hydroxyl, $(C_1-C_4)$-alkoxy, amino, mono- or di-$(C_1-C_4)$-alkylamino, $(C_1-C_4)$-alkylcarbonylamino, $(C_1-C_4)$-alkoxycarbonylamino, $(C_1-C_4)$-alkylsulfinyl, $(C_1-C_4)$-alkylsulfonyl, $(C_3-C_6)$-cycloalkyl, phenyl, 5- or 6-membered heterocyclyl, 5- or 6-membered heteroaryl or a group of the formula —C(=O)—$NR^{Z5}R^{Z6}$ and up to three times by fluorine,
where the alkoxy substituent mentioned for its part may be substituted up to three times by fluorine,
and where
the heterocyclyl groups mentioned may be substituted up to two times by identical or different substituents from the group consisting of $(C_1-C_4)$-alkyl, oxo, hydroxyl and $(C_1-C_4)$-alkoxy and the phenyl group mentioned and the heteroaryl groups mentioned may be substituted up to two times by identical or different substituents from the group consisting of fluorine, chlorine, cyano, $(C_1-C_4)$-alkyl, trifluoromethyl and $(C_1-C_4)$-alkoxy, and where $R^{Z5}$ and $R^{Z6}$ are identical or different and independently of one another represent hydrogen or $(C_1-C_4)$-alkyl or $R^{Z5}$ and $R^{Z6}$ together with the nitrogen atom to which they are attached form a 5- or 6-membered aza heterocycle which may contain a further ring heteroatom from the group consisting of N and O and may be substituted by $(C_1-C_4)$-alkyl, oxo, hydroxyl or $(C_1-C_4)$-alkoxy, or $R^{Z1}$ and $R^{Z2}$ together with the nitrogen atom to which they are attached form a 5- to 10-membered aza heterocycle which may contain a further ring heteroatom from the group consisting of N and O and may be substituted up to two times by identical or different substituents from the group consisting of $(C_1-C_4)$-alkyl, oxo, hydroxyl and $(C_1-C_4)$-alkoxy, $R^{Z3}$ represents $(C_1-C_4)$-alkyl which may be substituted by $(C_3-C_6)$-cycloalkyl or up to three times by fluorine, or represents phenyl which may be substituted up to two times by identical or different substituents from the group consisting of fluorine, chlorine, cyano, methyl and trifluoromethyl, or represents $(C_3-C_6)$-cycloalkyl, and $R^{Z4}$ represents hydrogen, methyl or cyclopropyl, $R^1$ represents cyano, $R^2$ represents hydrogen, $(C_1-C_4)$-alkyl or $(C_1-C_4)$-alkylsulfonyl, each of which may be substituted up to three times by fluorine, or represents a group of the formula —$CH_2$—C(=O)—NH—$R^4$ in which $R^4$ represents hydrogen, methyl, cyclopropyl or cyclopropylmethyl, and $R^3$ represents hydrogen or fluorine, or a salt, a solvate or a solvate of a salt thereof.

3. The compound of claim 1 in which

Z represents a sulfonamide grouping of the formula

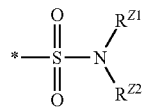

in which

* denotes the point of attachment to the phenyl ring, $R^{Z1}$ represents hydrogen, methyl or 2-hydroxyethyl, $R^{Z2}$ represents hydrogen, cyclopropyl, 5- or 6-membered heterocyclyl or 5- or 6-membered heteroaryl or represents $(C_1-C_4)$-alkyl which may be substituted by hydroxyl, methoxy, ethoxy, amino, methylamino, ethylamino, dimethylamino, diethylamino, acetylamino, cyclopropyl, 5- or 6-membered heterocyclyl or a group of the formula —C(=O)—$NR^{Z5}R^{Z6}$, where methoxy and ethoxy substituents mentioned for their part may be substituted up to three times by fluorine, and where the heterocyclyl groups mentioned may be substituted up to two times by identical or different substituents from the group consisting of methyl, ethyl, oxo, hydroxyl, methoxy and ethoxy and the heteroaryl group mentioned may be substituted up to two times by identical or different substituents from the group consisting of fluorine, chlorine, cyano, methyl, ethyl, trifluoromethyl, methoxy and ethoxy, and where $R^{Z5}$ and $R^{Z6}$ independently of one another represent hydrogen or methyl or together with the nitrogen atom to which they are attached form a pyrrolidine, piperidine or morpholine ring, or $R^{Z1}$ and $R^{Z2}$ together with the nitrogen atom to which they are attached form a pyrrolidine, piperidine or morpholine ring, $R^1$ represents cyano, $R^2$ represents hydrogen, methyl, methylsulfonyl or the group of the formula —$CH_2$—C(=O)—$NH_2$, and $R^3$ represents hydrogen, or a salt, a solvate or a solvate of a salt thereof.

4. The compound of claim 1 in which

Z represents a sulfoximine grouping of the formula

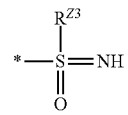

in which

* denotes the point of attachment to the phenyl ring and $R^{Z3}$ represents $(C_1-C_4)$-alkyl which may be substituted by cyclopropyl or up to three times by fluorine, or represents cyclopropyl, $R^1$ represents cyano, $R^2$ represents hydrogen, methyl, methylsulfonyl or the group of the formula —$CH_2$—C(=O)—$NH_2$, and $R^3$ represents hydrogen, or a salt, a solvate or a solvate of a salt thereof.

5. The compound of claim 1 in which

Z represents a sulfonamide grouping of the formula

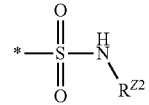

in which

* denotes the point of attachment to the phenyl ring and $R^{Z2}$ represents hydrogen, methyl or the group of the formula —CH$_2$—C(=O)—NH$_2$, $R^1$ represents cyano, $R^2$ represents hydrogen, methyl or methylsulfonyl, and $R^3$ represents hydrogen, or a salt, a solvate or a solvate of a salt thereof.

6. The compound of claim 1 in which

Z represents a sulfoximine grouping of the formula $$*-\underset{\underset{O}{\|}}{\overset{\overset{CH_3}{|}}{S}}=NH$$

in which

* denotes the point of attachment to the phenyl ring, $R^1$ represents cyano, $R^2$ represents hydrogen, methyl or methylsulfonyl, and $R^3$ represents hydrogen, or a salt, a solvate or a solvate of a salt thereof.

7. A process for preparing a compound of the formula (I) of claim 1, in which Z represents a sulfonamide grouping of the formula $$*-\underset{\underset{O}{\|}}{\overset{\overset{O}{\|}}{S}}-N\overset{R^{Z1}}{\underset{R^{Z2}}{}}$$

in which

* denotes the point of attachment to the phenyl ring and $R^{Z1}$ and $R^{Z2}$ have the meanings given in claim 1, comprising:

converting an aniline derivative of the formula (II)

(II)

[Structure of formula (II) showing a phenyl ring with CN and NH$_2$ substituents connected to a pyrimidinone ring with R$^1$, R$^2$, H$_3$C groups and a phenyl ring with R$^3$ and CF$_3$ substituents]

in which $R^1$, $R^2$ and $R^3$ have the meanings given in claim 1, with sodium nitrite and hydrochloric acid into the corresponding diazonium salt and reacting the diazonium salt in a one-pot reaction with sulfur dioxide in the presence of copper(I) chloride to give a sulfonyl chloride of the formula (III)

(III)

[Structure of formula (III) showing a phenyl ring with CN and SO$_2$Cl substituents connected to a pyrimidinone ring with R$^1$, R$^2$, H$_3$C groups and a phenyl ring with R$^3$ and CF$_3$ substituents]

in which $R^1$, $R^2$ and $R^3$ have the meanings given above, reacting the sulfonyl chloride of the formula (III) with an amine of the formula (IV)

(IV)

$$HN\overset{R^{Z1}}{\underset{R^{Z2}}{}},$$

in which $R^{Z1}$ and $R^{Z2}$ have the meanings given in any of claims 1, 2, 3 and 5, if appropriate in the presence of an auxiliary base, to give the sulfonamide of the formula (I-A)

(I-A)

[Structure of formula (I-A) showing a phenyl ring with CN and SO$_2$N(R$^{Z1}$)(R$^{Z2}$) substituents connected to a pyrimidinone ring with R$^1$, R$^2$, H$_3$C groups and a phenyl ring with R$^3$ and CF$_3$ substituents]

in which $R^1$, $R^2$, $R^3$, $R^{Z1}$ and $R^{Z2}$ have the meanings given above, and optionally, separating compounds of the formula (I-A) obtained in this manner by methods known to the person skilled in the art into their enantiomers and/or diastereomers and/or converted with the appropriate (i) solvents and/or (ii) bases or acids into their solvates, salts and/or solvates of the salts.

8. A process for preparing a compound of the formula (I) of claim 1, in which Z represents a sulfoximine grouping of the formula

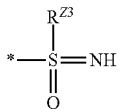

in which
* denotes the point of attachment to the phenyl ring and
$R^{Z3}$ has the meaning given in any of claims 1, 2, 4 and 6, comprising,
oxidizing a phenyl thioether derivative of the formula (V)

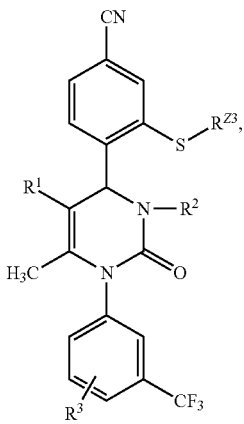

(V)

in which $R^1$, $R^2$, $R^3$ and $R^{Z3}$ have the meanings given in any of claims 1, 2, 4 and 6,
with hydrogen peroxide, a peracid or a periodate to give the sulfoxide of the formula (VI)

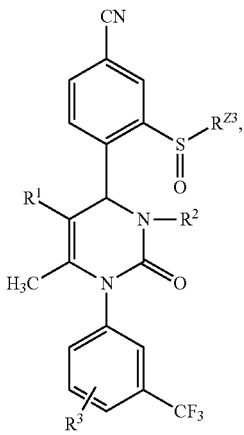

(VI)

in which $R^1$, $R^2$, $R^3$ and $R^{Z3}$ have the meanings given above, converting the sulfoxide of formula (VI) with 2,2,2-trifluoroacetamide and (diacetoxyiodo)benzene in the presence of dimeric rhodium(II) acetate as catalyst and magnesium oxide as base into an N-acylsulfoximine of the formula (VII)

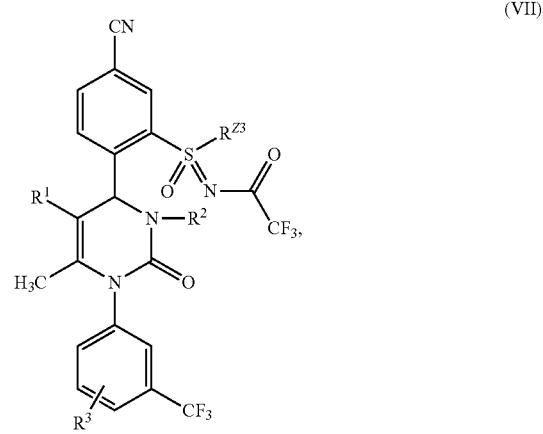

(VII)

in which $R^1$, $R^2$, $R^3$ and $R^{Z3}$ have the meanings given above,
and removing the trifluoroacetyl group in the N-acylsulfoximine of the formula (VII) under basic conditions to give the sulfoximine of the formula (I-B)

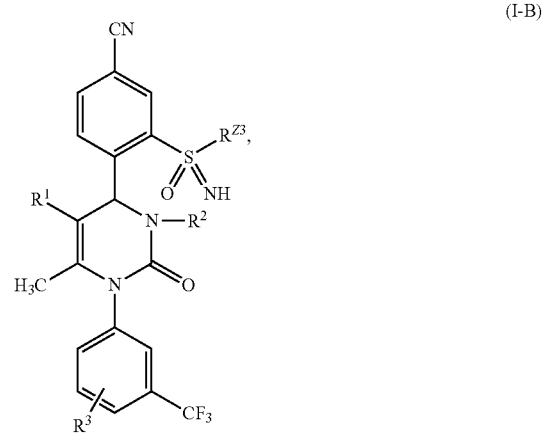

(I-B)

in which $R^1$, $R^2$, $R^3$ and $R^{Z3}$ have the meanings given above,
and optionally separating the compounds of the formula (I-B) obtained in this manner by methods known to the person skilled in the art into their enantiomers and/or diastereomers and/or converted with the appropriate (i) solvents and/or (ii) bases or acids into their solvates, salts and/or solvates of the salts.

9. A pharmaceutical composition comprising a compound of claim 1 in combination with one or more inert non-toxic pharmaceutically acceptable auxiliaries.

* * * * *

UNITED STATES PATENT AND TRADEMARK OFFICE
CERTIFICATE OF CORRECTION

PATENT NO.         : 8,691,817 B2
APPLICATION NO.    : 13/262159
DATED              : April 8, 2014
INVENTOR(S)        : Von Nussbaum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this

Twenty-ninth Day of September, 2015

Michelle K. Lee
*Director of the United States Patent and Trademark Office*